United States Patent
Booth et al.

(10) Patent No.: US 10,939,868 B2
(45) Date of Patent: Mar. 9, 2021

(54) METHOD OF PREDICTING RAPID PROGRESSION OF FIBROSIS AND THERAPY AND REAGENTS THEREFOR

(71) Applicants: Western Sydney Local Health District, Westmead (AU); The University of Sydney, Sydney (AU)

(72) Inventors: David Booth, Chatswood (AU); Jacob George, West Pennant Hills (AU); Mohammed Eslam, Westmead (AU); Golo Ahlenstiel, Ryde (AU); Kate O'Connor, Kirribilli (AU)

(73) Assignees: WESTERN SYDNEY LOCAL HEALTH DISTRICT, Westmead (AU); THE UNIVERSITY OF SYDNEY, Sydney (AU)

( * ) Notice: Subject to any disclaimer, the term of this patent is extended or adjusted under 35 U.S.C. 154(b) by 618 days.

(21) Appl. No.: 15/325,704

(22) PCT Filed: Jul. 17, 2015

(86) PCT No.: PCT/AU2015/050404
§ 371 (c)(1),
(2) Date: Jan. 11, 2017

(87) PCT Pub. No.: WO2016/008014
PCT Pub. Date: Jan. 21, 2016

(65) Prior Publication Data
US 2018/0263556 A1 Sep. 20, 2018

(30) Foreign Application Priority Data

Jul. 18, 2014 (AU) ............................... 2014902788
Jul. 25, 2014 (AU) ............................... 2014902881

(51) Int. Cl.
| | |
|---|---|
| A61B 5/00 | (2006.01) |
| C12Q 1/68 | (2018.01) |
| C12Q 1/6883 | (2018.01) |
| G16B 20/00 | (2019.01) |
| G16B 20/20 | (2019.01) |
| G16H 50/30 | (2018.01) |
| G01N 33/53 | (2006.01) |

(52) U.S. Cl.
CPC .............. *A61B 5/4842* (2013.01); *A61B 5/45* (2013.01); *C12Q 1/68* (2013.01); *C12Q 1/6883* (2013.01); *G01N 33/5308* (2013.01); *G16B 20/00* (2019.02); *G16B 20/20* (2019.02); *G16H 50/30* (2018.01); *C12Q 2600/156* (2013.01)

(58) Field of Classification Search
None
See application file for complete search history.

(56) References Cited

U.S. PATENT DOCUMENTS 7,639,640 B2 * 12/2009 Fujii .................... H04L 63/101
370/328

FOREIGN PATENT DOCUMENTS

WO WO 2013/150002 A1 10/2013

OTHER PUBLICATIONS

DbSNP rs12979860 [retrieved Nov. 24, 2019] Retrieved from the Internet,https://www.ncbi.nlm.nih.gov/snp/rs1297860#submissions (Year: 2019).*
DbSNP rs4374383 [retrieved Nov. 24, 2019] Retrieved from the Internet,https://www.ncbi.nlm.nih.gov/snp/rs4374383#submissions (Year: 2019).*
Bochud, Pierre-Yves, et al., "IL28B Alleles Associated With Poor Hepatitis C Virus (HCV) Clearance Protect Against Inflammation and Fibrosis in Patients Infected With Non-1 HCV Genotypes," Hepatology, 2012, vol. 55, No. 2, pp. 384-394.
Patin E. et al., "Genome-Wide Association Study Identifies Variants Associated with Progression of Liver Fibrosis from HCV Infection," Gastroenterology, 2012, vol. 143, No. 5, pp. 1244-1252.
Sato, M. et al., "Impact of IL28B Genetic Variation on HCV-Induced Liver Fibrosis, Inflammation, and Steatosis: A Meta-Analysis," PLOS One, Mar. 2014, vol. 9, No. 3, e91822.
International Search Report dated Aug. 14, 2015 for PCT/AU2015/050404, filed Jul. 17, 2015.
International Preliminary Report on Patentability dated Jan. 24, 2017 for PCT/AU2015/050404, filed Jul. 17, 2015.

* cited by examiner

*Primary Examiner* — John S Brusca
(74) *Attorney, Agent, or Firm* — Knobbe, Martens, Olson & Bear LLP

(57) ABSTRACT

This invention relates to molecular diagnostics and, more specifically DNA-based tests for the prognosis and/or monitoring of fibrotic disease progression in humans, and processes for stratifying patients based on their likely rates of fibrotic disease progression. The invention also relates to the field of therapy for fibrotic disease, based on such prognoses, monitoring and stratification results, such as in monitoring and/or stratifying and/or treating patients having a higher likelihood of rapid fibrotic disease progression.

35 Claims, 8 Drawing Sheets

METHOD OF PREDICTING RAPID PROGRESSION OF FIBROSIS AND THERAPY AND REAGENTS THEREFOR

RELATED APPLICATIONS DATA

The present application claims priority from Australian Provisional Patent Application No. 2014902788 filed on 18 Jul. 2014 and Australian Provisional Patent Application No. 2014902881 filed on 25 Jul. 2014, the full content of each of which is incorporated herein by reference.

FIELD OF THE INVENTION

This invention is in the field of molecular diagnostics and, more specifically DNA-based tests for the prognosis and/or monitoring of fibrotic disease progression in humans, and processes for stratifying patients based on their likely rates of fibrotic disease progression, and computer-based devices and systems suitable for use with such processes. The invention also relates to the field of therapy for fibrotic disease, based on such prognoses, monitoring and stratification results, such as in monitoring and/or stratifying and/or treating patients having a higher likelihood of rapid fibrotic disease progression.

BACKGROUND TO THE INVENTION

The following discussion of the background of the invention is merely provided to aid the reader in understanding the context of the invention and is not admitted to describe or constitute relevant prior art.

Molecular Diagnostics/Prognostics

Molecular diagnostic and prognostic assays detect specific sequences in nucleic acids such as DNA or RNA that are associated with disease and/or disease progression, including single nucleotide polymorphisms (SNPs), deletions, rearrangements, substitutions, and insertions. Clinical applications of molecular diagnostics are known for infectious disease, oncology, pharmacogenomics, and genetic disease susceptibility testing. Nucleic acid-based assays have become accepted in clinical diagnostics owing to their high specificity, the ease with which they can be configured to detect target sequence, their high sensitivity, and ability to be automated.

Approximately 90% of all polymorphisms in the human genome are single nuclear polymorphisms (SNPs). SNPs are defined by a single base position in the genome at which different alleles or alternative nucleotides exist in a population. A SNP may arise from a substitution of one nucleotide for another at the polymorphic site. Substitutions can be transitions or transversions. A SNP may also be a single base insertion or deletion variant referred to as i.e., an indel.

SNPs may occur in coding and non-coding regions of the genome, however the association of a SNP with a particular phenotype is generally dependent on the SNP being in linkage disequilibrium with one or more genes associated with that phenotype. Causative SNPs are those SNPs that are most predictive of a possible clinical phenotype. Causative SNPs generally occur in a genetic region that influences phenotype e.g., a coding region or exon, or a non-coding region that is involved in regulating expression of a pathway or single gene, or in regulating transcript processing. Causative SNPs are preferred for diagnostic purposes by virtue of their stronger association with phenotype and improved specificity relative to non-causative SNPs. Some SNPs that are not causative SNPs may be in linkage disequilibrium with a causative SNP, such that the SNPs co-segregate. However, causative SNPs generally have a stronger association with the phenotype in question than a non-causative SNP, even though the causative and non-causative SNPs may be in the same haplogroup.

An individual may be homozygous or heterozygous for an allele at each SNP position. SNP genotypes include individual SNPs, and haplotypes i.e., groups of SNPs that are generally inherited together. Haplotypes can have stronger correlations with diseases or other phenotypic effects compared with individual SNPs, and therefore may provide increased diagnostic accuracy in some cases.

An association study of a SNP and a specific disorder involves determining the presence or frequency of the SNP allele in DNA-containing biological samples e.g., blood, serum, buccal swab, etc. from individuals with the disorder of interest, such as liver fibrosis and related pathologies and comparing the information to that of controls (i.e., individuals who do not have the disorder; controls may be also referred to as "healthy" or "normal" individuals) who are preferably of similar age and race. The appropriate selection of patients and controls is important to the success of SNP association studies. Therefore, a pool of individuals with well-characterized phenotypes is extremely desirable.

Molecular diagnostic tests for detection of SNPs generally comprise detecting target nucleic acid that is associated with a particular disease or disease progression from a patient sample, such as by amplifying the nucleic acid from blood, serum, buccal swab, etc., e.g., using an art-recognized real-time polymerase chain reaction (PCR) or isothermal nucleic acid sequence-based amplification assays (NASBA) or oligonucleotide ligation-PCR assay, and then detecting the amplified nucleic acid using a suitable read-out. For example, a labeled detection probe may be hybridized to an amplified target, and the amount of bound label determined. The label may be selected according to the detection chemistry of choice, and optical detection methods e.g., fluorescence, chemiluminescence, or enzyme-substrate colorimetry, are generally preferred. End products of amplification reactions are often detected by either gel or capillary electrophoresis. To overcome the low throughput limitation of electrophoresis, amplification chemistries have been coupled to high-throughput detection platforms such as flow cytometry, microarrays, or reverse line blot hybridization.

Molecular diagnostic assay formats may be single-plex assays that detect a single diagnostic marker, or alternatively, they may be multiplexed to detect multiple diagnostic markers simultaneously. Multiplexing can occur by modifying assay chemistry and/or signal detection and/or data processing. For example, multiplex amplification generally involves the design and use of compatible primer sets for each diagnostic marker assayed. Optical detection methods can be multiplexed by running parallel assays to detect multiple signals simultaneously in single samples or, in the case of small-scale multiplexing by employing different labels for each nucleotide variant at each SNP locus assayed. DNA-modified silica nanoparticles (SiNPs) may be employed to capture an end-product of an amplification reaction or primer extension reaction. Alternatively, optically encoded fluorophore-doped microspheres (isotropic microspheres), or anisotropic particles that are encoded optically and by shape and/or size and/or composition, e.g., Raman dye-labeled particles, quantum dot barcodes, notched silicon particles, metal nanowires, Illumina Veracodes, oblong dot-coded particles and magnetic barcoded hydrogel microparticles, permit a high degree of multiplexing. Such particles are detectable by any one of a variety of methods including optical microscopy, Raman spectroscopy, and flow cytometry. Alternatively, the degree of multiplexing may be enhanced by employing nanostructures, e.g., gold nanoparticle, grapheme, carbon nanotube, coordination polymer colloid, or a poly(p-phenylenediamine) nanobelt, each nanostructure being labeled with a different fluorescent dye adsorbed onto a different single-stranded nucleic acid probe to provide a quenched signal that releases fluorescence when bound to the target sequence.

Alternatively, or in addition to employing amplification chemistry, sequence modifications in nucleic acid can be detected directly by sequence analysis e.g., minisequencing or microsequencing or Next Generation sequencing. Minisequencing has particular application in SNP genotyping tests. Minisequencing employs DNA polymerase-mediated extension, e.g., using thermostable DNA-polymerase, of a primer by a single base that detects a specific SNP, wherein an oligonucleotide-tagged primer (tag) anneals directly upstream of the SNP site of interest in the sample DNA and is extended enzymatically by a single biotin-labeled chain-terminating dideoxynucleotidetriphosphate (ddNTP). The ddNTP or the primers are generally labeled e.g., using streptavidin-phycoerythrin or other fluorophore, or a dye, SiNP, microsphere, isotropic microsphere or anisotropic particle, to permit their detection. The extended and labeled primers may be captured onto microspheres via hybridization of the tags to complementary oligonucleotides (anti-tags) that have been conjugated to the microspheres. The labeled primers are then analyzed. For example, fluorescent primers and SiNP-bound primers may be analyzed by flow cytometry. Such assays are multiplexed using commercially available arrays of different labels to permit simultaneous interrogation of multiple SNPs in a single sample. A particular advantage of this chemistry is that it permits identification of heterozygotes and homozygotes, because a set of four multiplex reactions, each for a different base (A, C, T and G), may be performed for each allele being interrogated. Multiplex minisequencing may also be performed using microarrays, wherein single-base extended probes are captured onto a solid surface e.g., a microscope slide, which is then scanned to detect the label. The minisequencing reactions generally occur in solution before being hybridized to the microarray. Minisequencing with microarrays generally offers higher multiplexity than using microspheres, however the hybridization and readout processes are generally slower and have lower throughput than flow cytometry. In a slight variation, four-color minisequencing or single-base extension (SBE) proceeds on a microarray having the amplified product already bound on its surface via a hybridization reaction.

Signals in the foregoing molecular assays may also be amplified e.g., by performing detection and then amplifying the detection/signal probe, while the target remains at the original concentration. Signal amplification techniques e.g., multiplex ligase-dependent probe amplification (MLPA) or multiplex oligonucleotide ligation-PCR (MOL-PCR) have been developed to facilitate diagnosis of genetic disease or to detect diagnostic signatures. Such signal amplification assays are commonly based on sequencing or hybridization chemistries. MLPA is based on the hybridization of a pair of probes adjacent to each other on a target sequence, followed by their ligation to yield a single-stranded stretch (the signal) that can be amplified using labeled primers. Multiple probe pairs are ligated in a single reaction tube and amplified simultaneously to provide a multiplex assay format. Detection of the amplified product(s) is then performed using art-recognized procedures. MLPA is suitable for assaying SNPs, indels and repeats, because the assay chemistry requires only that the target-specific regions of the probe pairs recognize a target and are successfully ligated. In a similar approach, MOL-PCR is used to type SNPs. In MOL-PCR, probe pairs are designed to hybridize at the SNP site(s), such that each probe pair detects an alternative SNP base thereby discriminating between the different SNPs.

In general, assays that detect the presence or absence of one or more specific alleles are qualitative, and do not require the degree of refinement necessary for quantitative testing.

Fibrosis

Fibroproliferative diseases, including pulmonary fibrosis, systemic sclerosis, liver cirrhosis, cardiovascular disease, progressive kidney disease, and macular degeneration, are a leading cause of morbidity and mortality. Fibrosis can affect all tissues and organ systems, and fibrotic tissue remodeling can also influence cancer metastasis and accelerate chronic graft rejection in transplant recipients. In general, fibrosis involves the replacement of parenchymal tissue with connective tissue, leading to substantial remodeling of the extracellular matrix (ECM) components involving excessive deposition of fibronectin and type I collagen, and formation of permanent scar tissue, and ultimately to organ failure and death. Typically, fibrosis results from a chronic inflammatory reaction that persists for several weeks or months, wherein inflammation, tissue destruction, and repair processes may occur simultaneously. Most chronic fibrotic disorders involve a persistent causative agent or irritant that sustains the production of growth factors, proteolytic enzymes, angiogenic factors, and fibrogenic cytokines, which together stimulate the deposition of connective tissue elements that progressively remodel and destroy normal tissue architecture.

The fibrotic diseases encompass a wide spectrum of clinical entities, including multisystemic diseases such as systemic sclerosis, multifocal fibrosclerosis, sclerodermatous graft-versus-host disease in bone marrow transplant recipients, nephrogenic systemic fibrosis, as well as organ-specific fibroses of the lung (pulmonary fibroses such as idiopathic pulmonary fibrosis or progressive massive fibrosis), liver, kidney, heart (e.g., endomyocardial fibrosis), soft tissue of the mediastinum (e.g., mediastinal fibrosis), intestine (e.g., in Crohn's Disease), joints (e.g., arthrofibrosis, adhesive capsulitis), skin (e.g., scleroderma, or keloid), soft tissue of the retroperitoneum (e.g., retroperitoneal fibrosis), or bone marrow (e.g., myelofibrosis). Fibrosis is associated with numerous diseases and medical indications.

For example, hepatic fibrosis arises in patients suffering from autoimmune disease, metabolic liver disease, diseases with secondary involvement of the liver, α1-antitrypsin deficiency, Wilson disease, fructosemia, galactosemia, glycogen storage diseases, hemochromatosis, Gaucher disease, Zellweger syndrome, tyrosinemia, congenital hepatic fibrosis, brucellosis, echinococcosis, chronic hepatitis B virus infection, chronic hepatitis C virus infection, non-alcoholic steatohepatitis (NASH), primary biliary cirrhosis, primary sclerosing cholangitis, reduced hepatic blood flow, Budd-Chiari syndrome, heart failure, hepatic veno-occlusive disease, portal vein thrombosis, hepatocellular carcinoma, alcohol toxicity, amiodarone toxicity, chlorpromazine toxicity, isoniazid toxicity, methotrexate toxicity, methyldopa toxicity, oxyphenisatin toxicity, tolbutamide toxicity, scarring due to prior liver surgery, or bile duct strictures due to impacted gallstones.

In another example, renal fibrosis generally arises in patients suffering from diabetic nephropathy and/or chronic renal failure, and especially in diabetic patients with diabetic renal disease, hyperglycemia, a microvascular complication of diabetes, a macrovascular complication of diabetes, retinopathy, or nephropathy. A high degree of interstitial fibrosis is a strong predictor of decline in glomerular filtration rate (GFR) and progression to chronic kidney disease. Late-stage chronic CS-A nephrotoxicity may be induced by immune suppressant therapy e.g., involving administration of cimetidine, ranitidine, diltiazem, verapamil, erythromycin, metoclopramide, anabolic steroids or oral contraceptives.

In another example, peritoneal fibrosis arises in patients undergoing long-term peritoneal dialysis as a renal replacement therapy such as for chronic kidney disease or diabetes. In keeping with fibrogenesis in many other organs, peritoneal fibrosis recapitulates the role of elevated TGF-β1 in fibrogenesis in the peritoneal cavity, at least in animal models. For example, TGF-β1 is expressed at high concentrations in the effluent of peritoneal dialysis patients in response to dialysis and during infection, and mesothelial cells exposed to TGF-β1 in vitro exhibit pro-fibrotic changes. Idiopathic pulmonary fibrosis is common in patients suffering from interstitial pneumonia.

In another example, pulmonary fibrosis is associated with many diseases and irritants, including rheumatoid arthritis, scleroderma, systemic lupus erythematosis (SLE), mineral dusts such as coal, silicon, asbestos (asbestosis), metals, poisonous industrial gases such as chlorine and sulphur dioxide, radiation therapy, poisons such as paraquat, and medications such as nitrofurantoin, amiodarone, bleomycin, cyclophosphamide and methotrexate.

Notwithstanding the numerous diseases and body organs in which fibrosis may occur, there is basis for a common etiology.

For example, the transforming growth factor-β (TGF-β)-mediated epithelial-mesenchymal transition (EMT) may play a universal role in fibrosis, no matter the underlying disease etiology. Transforming growth factor-β (TGF-β) induces EMT in alveolar epithelial cells (AEC) in vitro and in vivo, and epithelial and mesenchymal markers have been co-localized to hyperplastic type II (AT2) cells in lung tissue from patients with idiopathic pulmonary fibrosis (IPF). TGF-β is also known to induce EMT in normal mammary epithelial cells and in a number of different epithelial cells in vitro, including renal proximal tubular, lens, and alveolar epithelial cells. TGF-β is also increased in fibrotic organs, such as those in lungs of patients with idiopathic pulmonary fibrosis, or in kidneys of chronic kidney disease patients. Moreover, the expression of active TGF-β in lungs or kidneys of rats induces a dramatic fibrotic response, whereas an inability to respond to TGF-β affords protection from bleomycin-induced fibrosis or renal interstitial fibrosis. TGF-β is believed to contribute to the development of fibrosis by stimulating the synthesis of ECM molecules, activating fibroblasts to α-smooth muscle actin (α-SMA)-expressing myofibroblasts by inducing expression of the ED-A variant of fibronectin (ED-A FN) that is required for enhancement of α-SMA and collagen type I expression in fibrosis, and down-regulating matrix metalloproteinases (MMPs). Connective tissue growth factor (CTGF) has also been implicated to be involved in fibrotic diseases, as a downstream mediator of the effects of TGF-β on fibroblasts.

There is also evidence that the apoptotic pathway is involved in the pathogenesis of fibrosis. For example, the lungs of patients suffering from IPF exhibit elevated epithelial apoptosis and decreased apoptosis of myofibroblasts, and blockade of epithelial cell apoptosis in vitro can prevent collagen deposition. See e.g., Uhal, *Eur. Respir. Rev.* 17(109), 138-144, 2008. Similarly, in a sub-total nephrectomy model of chronic kidney disease, a time-dependent increase in apoptosis and PCNA antigen-positive staining is correlated with the progression of renal fibrosis, suggesting that apoptosis contributes to the progression of tubular atrophy and pathogenesis of tubulo-interstitial scarring. See e.g., Thomas et al., *Nephrol. Dial. Transplant.* 13(9), 2216-2226, 1998. Apoptotic injury also participates in hepatic fibrosis and, notwithstanding that the molecular mechanisms involved are not well understood, induction of tissue inhibitor of metalloproteinase-1 (TIMP-1) appears to be involved the pathogenesis of hepatic apoptosis-fibrosis, because inhibition of TIMP-1 using a pan-caspase inhibitor or TIMP1-siRNA or c-Jun siRNA reduces the fibrotic response and expression of the fibrosis-related genes aSMA, CTGF, and TGF-β2R. See e.g., Wang et al., *Apoptosis* 18(5), 566-577, 2013.

Clinical diagnosis and staging of fibrosis may be non-invasive, employing imaging technology such as ultrasonography, magnetic resonance (MR) imaging or ultrasonic elasticity imaging. For example, transient elastography measures the stiffness value of tissue such as liver, and shows different stages by different range of values. However, the gold standard requires invasive tissue biopsy and pathology slide review. Biopsies take a long time for the patient to recover, and results may be compromised by sample deviation. Imaging is a high-cost due to the need for expensive equipment and specialist interpretation of scans. Due to their comparatively low specificity and sensitivity and high cost relative to molecular diagnostics, serum biomarkers are not used widely in clinical diagnosis of fibrosis.

Staging of fibrosis assists in evaluation of disease progression, however is largely based on biopsy or imaging analyses. In general, early stage fibrosis may be considered as including a range of grades from no visible fibrotic lesions and/or a normal amount of connective tissue and without septa formation or tissue stiffening or remodelling. In contrast, late stage fibrosis involves septa formation and/or remodeling or other architectural distortion of the organ and/or end-stage fibrosis in which functionality is dramatically reduced, often indicating transplantation. There are several known systems for grading and/or staging fibrosis progression that are employed in the art. For example, the Scheuer/Batts-Ludwig/Tsui and Metavir systems, and recognized Staging 0-6 are simple, reproducible and validated clinically, e.g., for patients having chronic hepatitis due to HBV or HCV infection, autoimmune hepatitis, α1-antitrypsin deficiency, Wilsons disease, biliary disease, primary biliary cirrhosis, primary sclerosing cholangitis, chronic venous outflow obstruction, or hemochromatosis. For example, Scheuer/Batts-Ludwig/Tsui is employed extensively in USA and scores five stages: Stage 0=no visible fibrosis and a normal amount of connective tissue; Stage 1=visible portal/periportal fibrosis; Stage 2=septal fibrosis; Stage 3=bridging fibrosis with architectural distortion; and Stage 4=probable end-stage fibrosis or cirrhosis. The Metavir scoring criteria are used extensively in Europe, especially France, and as similar to Scheuer/Batts-Ludwig/Tsui: F0=no visible fibrosis; F1=portal fibrosis without septa; F2=portal fibrosis with rare septa; F3=numerous septa without end-stage fibrosis or cirrhosis; and F4=probable end-stage fibrosis or cirrhosis. Staging 0-6 is typically not used in a clinical setting due to its complexity, however it is employed in clinical trials: Stage 0=no visible fibrosis; Stage 1=expansion of some portal areas with or without septa; Stage 2=expansion of most portal areas with or without septa;

Stage 3=expansion of most portal areas with occasional portal to portal bridging; Stage 4=expansion of portal areas with marked bridging (portal-portal and/or portal-central); Stage 5=marked bridging with occasional nodules (incomplete cirrhosis); and Stage 6=probable or definitive end-stage fibrosis or cirrhosis. Variations of these staging systems, that account for early stage sinusoidal foci or extensive sinusoidal fibrosis prior to development of portal/periportal fibrosis, have also been employed in diagnosis of fibrosis in NASH patients (see e.g., Kleiner et al, *Hepatol.* 41, 1313-1321, 2005.

In contrast to the relatively detailed mechanistic knowledge of the regulatory pathways that are involved in fibrogenesis, the switches that control susceptibility to fibrosis, the intensity of fibrogenesis, and the speed at which fibrosis progresses are not well-understood. The role of genetic variation in susceptibility to fibrosis (onset) and/or progression of fibrosis has not been well described, however it is apparent that variations in the time-course of fibrosis in different disease indications may vary considerably between individuals. For example, symptoms of renal fibrosis, pulmonary fibrosis including IPF, and hepatic fibrosis may develop slowly over a time-period of months to several years in some patients, but more rapidly in others. See e.g., Collard et al., *Am. J. Respir. Crit. Care Med.* 176, 636-643, 2007; Hyzy et al., *Chest* 132, 1652-1658, 2007; Martinez et al., *Ann Intern Med* 142, 963-967, 2005; Poynard et al., *J. Hepatol.* 34, 730-739, 2001. Strain-specific variations in fibrogenic responses to TGF-β1 in an animal model of peritoneal fibrosis also suggest an underlying genetic component to the risk of scarring in the peritoneum.

Several genetic polymorphisms influencing the onset and/or progression of fibrosis have been identified in patients with HCV infection, autoimmune chronic cholestasis, alcohol-induced liver diseases, NASH, idiopathic pulmonary fibrosis and scleroderma lung fibrosis. These include associations in genes encoding immunoregulatory proteins, proinflammatory cytokines, fibrogenic factors, host defense proteins, cell-cell adhesion molecules and DNA repair enzymes. For example, SNPs have been identified that are linked to or within genes encoding TGF, TGF-β1, interleukin-1 receptor (IL-1R) antagonist, IL-6/TNF receptor II (TNFR-II), angiotensin (AT), alcohol dehydrogenase (ADH2), interleukin (IL)-1β, microsomal triglyceride transfer protein (MTP), patatin-like phospholipase domain-containing 3 (PNPLA3) protein, and in the hemochromatosis (HFE) gene. See e.g., Bernard et al., *Diabetologia* 43(8), 995-999, 2000; Grutters et al., *Eur Respir. J.* 25, 915-927, 2005; Powell et al., *Hepatology* 31(4), 828-833, 2000; Romeo et al., *Curr. Opin. Lipidol.* 21, 247-252, 2010; Smith et al., *Hepatology.* 27(6), 1695-1999, 1998; Tanaka et al., *J. Infec. Dis.* 187(11), 1822-1825, 2003; and Yamauchi et al., *J. Hepatology* 23(5), 519-523, 1995. For various reasons, these markers have not currently been integrated into clinical practice. See e.g., Bataller et al., *Hepatology* 37(3), 493-503, 2003. For example, the absence of a mechanistic link of genetic polymorphisms to susceptibility and/or progression and/or severity of fibrosis, and associations that are not sufficiently strong to suggest that the identified SNPs are causative, limit their application in clinical practice. The identification of the SNPs that have a strong mechanistic link with susceptibility and progression of fibrosis and patient survival, and/or that have sufficiently high associations with phenotype to suggest that they are causative SNPs with respect to fibrosis susceptibility and/or severity and/or progression, will provide a basis for focused or tailored therapies by identifying those patients at significant risk of disease and/or disease progression at an early stage and tailoring their treatment accordingly.

SUMMARY OF THE INVENTION

In work leading up the present invention, the inventors sought to identify genetic polymorphisms that have a strong mechanistic link with susceptibility and/or severity and/or progression of fibrosis, and/or patient survival in different disease contexts, including hepatic fibrosis such as in patient cohorts having a chronic HBV or HCV infection or NASH, NAFLD, intestinal fibrosis such as in patient cohorts having Chrohn's Disease, and renal fibrosis such as in patient cohorts having chronic kidney disease. The inventors were especially interested in identifying one or more SNPs associated with susceptibility and/or severity and/or progression of fibrosis, and/or patient survival, that have utility in clinical practice, e.g., one or more causative SNPs.

Using a cohort of 1000 subjects with chronic hepatitis C (CHC), the inventors identified specific combinations of specific polymorphisms in or at least linked to two genes, namely IL28B (syn. Interferon lambda 3; IFNL3) and c-Mer proto-oncogene tyrosine kinase (MERTK), that have strong predictive capacity for determining a likelihood of fibrosis onset (susceptibility) and/or severity and/or progression of fibrosis. This is also identified at least in three other fibrotic diseases including chronic hepatitis B virus infection, non-alcoholic steatohepatitis (NASH) and NAFLD. As exemplified herein, the inventors have demonstrated that single nuclear polymorphism (SNP) genotypes in or at least linked to both the human IL28B gene and the human MERTK gene discriminate between patients having no fibrosis or early stage fibrosis and patients having more advance or late stage or end-stage fibrosis. For example, in patients who have a chronic HCV infection, genotyping assays configured to discriminate between combinations of different genotypes in the human IL28B SNP loci rs12979860 and/or rs8099917, and between different genotypes in the human MERTK SNP loci rs10211152 and/or rs4374383 and/or rs17175626 and/or rs6748256 provide a strong correlation with susceptibility and/or severity of fibrosis and/or progression of fibrosis, that is more than a merely additive effect of the individual loci tested (O.R.>4.0; p<0.01). See e.g., FIG. 1. The inventors also confirmed that different genotypes in the combination of human IL28B SNP loci rs12979860 and the human MERTK SNP loci rs10211152 provide a strong correlation with susceptibility and/or severity of fibrosis and/or progression of fibrosis in a replication cohort of patients suffering from chronic HCV infection, that the predictive capacity of these two SNP loci is more than a merely additive effect of the individual loci tested (O.R.>6.4; p<0.001).

In contrast to the combined predictive value of rs12979860 and/or rs8099917 with rs10211152 and/or rs4374383 and/or rs17175626 and/or rs6748256, the bulk of SNP combinations tested within or at least linked to the IL28B and MERTK genes are not correlated strongly to susceptibility and/or severity and/or progression of fibrosis. For example, combinations of the IL28B SNP rs12979860 with any one of the MERTK SNPs rs11685190, rs13404771, rs2230515, rs10185747, rs10195619, rs10496440, rs13016143, or rs9937047 do not provide such a strong correlation to susceptibility and/or severity and/or progression of fibrosis (O.R.<4.0; p<0.001). Similarly, combinations of the MERTK SNP rs4374383 with any one of the IL28B SNPs rs1297980275, rs1503391, rs17461620, rs1931704, rs2066911, rs3033390, rs926494, rs557905, rs6806020 or rs7512595 do not provide such a strong correlation to susceptibility and/or severity and/or progression of fibrosis (O.R.<4.0; p<0.001). These data indicate that the specific SNP combinations linked to IL28B and MERTK genes that have been identified by the present inventors are specific and, in view of their combined strong non-additive correlation to fibrosis susceptibility and/or severity and/or progression, may be causative alleles. Without being bound by any theory or mode of action, the correlations in IL28B and MERTK SNPs suggests a strong mechanistic link with the role of apoptosis in susceptibility and progression of fibrosis. For example, the IL28B gene produces interferon lambda (IFNλ), which signals through a janus kinase-signal transducer and activator of transcription (JAK-STAT) pathway activating interferon-sensitizing genes (ISG) such as 2',5'-oligoadenylate synthetase (OAS) and mitogen-activated protein (MAP) kinases, which are known to cause apoptosis, growth inhibition, and viral replication. The MERTK gene encodes a tyrosine kinase that functions as a major macrophage apoptotic cell (AC) receptor that enables macrophages to clear early ACs, and mediates AC clearance by CD14(bright)CD16(+) monocytes.

Also in marked contrast to the combined predictive value of rs12979860 and/or rs8099917 with rs10211152 and/or rs4374383 and/or rs17175626 and/or rs6748256, the predictive value of combinations of SNPs in or at least linked to known fibrosis genes e.g., combinations of the TULP1 and RNF7 or TULP1 and PNPLA3 or PNPLA3 and RNF7 is much weaker O.R.<2.0; p>0.07).

The inventors have also demonstrated that the predictive value of combined SNP alleles in or least linked to IL28B and MERTK genes may be enhanced by specific polymorphisms in the RNF7 genes of humans, especially the human RNF7 locus rs16851720 (O.R. 8.16; p<0.0001). The SNP rs16851720 is located within or linked to the RNF7 gene, which encodes an antioxidant that protects against apoptosis, supporting the possible strong mechanistic link of the associations described herein with the role of apoptosis in susceptibility and/or severity and/or progression of fibrosis. In contrast to the strong enhancement of the predictive value of SNPs in or linked to each of IL28B and MERTK by including SNP alleles within or linked to the RNF7 gene, only a marginal and additive enhancement of predictive value is obtained by combining SNP alleles of the fibrosis genes TULP1 or PNPLA3 with the combined SNPs in or linked to each of IL28B and MERTK (O.R. 4.69-5.02; p<0.01).

The data provided herein indicate that combinations of specific SNPs in or linked to both IL28B and MERTK, optionally in further combination with the RNF7 SNP rs16851720, provide a basis for predicting susceptibility and/or severity and/or progression and/or progression rate in a clinical context.

Accordingly, the present invention provides a method of determining a likelihood that a subject having a medical condition associated with onset or progression of fibrosis is predisposed to developing fibrosis or is predisposed to progressing to a particular stage of fibrosis or is predisposed to a rapid progression of fibrosis, the method comprising performing one or more genotyping assays on a DNA-containing sample obtained from the subject, wherein the one or more assays are configured to discriminate single nuclear polymorphism (SNP) genotypes in or at least linked to both the human IL28B gene and the human MERTK gene, wherein the SNPs are selected from rs12979860, rs8099917, rs10211152 and rs4374383, a SNP in linkage disequilibrium with rs12979860, a SNP in linkage disequilibrium with rs8099917, a SNP in linkage disequilibrium with rs10211152 and a SNP in linkage disequilibrium with rs4374383, wherein the assay results indicate a likelihood that the subject will develop fibrosis and/or progress to a particular stage of fibrosis and/or progress rapidly to a late-stage fibrosis.

In one example, a SNP in linkage disequilibrium with rs10211152 may be a SNP in the MERTK gene selected from the group consisting of rs10165940, rs10168067, rs10205793, rs13387346, rs13402707, rs13416895, rs2230517, rs6723289, rs6723394, rs6735717 and rs13396030. For example, SNP in linkage disequilibrium with rs10211152 may be rs10165940. For example, SNP in linkage disequilibrium with rs10211152 may be rs10168067. For example, SNP in linkage disequilibrium with rs10211152 may be rs10205793. For example, SNP in linkage disequilibrium with rs10211152 may be rs13387346. For example, SNP in linkage disequilibrium with rs10211152 may be rs13402707. For example, SNP in linkage disequilibrium with rs10211152 may be rs13416895. For example, SNP in linkage disequilibrium with rs10211152 may be rs2230517. For example, SNP in linkage disequilibrium with rs10211152 may be rs6723289. For example, SNP in linkage disequilibrium with rs10211152 may be rs6723394. For example, SNP in linkage disequilibrium with rs10211152 may be rs6735717. For example, SNP in linkage disequilibrium with rs10211152 may be rs13396030.

Accordingly, in one example, the method may comprise:
(a) performing the one or more genotyping assays configured to discriminate between different genotypes in the human IL28B gene and the human MERTK gene, wherein the genotypes in the human IL28B gene are in the SNP rs12979860 and/or the SNP rs8099917, and wherein the genotypes in the human MERTK gene are in the SNP rs10211152 and/or a SNP in the MERTK gene in linkage disequilibrium with rs10211152 selected from the group consisting of rs10165940, rs10168067, rs10205793, rs13387346, rs13402707, rs13416895, rs2230517, rs6723289, rs6723394, rs6735717 and rs13396030; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
  (i) a CC genotype in rs12979860 and/or a TT genotype in rs8099917; and
  (ii) a CC genotype in rs10211152 and/or a GG genotype in rs10165940 and/or a CC genotype in rs10168067 and/or a GG genotype in rs10205793 and/or a CC genotype in rs13387346 and/or a CC genotype in rs13402707 and/or a CC genotype in rs13416895 and/or a GG genotype in rs2230517 and/or a CC genotype in rs6723289 and/or a CC genotype in rs6723394 and/or a AA genotype in rs6735717 and/or a GG genotype in rs13396030.

The present invention also provides a method of determining a likelihood that a subject having a medical condition associated with onset or progression of fibrosis will develop fibrosis and/or progress to a particular stage of fibrosis and/or progress rapidly to a late-stage fibrosis, said method comprising:
(a) performing one or more genotyping assays on a DNA-containing sample obtained from the subject, wherein the one or more assays are configured to discriminate between different genotypes in or at least linked to both the human IL28B gene and the human MERTK gene, wherein the genotypes in or at least linked to the human IL28B gene are alleles of a single nuclear polymorphism (SNP) selected from rs12979860, rs8099917, an allele of a SNP in linkage disequilibrium with rs12979860, and an allele of a SNP in linkage disequilibrium with rs8099917, and wherein the genotypes in or at least linked to the human MERTK gene are alleles of a SNP selected from rs10211152, rs4374383, a SNP in linkage disequilibrium with rs10211152 and a SNP in linkage disequilibrium with rs4374383; and (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:

(i) a CC genotype in rs12979860 and/or a TT genotype in rs8099917 and/or a genotype in linkage disequilibrium with said CC genotype or TT genotype; and (ii) a CC genotype in rs10211152 and/or an AG genotype or GG genotype in rs4374383 and/or genotype in linkage disequilibrium with said CC genotype or AG genotype or GG genotype, thereby determining a likelihood that the subject will develop fibrosis and/or progress to a particular stage of fibrosis and/or progress rapidly to a late-stage fibrosis.

In one example, the method may comprise:
(a) performing the one or more genotyping assays configured to discriminate between different genotypes in the human IL28B gene and the human MERTK gene, wherein the genotypes in the human IL28B gene are in the SNP rs12979860 and/or the SNP rs8099917, and wherein the genotypes in the human MERTK gene are in the SNP rs10211152 and/or the SNP rs4374383; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a CC genotype in rs12979860 and/or a TT genotype in rs8099917; and
(ii) a CC genotype in rs10211152 and/or an AG genotype or GG genotype in rs4374383.

In one example, the method may comprise:
(a) performing the one or more genotyping assays configured to discriminate between different genotypes in the human IL28B gene and the human MERTK gene, wherein the genotypes in the human IL28B gene are in the SNP rs12979860, and wherein the genotypes in the human MERTK gene are in the SNP rs10211152; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a CC genotype in rs12979860; and
(ii) a CC genotype in rs10211152.

In one example, the method may comprise:
(a) performing the one or more genotyping assays configured to discriminate between different genotypes in the human IL28B gene and the human MERTK gene, wherein the genotypes in the human IL28B gene are in the SNP rs12979860, and wherein the genotypes in the human MERTK gene are in the SNP rs4374383; and (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a CC genotype in rs12979860; and
(ii) an AG genotype or GG genotype in rs4374383.

In one example, the method may comprise:
(a) performing the one or more genotyping assays configured to discriminate between different genotypes in the human IL28B gene and the human MERTK gene, wherein the genotypes in the human IL28B gene are in the SNP rs8099917, and wherein the genotypes in the human MERTK gene are in the SNP rs10211152; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a TT genotype in rs8099917; and
(ii) a CC genotype in rs10211152.

In one example, the method may comprise:
(a) performing the one or more genotyping assays, wherein the genotypes in the human IL28B gene are in the SNP rs8099917, and wherein the genotypes in the human MERTK gene are in the SNP rs4374383; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a TT genotype in rs8099917; and
(ii) an AG genotype or GG genotype in rs4374383.

In one example, performing one or more genotyping assays on the DNA-containing sample comprises performing the genotyping assays under conditions that discriminate between the following combinations of genotypes in the sample DNA:
(a) between homozygotes (CC), heterozygotes (CT) and alternate homozygotes (TT) at rs12979860 and/or between homozygotes (TT), heterozygotes (TG) and alternate homozygotes (GG) at rs8099917; and
(b) between homozygotes (CC), heterozygotes (CT) and alternate homozygotes (TT) at rs10211152 and/or between homozygotes (GG), heterozygotes (AG) and alternate homozygotes (AA) at rs4374383.

In any example hereof where the method comprises discriminating between different genotypes for a SNP in the MERTK gene in linkage disequilibrium with rs10211152, the method may comprise performing one or more genotyping assays under conditions that discriminate between the following combinations of genotypes in the sample DNA between homozygotes (GG), heterozygotes (AG) and alternate homozygotes (AA) at rs10165940 and/or between homozygotes (CC), heterozygotes (CG) and alternate homozygotes (CC) at rs10168067 and/or between homozygotes (GG), heterozygotes (AG) and alternate homozygotes (AA) at rs10205793 and/or between homozygotes (CC), heterozygotes (CT) and alternate homozygotes (TT) at rs13387346 and/or between homozygotes (CC), heterozygotes (CT) and alternate homozygotes (TT) at rs13402707 and/or between homozygotes (CC), heterozygotes (CG) and alternate homozygotes (GG) at rs13416895 and/or between homozygotes (GG), heterozygotes (AG) and alternate homozygotes (AA) at rs2230517 and/or between homozygotes (CC), heterozygotes (CA) and alternate homozygotes (AA) at rs6723289 and/or between homozygotes (CC), heterozygotes (CT) and alternate homozygotes (TT) at rs6723394 and/or between homozygotes (AA), heterozygotes (AG) and alternate homozygotes (GG) at rs6735717 and/or between homozygotes (GG), heterozygotes (AG) and alternate homozygotes (AA) at rs13396030.

In another example, a SNP in linkage disequilibrium with rs10211152 may be selected from the group consisting of rs17175626 and rs6748256. For example, SNP in linkage disequilibrium with rs10211152 may be rs17175626. For example, SNP in linkage disequilibrium with rs10211152 may be rs6748256.

In one example, a SNP in linkage disequilibrium with rs4374383 may be selected from the group consisting of rs17175626 and rs6748256.

In any of the methods disclosed herein, the method may further comprise performing one or more additional genotyping assays on the DNA-containing sample obtained from the subject which is/are configured to discriminate single nuclear polymorphism (SNP) genotypes in or at least linked to the human RNF7 gene, wherein the SNPs are selected from rs16851720 and a SNP in linkage disequilibrium with rs16851720. For example, the method may comprise performing one or more additional genotyping assays on the DNA-containing sample obtained from the subject configured to discriminate between alleles at the SNP rs16851720, and wherein detection of an AA genotype in rs16851720 in combination with the SNPs in both the IL28B and MERTK genes indicates a strong likelihood that the subject will develop fibrosis and/or progress rapidly to a late-stage fibrosis.

In any of the methods disclosed herein, the one or more assays configured to discriminate SNP genotypes may comprise PCR assays and/or real-time PCR assays and/or minisequencing assays and/or next generation sequencing assays and/or isothermal nucleic acid sequence-based amplification assays (NASBA) and/or oligonucleotide ligation-PCR assays.

In any of the methods disclosed herein, the one or more assays configured to discriminate SNP genotypes may comprise multiplex assays for simultaneous discrimination between the SNPs in or at least linked to both the IL28B and MERTK genes or for simultaneous discrimination between the SNPs in or at least linked to the IL28B and MERTK and RNF7 genes.

In any of the methods described herein, the combined SNP genotypes in the human IL28B gene and the human MERTK gene and the human RNF7 gene provide a stronger likelihood that a subject is predisposed to a rapid progression of fibrosis than a likelihood obtained by adding the separate effect of each of said genotypes.

In any of the methods disclosed herein, the method may further comprise a first step of providing a kit comprising nucleic acids that discriminate between different genotypes in the human IL28B and the human MERTK gene and the human RNF7 gene of the sample DNA, and then performing the one or more genotyping assays employing those nucleic acids.

In one example of the methods disclosed herein, the fibrosis is liver fibrosis.

In another example of the methods disclosed herein, the fibrosis is intestinal fibrosis.

In another example of the methods disclosed herein, the fibrosis is kidney fibrosis.

In yet another example of the methods disclosed herein, the fibrosis is cardiac fibrosis.

In any of the methods disclosed herein, the subject may have a medical condition associated with progression of fibrosis selected from the group consisting of an autoimmune disease, a metabolic liver disease, a disease with secondary involvement of the liver, α1-antitrypsin deficiency, Wilson disease, fructosemia, galactosemia, a glycogen storage disease, hemochromatosis, Gaucher disease, Zellweger syndrome, tyrosinemia, a congenital hepatic fibrosis, brucellosis, echinococcosis, chronic hepatitis B, chronic hepatitis C, non-alcoholic steatohepatitis (NASH), non-alcoholic fatty liver disease (NAFLD), primary biliary cirrhosis, primary sclerosing cholangitis, reduced hepatic blood flow, Budd-Chiari syndrome, heart failure, hepatic veno-occlusive disease, portal vein thrombosis, hepatocellular carcinoma, alcohol toxicity, amiodarone toxicity, chlorpromazine toxicity, isoniazid toxicity, methotrexate toxicity, methyldopa toxicity, oxyphenisatin toxicity, tolbutamide toxicity, scarring due to prior liver surgery, bile duct strictures due to impacted gallstones, diabetes, diabetic renal disease, hyperglycemia, a microvascular complication of diabetes, a macrovascular complication of diabetes, retinopathy, nephropathy, cardiomyopathy, peripheral vascular disease, a cerebrovascular disorder, atherosclerosis. and Chrohn's disease.

For example, the subject may have a medical condition associated with progression of liver fibrosis such as chronic hepatitis B infection or chronic hepatitis C infection or non-alcoholic fatty liver disease (NAFLD) or non-alcoholic steatohepatitis (NASH), or has a medical condition associated with progression of renal fibrosis such diabetes or diabetic renal disease, or has a medical condition associated with intestinal fibrosis such as Chrohn's disease, or has a condition associated with pulmonary fibrosis such as IPF.

The present invention also provides a method of treating a subject for fibrosis or for a medical condition associated with progression of fibrosis, said method comprising:
(a) determining a likelihood that a subject having no visible fibrosis or early signs of fibrosis is predisposed to developing fibrosis or is predisposed to progressing to a particular stage of fibrosis or is predisposed to a rapid progression of fibrosis by performing a method as disclosed herein on a DNA-containing sample obtained from the subject to thereby determine a likelihood that the subject will develop fibrosis which will progress rapidly to a late-stage fibrosis; and
(b) treating the fibrosis and/or the medical condition in a subject having a strong likelihood of developing fibrosis or progressing rapidly to a late-stage fibrosis.

The present invention also provides a method of treating a subject for fibrosis or for a medical condition associated with progression of fibrosis, said method comprising:
(a) (i) receiving a test result obtained by performing a method of determining a likelihood that the subject having a medical condition associated with onset or progression of fibrosis is predisposed to developing fibrosis or is predisposed to progressing to a particular stage of fibrosis or is predisposed to a rapid progression of fibrosis in accordance with a method disclosed herein, wherein the test result determines that fibrosis has developed in the subject or that there is a strong likelihood that fibrosis will develop or progress to a late fibrosis or progress rapidly to a late-stage fibrosis in the subject; or (ii) receiving an indication or recommendation to treat a subject for the fibrosis or the medical condition based on a test result obtained by performing a method of determining a likelihood that the subject having a medical condition associated with onset or progression of fibrosis is predisposed to developing fibrosis or is predisposed to progressing to a particular stage of fibrosis or is predisposed to a rapid progression of fibrosis in accordance with a method disclosed herein, wherein the test result determines that fibrosis has developed in the subject or that there a strong likelihood that the subject is susceptible to fibrosis and/or that fibrosis will progress rapidly to a late-stage in the subject; and (b) treating a subject for the fibrosis and/or the medical condition based on the test result or indication or recommendation.

In one example, the method of treating a subject for fibrosis or for a medical condition associated with progression of fibrosis further comprises a first step of forwarding a DNA-containing sample obtained from a subject having no visible fibrosis or having early fibrosis to be analyzed by the method disclosed herein.

In one example, the subject has a medical condition associated with progression of fibrosis and treatment comprises treating the medical condition, and wherein said medical condition is selected from the group consisting of an autoimmune disease, a metabolic liver disease, a disease with secondary involvement of the liver, α1-antitrypsin deficiency, Wilson disease, fructosemia, galactosemia, a glycogen storage disease, hemochromatosis, Gaucher disease, Zellweger syndrome, tyrosinemia, a congenital hepatic fibrosis, brucellosis, echinococcosis, chronic hepatitis B, chronic hepatitis C, non-alcoholic steatohepatitis (NASH), primary biliary cirrhosis, primary sclerosing cholangitis, reduced hepatic blood flow, Budd-Chiari syndrome, heart failure, hepatic veno-occlusive disease, portal vein thrombosis, hepatocellular carcinoma, alcohol toxicity, amiodarone toxicity, chlorpromazine toxicity, isoniazid toxicity, methotrexate toxicity, methyldopa toxicity, oxyphenisatin toxicity, tolbutamide toxicity, scarring due to prior liver surgery, bile duct strictures due to impacted gallstones, diabetes, diabetic renal disease, hyperglycemia, a microvascular complication of diabetes, a macrovascular complication of diabetes, retinopathy, nephropathy, cardiomyopathy, peripheral vascular disease, a cerebrovascular disorder, atherosclerosis, and Chrohn's disease.

For example, the subject may have a medical condition associated with progression of liver fibrosis and treatment comprises treating the medical condition, and wherein said medical condition is selected from the group consisting of chronic hepatitis B infection, chronic hepatitis C infection or non-alcoholic fatty liver disease (NAFLD) and non-alcoholic steatohepatitis (NASH).

In any of the methods of treatment disclosed herein, treating the medical condition associated with progression of fibrosis may comprise administering to the subject a medicament to thereby stop the fibrosis or progression of the fibrosis and/or reverse fibrotic changes in a fibrotic tissue or fibrotic organ of the subject.

In one example, the fibrosis is liver fibrosis, such as liver fibrosis associated with a hepatitis virus infection, and treatment comprises administering an antiviral compound to a subject in need thereof. In another example, the fibrosis is liver fibrosis, and the treatment comprises removing a toxicity-causing agent or heavy metal or fatty acid from the body or body organ of a subject in need thereof. In yet another example, the fibrosis is liver fibrosis, and the treatment comprises decompressing bile ducts in a subject in need thereof.

In one example, the fibrosis to be treated is intestinal fibrosis.

In another example, the fibrosis to be treated is kidney fibrosis.

In yet another example, the fibrosis to be treated is cardiac fibrosis.

In any of the methods of treatment disclosed herein, treating the fibrosis may comprise administering to the subject a corticosteroid, penicillamine, tumour necrosis factor inhibitor (anti-TNF agent), a pan-caspase inhibitor, or other antifibrotic medicament.

The invention also provides one or more algorithms for evaluation of fibrosis and prediction of susceptibility and/or severity and/or progression and/or progression rate of fibrosis in a clinical context, including predicting a likelihood that a subject will develop fibrosis, develop to a particular stage of fibrosis or progress rapidly to late-stage fibrosis. For example, the algorithms provide coefficients for each diagnostic/prognostic marker described herein, and for age and/or gender, to arrive at a fibrosis probability index (FPS), being the likelihood that a subject will develop fibrosis or progress to a particular stage of fibrosis or progress from early-stage fibrosis to late-stage fibrosis. In another example, genotype data are combined further with one or more other parameters e.g., age and/or gender and/or AST level and/or ALT level and/or AST/ALT ratio and/or ALT/AST ratio and/or GGT level and/or bilirubin content and/or platelet count. The algorithms are for clinical application.

The present invention also provides kit for determining a likelihood that the subject having a medical condition associated with onset or progression of fibrosis is predisposed to developing fibrosis or is predisposed to progressing to a particular stage of fibrosis or is predisposed to a rapid progression of fibrosis by performing a method disclosed herein, said kit comprising two or more nucleic acids that independently discriminate between different single nuclear polymorphism (SNP) genotypes in or at least linked to the human IL28B and the human MERTK gene, wherein the SNPs are selected from rs12979860, rs8099917, rs10211152 and rs4374383, a SNP in linkage disequilibrium with rs12979860, a SNP in linkage disequilibrium with rs8099917, a SNP in linkage disequilibrium with rs10211152 and a SNP in linkage disequilibrium with rs4374383.

In one example, a SNP in linkage disequilibrium with rs10211152 may be selected from the group consisting of rs17175626 and rs6748256. For example, SNP in linkage disequilibrium with rs10211152 may be rs17175626. For example, SNP in linkage disequilibrium with rs10211152 may be rs6748256.

Alternatively, or in addition, a SNP in linkage disequilibrium with rs10211152 may be a SNP in the MERTK gene selected from the group consisting of rs10165940, rs10168067, rs10205793, rs13387346, rs13402707, rs13416895, rs2230517, rs6723289, rs6723394, rs6735717 and rs13396030. For example, SNP in linkage disequilibrium with rs10211152 may be rs10165940. For example, SNP in linkage disequilibrium with rs10211152 may be rs10168067. For example, SNP in linkage disequilibrium with rs10211152 may be rs10205793. For example, SNP in linkage disequilibrium with rs10211152 may be rs13387346. For example, SNP in linkage disequilibrium with rs10211152 may be rs13402707. For example, SNP in linkage disequilibrium with rs10211152 may be rs13416895. For example, SNP in linkage disequilibrium with rs10211152 may be rs2230517. For example, SNP in linkage disequilibrium with rs10211152 may be rs6723289. For example, SNP in linkage disequilibrium with rs10211152 may be rs6723394. For example, SNP in linkage disequilibrium with rs10211152 may be rs6735717. For example, SNP in linkage disequilibrium with rs10211152 may be rs13396030.

In one example, the kit further comprising one or more nucleic acids the discriminate between single nuclear polymorphism (SNP) genotypes in the human RNF7 gene, wherein the SNPs are selected from rs16851720 and a SNP in linkage disequilibrium with rs16851720.

In one example, the nucleic acids in the kit are for use i.e., are configured to be used, in multiplex assays for simultaneous discrimination between SNP genotypes in each of the genes.

The invention also provides a device for evaluation of fibrosis and/or fibrosis stage and/or predicting a likelihood that a subject will develop fibrosis, develop to a particular stage of fibrosis or progress rapidly to late-stage fibrosis. For example, one or more algorithms provided herein may be provided in an executable form as software, installed on a device to calculate the fibrosis probability index for any one of a number of subjects.

For example, the present invention provides a device configured to provide a diagnosis of fibrosis stage or a probability or likelihood that a subject will develop fibrosis and/or progress to a particular stage of fibrosis and/or progress rapidly to a late-stage fibrosis, wherein the device comprises:
(a) an input interface configured to receive data comprising (i) the combined IL28B/MERTK genotype of the subject determined performing the method disclosed herein, (ii) the age of the subject, and optionally (iii) the gender of the subject;
(b) a computer-readable storage medium for storing data at least for the combined IL28B/MERTK genotype or the combined IL28B/MERTK/RNF7 genotype of the subject, the age of the subject, and the gender of the subject;
(c) a data processor that is executed to calculate a prognostic score based on the stored data; and
(d) a port or readable interface for communicating the stored data and/or the prognostic score to a user.

In one example, the data processor may comprise computer-executable mathematical algorithms (1)-(3) for calculating a fibrosis probability score (FPS) that is correlated with fibrosis stage or a likelihood that a subject will develop fibrosis and/or progress to a particular stage of fibrosis and/or progress rapidly to a late-stage fibrosis:

$$G=(C1*rs12979860)+(C2*rs8099917)+(C3*rs10211152)+(C4*rs4374383)+(C5*rs16851720) \quad (1)$$

$$Z=[X1+G+(C6*age)] \quad (2)$$

$$FPS=1-1/[1+exp(Z)] \quad (3)$$

wherein:
exp(Z) is $e^Z$ wherein e is Euler's number;
C1 is a coefficient for weighting applied to rs12979860 genotypes;
C2 is a coefficient for weighting applied to rs8099917 genotypes;
C3 is a coefficient for weighting applied to rs10211152 genotypes;
C4 is a coefficient for weighting applied to rs4374383 genotypes; and
C5 is a coefficient for weighting applied to rs16851720 genotypes;
rs12979860=1.0 for a rs12979860-CC genotype, or −1.0 for a rs12979860-CT or rs12979860-TT genotype;
rs8099917=1.0 for a rs8099917-TT genotype, or −1.0 for a rs8099917-TG genotype or rs8099917-GG genotype;
rs10211152=1.0 for a rs10211152-CC genotype, or −1.0 for a rs10211152-TC genotype or rs10211152-TT genotype;
rs4374383=1.0 for a rs4374383-AG genotype, or 1.0 for a rs4374383-GG genotype, or −1.0 for a rs4374383-AA genotype;
rs16851720=1.0 for a rs16851720-AA genotype, or −1.0 for a rs16851720-AC genotype or a rs16851720-CC genotype;
a genotype that has not been determined is applied a null value subject to the proviso that data for at least one genotype for each of IL28B and MERTK must be present;
X1 represents an intermediate score;
C6 is a coefficient for weighting applied to age of subject; and
age is in years.

In one example, the data processor may comprise computer-executable mathematical algorithms (1)-(3) for calculating a fibrosis probability score (FPS) that is correlated with fibrosis stage or a likelihood that a subject will develop fibrosis and/or progress to a particular stage of fibrosis and/or progress rapidly to a late-stage fibrosis:

$$G=(C1*rs12979860)+(C2*rs8099917)+(C3*rs10211152)+(C4*rs4374383)+(C5*rs16851720) \quad (1)$$

$$Z=[X1+G+(C6*age)] \quad (2)$$

$$FPS=1-1/[1+exp(Z)] \quad (3)$$

wherein:
exp(Z) is $e^Z$ wherein e is Euler's number;
C1 is a coefficient for weighting applied to rs12979860 genotypes;
C2 is a coefficient for weighting applied to rs8099917 genotypes;
C3 is a coefficient for weighting applied to rs10211152 genotypes or genotypes of a MERTK SNP in linkage disequilibrium with rs10211152 selected from the group consisting of rs10165940, rs10168067, rs10205793, rs13387346, rs13402707, rs13416895, rs2230517, rs6723289, rs6723394, rs6735717 and rs13396030;
C4 is a coefficient for weighting applied to rs4374383 genotypes; and
C5 is a coefficient for weighting applied to rs16851720 genotypes;
rs12979860=1.0 for a rs12979860-CC genotype, or −1.0 for a rs12979860-CT or rs12979860-TT genotype;
rs8099917=1.0 for a rs8099917-TT genotype, or −1.0 for a rs8099917-TG genotype or rs8099917-GG genotype;
rs10211152=1.0 for a rs10211152-CC genotype, or −1.0 for a rs10211152-TC genotype or rs10211152-TT genotype;
rs10165940=1.0 for a rs10165940-GG genotype, or −1.0 for a rs10165940-AG genotype or rs10165940-AA genotype;
rs10168067=1.0 for a rs10168067-CC genotype, or −1.0 for a rs10168067-CG genotype or rs10168067-GG genotype;
rs10205793=1.0 for a rs10205793-GG genotype, or −1.0 for a rs10205793-AG genotype or rs10205793-AA genotype;
rs13387346=1.0 for a rs13387346-CC genotype, or −1.0 for a rs13387346-CT genotype or rs13387346-TT genotype;
rs13402707=1.0 for a rs13402707-CC genotype, or −1.0 for a rs13402707-CT genotype or rs13402707-TT genotype;
rs13416895=1.0 for a rs13416895-CC genotype, or −1.0 for a rs13416895-CG genotype or rs13416895-GG genotype;

rs2230517=1.0 for a rs2230517-GG genotype, or −1.0 for a rs2230517-AG genotype or rs2230517-AA genotype;

rs6723289=1.0 for a rs6723289-CC genotype, or −1.0 for a rs6723289-AC genotype or rs6723289-AA genotype;

rs6723394=1.0 for a rs6723394-CC genotype, or −1.0 for a rs6723394-AT genotype or rs6723394-TT genotype;

rs6735717=1.0 for a rs6735717-AA genotype, or −1.0 for a rs6735717-AG genotype or rs6735717-GG genotype;

rs13396030=1.0 for a rs13396030-GG genotype, or −1.0 for a rs13396030-AG genotype or rs13396030-AA genotype;

rs4374383=1.0 for a rs4374383-AG genotype, or 1.0 for a rs4374383-GG genotype, or −1.0 for a rs4374383-AA genotype;

rs16851720=1.0 for a rs16851720-AA genotype, or −1.0 for a rs16851720-AC genotype or a rs16851720-CC genotype;

a genotype that has not been determined is applied a null value subject to the proviso that data for at least one genotype for each of IL28B and MERTK must be present;

X1 represents an intermediate score;

C6 is a coefficient for weighting applied to age of subject; and age is in years.

In another example, the data processor may comprise computer-executable mathematical algorithms (1)-(3) for calculating a fibrosis probability score (FPS) that is correlated with fibrosis stage or a likelihood that a subject will develop fibrosis and/or progress to a particular stage of fibrosis and/or progress rapidly to a late-stage fibrosis:

$$G=(C1*rs12979860)+(C2*rs8099917)+(C3*rs10211152)+(C4*rs4374383)+(C5*rs16851720) \quad (1)$$

$$Z=[X1+G+(C6*age)+(C7*AST)+(C8*GGT)+(C9*Bilirubin)-(C10*platelets)] \quad (19)$$

$$FPS=1-1/[1+exp(Z)] \quad (3)$$

wherein:

exp(Z) is $e^Z$ wherein e is Euler's number;

C1 is a coefficient for weighting applied to rs12979860 genotypes;

C2 is a coefficient for weighting applied to rs8099917 genotypes;

C3 is a coefficient for weighting applied to rs10211152 genotypes;

C4 is a coefficient for weighting applied to rs4374383 genotypes; and

C5 is a coefficient for weighting applied to rs16851720 genotypes;

C6 is a coefficient for weighting applied to age of subject;

C7 is a coefficient for weighting applied to AST levels;

C8 is a coefficient for weighting applied to GGT levels;

C9 is a coefficient for weighting applied to bilirubin levels;

C10 is a coefficient for weighting applied to platelet levels;

rs12979860=1.0 for a rs12979860-CC genotype, or −1.0 for a rs12979860-CT or rs12979860-TT genotype;

rs8099917=1.0 for a rs8099917-TT genotype, or −1.0 for a rs8099917-TG genotype or rs8099917-GG genotype;

rs10211152=1.0 for a rs10211152-CC genotype, or −1.0 for a rs10211152-TC genotype or rs10211152-TT genotype;

rs4374383=1.0 for a rs4374383-AG genotype, or 1.0 for a rs4374383-GG genotype, or −1.0 for a rs4374383-AA genotype;

rs16851720=1.0 for a rs16851720-AA genotype, or −1.0 for a rs16851720-AC genotype or a rs16851720-CC genotype;

a genotype that has not been determined is applied a null value subject to the proviso that data for at least one genotype for each of IL28B and MERTK must be present;

each of AST, GGT, Bilirubin and platelets is optional and has a value of zero when absent;

AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum;

bilirubin when present is expressed as a weight per unit volume serum;

X1 represents an intermediate score; and age is in years.

In another example, the data processor may comprise computer-executable mathematical algorithms (1)-(3) for calculating a fibrosis probability score (FPS) that is correlated with fibrosis stage or a likelihood that a subject will develop fibrosis and/or progress to a particular stage of fibrosis and/or progress rapidly to a late-stage fibrosis:

$$G=(C1*rs12979860)+(C2*rs8099917)+(C3*rs10211152)+(C4*rs4374383)+(C5*rs16851720) \quad (1)$$

$$Z=[X1+G+(C6*age)+(C7*AST)+(C8*GGT)+(C9*Bilirubin)-(C10*platelets)] \quad (19)$$

$$FPS=1-1/[1+exp(Z)] \quad (3)$$

wherein:

exp(Z) is $e^Z$ wherein e is Euler's number;

C1 is a coefficient for weighting applied to rs12979860 genotypes;

C2 is a coefficient for weighting applied to rs8099917 genotypes;

C3 is a coefficient for weighting applied to rs10211152 genotypes or genotypes of a MERTK SNP in linkage disequilibrium with rs10211152 selected from the group consisting of rs10165940, rs10168067, rs10205793, rs13387346, rs13402707, rs13416895, rs2230517, rs6723289, rs6723394, rs6735717 and rs13396030;

C4 is a coefficient for weighting applied to rs4374383 genotypes; and

C5 is a coefficient for weighting applied to rs16851720 genotypes;

C6 is a coefficient for weighting applied to age of subject;

C7 is a coefficient for weighting applied to AST levels;

C8 is a coefficient for weighting applied to GGT levels;

C9 is a coefficient for weighting applied to bilirubin levels;

C10 is a coefficient for weighting applied to platelet levels;

rs12979860=1.0 for a rs12979860-CC genotype, or −1.0 for a rs12979860-CT or rs12979860-TT genotype;

rs8099917=1.0 for a rs8099917-TT genotype, or −1.0 for a rs8099917-TG genotype or rs8099917-GG genotype;

rs10211152=1.0 for a rs10211152-CC genotype, or −1.0 for a rs10211152-TC genotype or rs10211152-TT genotype;

rs10165940=1.0 for a rs10165940-GG genotype, or −1.0 for a rs10165940-AG genotype or rs10165940-AA genotype;

rs10168067=1.0 for a rs10168067-CC genotype, or −1.0 for a rs10168067-CG genotype or rs10168067-GG genotype;

rs10205793=1.0 for a rs10205793-GG genotype, or −1.0 for a rs10205793-AG genotype or rs10205793-AA genotype;

rs13387346=1.0 for a rs13387346-CC genotype, or −1.0 for a rs13387346-CT genotype or rs13387346-TT genotype;

rs13402707=1.0 for a rs13402707-CC genotype, or −1.0 for a rs13402707-CT genotype or rs13402707-TT genotype;

rs13416895=1.0 for a rs13416895-CC genotype, or −1.0 for a rs13416895-CG genotype or rs13416895-GG genotype;

rs2230517=1.0 for a rs2230517-GG genotype, or −1.0 for a rs2230517-AG genotype or rs2230517-AA genotype;

rs6723289=1.0 for a rs6723289-CC genotype, or −1.0 for a rs6723289-AC genotype or rs6723289-AA genotype;

rs6723394=1.0 for a rs6723394-CC genotype, or −1.0 for a rs6723394-AT genotype or rs6723394-TT genotype;

rs6735717=1.0 for a rs6735717-AA genotype, or −1.0 for a rs6735717-AG genotype or rs6735717-GG genotype;

rs13396030=1.0 for a rs13396030-GG genotype, or −1.0 for a rs13396030-AG genotype or rs13396030-AA genotype;

rs4374383=1.0 for a rs4374383-AG genotype, or 1.0 for a rs4374383-GG genotype, or −1.0 for a rs4374383-AA genotype;

rs16851720=1.0 for a rs16851720-AA genotype, or −1.0 for a rs16851720-AC genotype or a rs16851720-CC genotype;

a genotype that has not been determined is applied a null value subject to the proviso that data for at least one genotype for each of IL28B and MERTK must be present;

each of AST, GGT, Bilirubin and platelets is optional and has a value of zero when absent; AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum;

bilirubin when present is expressed as a weight per unit volume serum; X1 represents an intermediate score; and age is in years.

The present invention also provides a system for managing treatment of fibrosis or a medical condition associated with progression of fibrosis, said system comprising a computer comprising:

(a) an input interface configured to receive prognostic score data for a subject having early-stage fibrosis or a medical condition associated with onset of fibrosis, wherein the data are generated by the device as disclosed herein, and wherein a plurality of data points are collected over a time course before commencement of therapy and/or during therapy and/or following cessation of therapy collected over time;

(b) an input interface configured to receive data indicating a medical condition associated with onset of fibrosis in the subject and whether therapy is to treat the medical condition and/or the fibrosis;

(c) a reference database of therapies for fibrosis and medical conditions associated with fibrosis;

(d) a computer-readable storage medium for storing the data received at (a) and (b) and (c);

(e) a data processor that is executed to plot calculate a prognostic score based on the stored data;

(f) a processor for calculating a preferred therapy based on the stored data at (a) and (b) and (c); and (g) a port or readable interface for communicating the preferred therapy calculated by the processor to a user.

In one example, the computer and the device may be configured to be in communication with each other to facilitate transfer of prognostic score data from the device to the computer. For example, the computer and the device may be in wired communication with each other. In an alternative example, the computer and the device may be in wireless communication with each other.

In another example, the computer and the device are not configured to be in the same network, and wherein prognostic score data are input to the computer following their determination remotely using the device. For example, the prognostic score data may be transferred to the computer from a computer-readable medium. In an alternative example, the prognostic score data may be inputted manually to the computer.

The present invention also provides a method of monitoring the efficacy of therapy for fibrosis or a medical condition associated with progression of liver fibrosis, said method comprising implementing the system as disclosed herein on a subject undergoing treatment for fibrosis or a condition associated therewith and modifying the therapy according to the prognostic score data obtained over time.

The diagnostic/prognostic method of the present invention, and one or more algorithms, devices and systems described herein provide for focused or tailored therapy of fibrosis by identifying those patients at significant risk of disease and/or disease progression at an early stage and tailoring their treatment accordingly.

DETAILED DESCRIPTION OF THE PREFERRED EMBODIMENTS

Figure 1:
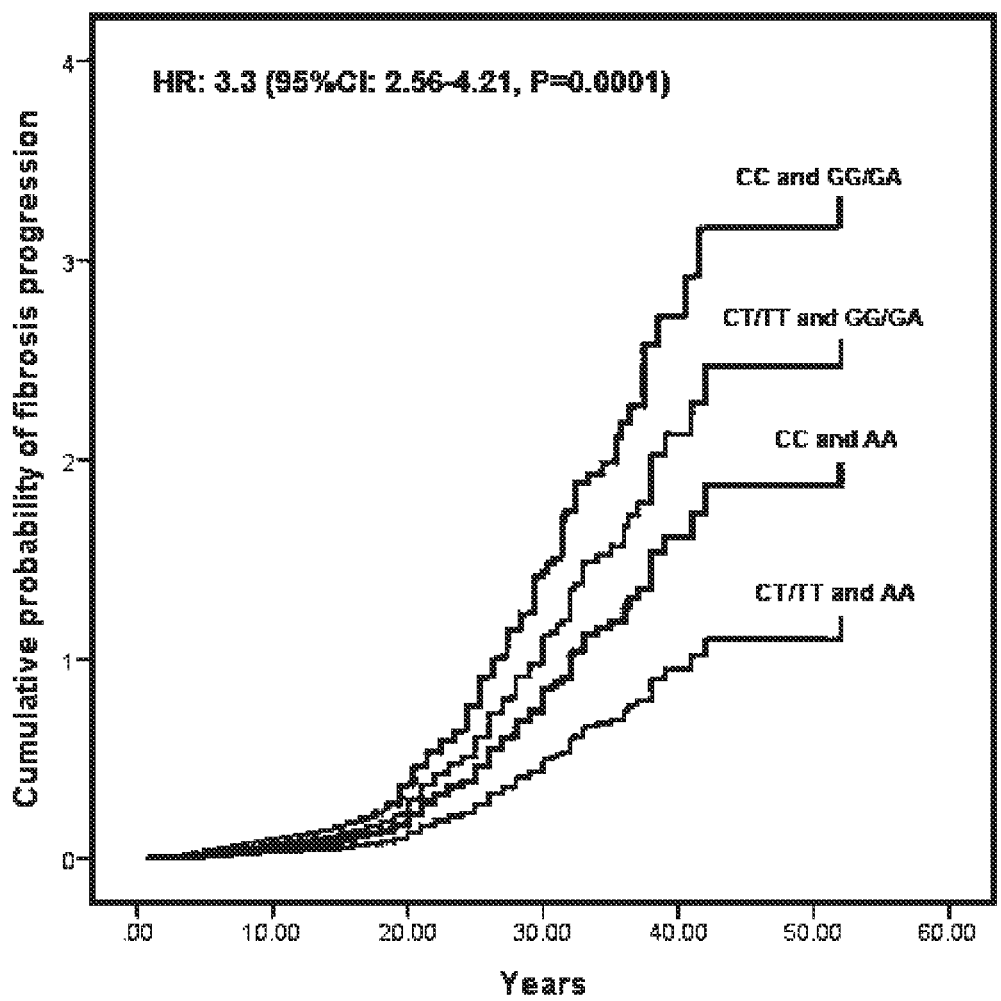
FIG. 1 is a graphical representation showing the cumulative probability of progression of liver fibrosis in subjects having chronic HCV-infection (y-axis), based on their ages at the time of infection (x-axis), and stratified according to their combined genotypes at rs12979860 and rs4374383. The combined genotypes indicated in the figure are rs12979860-CC and rs4374383-AG/GG ("CC and GG/GA"), rs12979860-CT/TT and rs4374383-AG/GG ("CT/TT and GG/GA"), rs12979860-CC and rs4374383-AA ("CC and AA"), and rs12979860-CT/TT and rs4374383-AA ("CT/TT and AA") subjects. The population sample consisted of 1000 Caucasian subjects having chronic HCV infection.

One example of the present invention provides a method of determining a likelihood that a subject having a medical condition associated with onset or progression of fibrosis is susceptible to fibrosis and/or is predisposed to severe fibrosis and/or progression of fibrosis, the method comprising performing one or more genotyping assays on a DNA-containing sample obtained from the subject e.g., blood, serum, buccal swab, etc., wherein the one or more assays are configured to discriminate single nuclear polymorphism (SNP) genotypes in or at least linked to both the human IL28B gene and the human MERTK gene, wherein the SNPs are selected from rs12979860, rs8099917, rs10211152 and rs4374383, a SNP in linkage disequilibrium with rs12979860, a SNP in linkage disequilibrium with rs8099917, a SNP in linkage disequilibrium with rs10211152 and a SNP in linkage disequilibrium with rs4374383, wherein the assay results indicate a likelihood that the subject will develop fibrosis and/or progress to a particular stage of fibrosis and/or progress rapidly to a late-stage fibrosis.

In one example, a SNP in linkage disequilibrium with rs10211152 may be a SNP in the MERTK gene selected from the group consisting of rs10165940, rs10168067, rs10205793, rs13387346, rs13402707, rs13416895, rs2230517, rs6723289, rs6723394, rs6735717 and rs13396030.

Accordingly, in one example, the method may comprise:
(a) performing the one or more genotyping assays configured to discriminate between different genotypes in the human IL28B gene and the human MERTK gene, wherein the genotypes in the human IL28B gene are in the SNP rs12979860 and/or the SNP rs8099917, and wherein the genotypes in the human MERTK gene are in the SNP rs10211152 and/or a SNP in the MERTK gene in linkage disequilibrium with rs10211152 selected from the group consisting of rs10165940, rs10168067, rs10205793, rs13387346, rs13402707, rs13416895, rs2230517, rs6723289, rs6723394, rs6735717 and rs13396030; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a CC genotype in rs12979860 and/or a TT genotype in rs8099917; and
(ii) a CC genotype in rs10211152 and/or a GG genotype in rs10165940 and/or a CC genotype in rs10168067 and/or a GG genotype in rs10205793 and/or a CC genotype in rs13387346 and/or a CC genotype in rs13402707 and/or a CC genotype in rs13416895 and/or a GG genotype in rs2230517 and/or a CC genotype in rs6723289 and/or a CC genotype in rs6723394 and/or a AA genotype in rs6735717 and/or a GG genotype in rs13396030.

In another example, the invention provides a likelihood that a subject having a medical condition associated with onset or progression of fibrosis will develop fibrosis, said method comprising:
(a) performing one or more genotyping assays on a DNA-containing sample obtained from the subject, wherein the one or more assays are configured to discriminate between different genotypes in or linked to both the human IL28B and the human MERTK gene, wherein the genotypes in or linked to the human IL28B gene are alleles of a single nuclear polymorphism (SNP) selected from rs12979860, rs8099917, an IL28B SNP in linkage disequilibrium with rs12979860, and an IL28B SNP in linkage disequilibrium with rs8099917, and wherein the genotypes in or linked to the human MERTK gene are alleles of a SNP selected from rs10211152, rs4374383, a SNP in linkage disequilibrium with rs10211152 and a SNP in linkage disequilibrium with rs4374383; and (b) correlating the genotyping assay results to the likelihood that the subject will develop fibrosis, wherein a combination of the following genotypes (i) and (ii) indicates a strong likelihood that the subject will develop fibrosis:

(i) a CC genotype in rs12979860 and/or a TT genotype in rs8099917 and/or a genotype in linkage disequilibrium with said CC genotype or TT genotype; and (ii) a CC genotype in rs10211152 and/or an AG genotype or GG genotype in rs4374383 and/or genotype in linkage disequilibrium with said CC genotype or AG genotype or GG genotype, thereby determining a likelihood that the subject will develop fibrosis.

In another example, the invention provides a likelihood that a subject having a medical condition associated with onset or progression of fibrosis will progress to a particular stage of fibrosis, said method comprising:

(a) performing one or more genotyping assays on a DNA-containing sample obtained from the subject, wherein the one or more assays are configured to discriminate between different genotypes in or linked to both the human IL28B and the human MERTK gene, wherein the genotypes in or linked to the human IL28B gene are alleles of a single nuclear polymorphism (SNP) selected from rs12979860, rs8099917, an IL28B SNP in linkage disequilibrium with rs12979860, and an IL28B SNP in linkage disequilibrium with rs8099917, and wherein the genotypes in or linked to the human MERTK gene are alleles of a SNP selected from rs10211152, rs4374383, a SNP in linkage disequilibrium with rs10211152 and a SNP in linkage disequilibrium with rs4374383; and (b) correlating the genotyping assay results to the likelihood that the subject will develop fibrosis, wherein a combination of the following genotypes (i) and (ii) indicates a strong likelihood that the subject will develop fibrosis:

(i) a CC genotype in rs12979860 and/or a TT genotype in rs8099917 and/or a genotype in linkage disequilibrium with said CC genotype or TT genotype; and (ii) a CC genotype in rs10211152 and/or an AG genotype or GG genotype in rs4374383 and/or genotype in linkage disequilibrium with said CC genotype or AG genotype or GG genotype, thereby determining a likelihood that the subject will progress to a particular stage of fibrosis.

In another example, the invention provides a method of predicting a likelihood that fibrosis will progress rapidly to a late-stage fibrosis in a subject having a medical condition associated with onset or progression of fibrosis, said method comprising:

(a) performing one or more genotyping assays on a DNA-containing sample obtained from the subject, wherein the one or more assays are configured to discriminate between different genotypes in or linked to both the human IL28B and the human MERTK gene, wherein the genotypes in or linked to the human IL28B gene are alleles of a single nuclear polymorphism (SNP) selected from rs12979860, rs8099917, a SNP in linkage disequilibrium with rs12979860, and a SNP in linkage disequilibrium with rs8099917, and wherein the genotypes in or linked to the human MERTK gene are alleles of a SNP selected from rs10211152, rs4374383, a SNP in linkage disequilibrium with rs10211152 and a SNP in linkage disequilibrium with rs4374383; and (b) correlating the genotyping assay results to the likelihood that the subject will develop fibrosis, wherein a combination of the following genotypes (i) and (ii) indicates a strong likelihood that the subject will progress rapidly to a late-stage fibrosis:

(i) a CC genotype in rs12979860 and/or a TT genotype in rs8099917 and/or a genotype in linkage disequilibrium with said CC genotype or TT genotype; and (ii) a CC genotype in rs10211152 and/or an AG genotype or GG genotype in rs4374383 and/or genotype in linkage disequilibrium with said CC genotype or AG genotype or GG genotype, thereby determining a likelihood that fibrosis will progress rapidly to a late-stage fibrosis in the subject.

A preferred combination of genotypes for use in the performing the invention comprise combinations of the following genotypes (i) and (ii), which each indicate a strong likelihood that the subject will develop fibrosis and/or progress rapidly to a late-stage fibrosis:

(i) a CC genotype in rs12979860 and/or a TT genotype in rs8099917 and/or a genotype in linkage disequilibrium with said CC genotype or TT genotype; and (ii) a CC genotype in rs10211152 and/or an AG genotype or GG genotype in rs4374383 and/or genotype in linkage disequilibrium with said CC genotype or AG genotype or GG genotype.

A particularly preferred combination of genotypes for use in the performing the invention comprise combinations of the following genotypes (i) and (ii), which each indicate a strong likelihood that the subject will develop fibrosis and/or progress rapidly to a late-stage fibrosis:

A) (i) a CC genotype in rs12979860 and/or a TT genotype in rs8099917; and (ii) a CC genotype in rs10211152 and/or an AG genotype or GG genotype in rs4374383; or B) (i) a CC genotype in rs12979860; and (ii) a CC genotype in rs10211152; or C) (i) a CC genotype in rs12979860; and (ii) an AG genotype or GG genotype in rs4374383; or D) (i) a TT genotype in rs8099917; and (ii) a CC genotype in rs10211152; or E) (i) a TT genotype in rs8099917; and (ii) an AG genotype or GG genotype in rs4374383.

As will be understood by the skilled artisan, the present invention requires performance of the subject genotyping assays under conditions that discriminate between genotypes at each locus tested i.e., the IL28B and MERTK SNP loci. Standard multiplex SNP genotyping assays are configured to achieve such discrimination e.g., by employing different coded labels on primers or ddNTPs employed in the assay chemistry. For example, the assay is configured to at least provide discrimination between homozygotes (CC), heterozygotes (CT) and alternate homozygotes (TT) at rs12979860 and/or between homozygotes (TT), heterozygotes (TG) and alternate homozygotes (GG) at rs8099917 and/or between homozygotes (CC), heterozygotes (CT) and alternate homozygotes (TT) at rs10211152 and/or between homozygotes (GG), heterozygotes (AG) and alternate homozygotes (AA) at rs4374383.

Alternatively, or in addition, the assay is configured to at least provide discrimination between homozygotes (GG), heterozygotes (AG) and alternate homozygotes (AA) at rs10165940 and/or between homozygotes (CC), heterozygotes (CG) and alternate homozygotes (CC) at rs10168067 and/or between homozygotes (GG), heterozygotes (AG) and alternate homozygotes (AA) at rs10205793 and/or between homozygotes (CC), heterozygotes (CT) and alternate homozygotes (TT) at rs13387346 and/or between homozygotes (CC), heterozygotes (CT) and alternate homozygotes (TT) at rs13402707 and/or between homozygotes (CC), heterozygotes (CG) and alternate homozygotes (GG) at rs13416895 and/or between homozygotes (GG), heterozygotes (AG) and alternate homozygotes (AA) at rs2230517 and/or between homozygotes (CC), heterozygotes (CA) and alternate homozygotes (AA) at rs6723289 and/or between homozygotes (CC), heterozygotes (CT) and alternate homozygotes (TT) at rs6723394 and/or between homozygotes (AA), heterozygotes (AG) and alternate homozygotes (GG) at rs6735717 and/or between homozygotes (GG), heterozygotes (AG) and alternate homozygotes (AA) at rs13396030.

In some examples, the one or more genotyping assays are configured to discriminate the single nuclear polymorphism (SNP) genotypes in IL28B and MERTK genes, wherein the SNP genotypes detected by the one or more genotyping assays each have a frequency of at least about 20% in a population or genetic group to which the subject belongs. For example, the detected genotypes each have a frequency of 20% or at least 25% or 30% or 35% or 40% or 45% or 50% or 55% or 60% or 65% or 70% or 75% or 80% or 85% or 90% or 95% in the test population or genetic group. This is because not all SNP alleles are represented at equal frequencies across all human genetic groups. Where a test population is genetically more homogeneous, a test that detects SNP genotpyes having a frequency of at least 20% in the predominant genetic group(s) is beneficial in terms of providing higher detection rates and/or reduced false negatives. For example, a test performed on a sample obtained in Africa may be configured to detect SNP genotypes at rs8099917 as opposed to rs12979860 in IL28B, in combination with detection of SNP genotypes at rs10211152 and/or rs4374383 in MERTK, given the higher representation of the rs8099917-TT genotype relative to rs12979860-CC genotype. Alternatively, to improve sensitivity and/or specificity, tests performed on a sample obtained in Africa may be configured to detect both SNP genotypes at rs8099917 and rs12979860 in IL28B, in combination with detection of SNP genotypes at rs10211152 and/or rs4374383 in MERTK. Similarly, a test performed on a sample obtained in Peoples Republic of China or Japan or South Korea may be configured to detect SNP genotypes at rs10211152 as opposed to rs4374383 in MERTK, in combination with detection of SNP genotypes at rs12979860 and/or rs8099917 in IL28B, given the higher representation of the rs10211152-CC genotype relative to rs4374383-GG genotype. Alternatively, to improve sensitivity and/or specificity albeit at higher cost per unit, tests performed on a sample obtained in Peoples Republic of China or Japan or South Korea may be configured to detect SNP genotypes at both rs10211152 and rs4374383 in MERTK, in combination with detection of SNP genotypes at rs12979860 and/or rs8099917 in IL28B. Less desirably, a test performed in Peoples Republic of China or Japan or South Korea may be configured to detect SNP genotypes at rs4374383-AG as opposed to rs4374383-GG in MERTK, in combination with detection of SNP genotypes at rs12979860 or rs8099917 in IL28B, given the higher representation of the rs4374383-AG genotype relative to rs4374383-GG genotype. It will also be apparent to the skilled artisan that in any geographical region, combinations of such tests tailored to the genetic background of the test population may be used, for improved applicability across all genetic groups in the population.

In some examples, where test populations are genetically more diverse, the one or more genotyping assays may be configured to discriminate the single nuclear polymorphism (SNP) genotypes in IL28B and MERTK genes, wherein the SNP genotypes detected by the one or more genotyping assays have a frequency of at least 30% or at least 35% or at least 40% or at least 45% or at least 50% across all genetic groups in the population. Such a generic test may be beneficial in terms of reduced effort, time and cost. The data provided herein on allele frequencies in different genetic groups permit determination of allele frequencies in any test population based on the representation of each genetic group. For example, a hypothetic test population comprising subjects derived from Africa (20%), Europe (40%), and Peoples' Republic of China (40%) would comprise on average about 55.8% of persons representing the rs12979860-CC genotype and, as a consequence, a test configured to detect SNP genotypes at rs12979860 may be generally useful in that test population. In contrast, a hypothetic test population comprising subjects derived from Africa (10%), Europe (10%), and Peoples' Republic of China (80%) would comprise on average only about 25.52% of persons representing the rs12979860-CC genotype and, as a consequence, a test configured to detect SNP genotypes at rs8099917 may be generally useful in that test population.

In a preferred example of the invention as described according to any embodiment hereof, a preferred SNP in linkage disequilibrium with rs10211152 is selected from the group consisting of rs17175626 and rs6748256.

In another preferred example of the invention as described according to any embodiment hereof, a preferred SNP in linkage disequilibrium with rs10211152 is a SNP in the MERTK gene selected from the group consisting of rs10165940, rs10168067, rs10205793, rs13387346, rs13402707, rs13416895, rs2230517, rs6723289, rs6723394, rs6735717 and rs13396030.

Similarly, a preferred SNP in linkage disequilibrium with rs4374383 is selected from the group consisting of rs17175626 and rs6748256. The skilled artisan will also be aware that re 12979860 is in linage disequilibrium with rs8099917.

As used throughout this description and in the accompanying claims, and unless otherwise stated in the context of a particular example of the invention, the term "strong likelihood" or "strong probability" shall be taken to mean that the combined genotypes or alleles provide a stronger association with occurrence of a stated event relative to the sum of the associations of individual genotypes or alleles of that same combination with the same event. That is, the association of the combined genotypes or alleles is non-additive or indicative of an interaction between the stated genotypes or alleles, and provides a stronger association than that obtained by adding the separate effect of each of the genotypes.

For example, a strong likelihood of fibrosis or a particular stage of fibrosis or rapid fibrosis progression is indicated by an average O.R.=7.4 (p<0.0001) for the combination of the MERTK SNP rs10211152 and the IL28B SNP rs1297860, in view of their additive average O.R.=4.99 [average O.R.=2.82 for rs10211152 (p<0.0001) plus average O.R.=2.17 for rs1297860 (p<0.0001)]. Similarly, a strong likelihood of fibrosis a particular stage of fibrosis or or rapid fibrosis progression is indicated by an average O.R.=4.61 (p<0.0001) for the combination of the MERTK SNP rs4374383 and the IL28B SNP rs1297860, in view of their additive average O.R.=4.06 [average O.R.=1.89 for rs4374383 (p<0.0001) plus average O.R.=2.17 for rs1297860 (p<0.0001)].

Alternatively, or in addition, a strong likelihood that a stated event has occurred or will occur is provided by one or more of the following measures of test accuracy:
  (i) an odds ratio in a range from 4-20 or having a value greater than about 4 or preferably at least 5 or 6 or 7 or 8 or 9 or even more preferably at least 10; and/or
  (ii) a ROC curve area greater than about 0.5, and preferably at least 0.6 or 0.7 or 0.8 or 0.9 or 0.95 for two subject populations having early-stage fibrosis and late-stage fibrosis; and/or
  (iii) an assay specificity in a range from 0.5 to 0.99 including a specificity greater than about 0.5, or preferably at least 0.6 or 0.7 or 0.8 or 0.9 or more preferably at least 0.95, with a corresponding sensitivity in a range from 0.2 to 0.99 including a sensitivity greater than about 0.2, preferably greater than 0.3 or 0.4 or 0.5 or 0.6 or 0.7 or 0.8 or 0.9, and more preferably at least 0.95; and/or
  (iv) an assay sensitivity in a range from 0.5 to 0.99 including a sensitivity greater than about 0.5, or preferably at least 0.6 or 0.7 or 0.8 or 0.9 or more preferably at least 0.95, with a corresponding specificity in a range from 0.2 to 0.99 including a specificity greater than about 0.2, preferably greater than 0.3 or 0.4 or 0.5 or 0.6 or 0.7 or 0.8 or 0.9, and more preferably at least 0.95; and/or
  (v) an assay sensitivity of at least about 75% combined with an assay specificity of at least about 75%, or a sensitivity of at least about 80% combined with a specificity of at least about 80%, or a sensitivity of at least about 85% combined with a specificity of at least about 85%, or a sensitivity of at least about 90% combined with a specificity of at least about 90%, or a sensitivity of at least about 95% combined with a specificity of at least about 95%; and/or
  (vi) a positive likelihood ratio, calculated as sensitivity/(1-specificity), having a value in a range from 1-20 and/or having a value greater than about 1, and preferably having a value of at least 2 or 3 or 4 or 5 or 6 or 7 or 8 or 9 or 10.

In this respect, the assay "sensitivity" is a proportion of patients having a particular stage of fibrosis e.g., late stage or end-stage fibrosis, who are correctly identified as such by the SNP genotyping, whereas the assay "specificity" is a proportion of patients having a particular stage of fibrosis e.g., in early stage fibrosis or having no visible/detectable fibrosis, who are correctly identified as such by the SNP genotyping.

As used throughout this description and in the accompanying claims, and unless otherwise stated in the context of a particular example of the invention, the term "late-stage fibrosis" is meant that the subject has at least one body organ system relevant to a disease or medical condition associated with the fibrosis that exhibits excessive ECM deposition characterized by a detectable level of organ stiffening and/or septa formation and/or remodeling or other architectural distortion of the organ. The term "late-stage fibrosis" also includes an end-stage fibrosis in which functionality of the organ is dramatically reduced or non-functional, such as an organ requiring transplantation. The term "late stage fibrosis" shall also be taken to include a Scheuer/Batts-Ludwig/Tsui Stage 3 or Stage 4 of hepatic fibrosis or a Metavir stage F3 or F4 of hepatic fibrosis or a score of 4 or 5 or 6 in a Staging 0-6 system e.g., Ishak staging system, or equivalent physiological stage according to any other known staging system.

In contrast, the term "early-stage fibrosis" as used herein unless the context requires otherwise shall be taken to mean that the subject has either no detectable fibrosis in an organ system relevant to a disease or medical condition associated with the fibrosis and/or that the organ has a normal amount of connective tissue without detectable septa formation and/or tissue stiffening and/or remodelling. The term "early-stage fibrosis" shall also be taken to include a Scheuer/Batts-Ludwig/Tsui Stage 0 or Stage 1 organ, or a Metavir stage F0 or F1 organ, or a score of 0 or 1 in a Staging 0-6 system e.g., Ishak staging system, or equivalent physiological stage according to any other known staging system.

As will be known to the skilled artisan, the term "progression" refers to the degree of fibrosis such as the survival rate determined from the beginning of symptoms of fibrosis or in progression from early-stage fibrosis to late-stage or end-stage fibrosis. A subject having fibrosis may have a rapid disease progression or a slow disease progression, however these terms are to be taken as relative terms in this context. As used throughout this description and in the accompanying claims, and unless otherwise stated in the context of a particular example of the invention, the term "rapid progression" or "progress rapidly" or similar in the context of fibrosis progression shall be taken to refer to a rate of fibrosis progression in an individual at risk of having fibrosis or having early-stage fibrosis attributable to genotype. A "rapid progression" includes a rate of progression of fibrosis from early stage to late-stage fibrosis that is at least about 1 or 2 or 3 or 4 or 5 or 6 or 7 or 8 or 9 or 10 or 11 or 12 or 13 or 14 or 15 or 16 or 17 or 18 or 19 or 20 years shorter than for an individual having a moderate or slow rate of progression, and preferably has similar or the same non-genetic factors contributing to the fibrosis. For example, the individual having a moderate or slow rate of progression may be age-matched and gender-matched with an individual for which a rapid progression is being determined. The skilled artisan is aware that a moderate or normal rate of progression of fibrosis will vary according to the affected organ and disease indication associated with the fibrosis, however such rates are known in the literature. For example, a moderate rate of progression of IPF is generally at least about 2-10 years including 2 or 3 or 4 or 5 or 6 or 7 or 8 or 9 or 10 years and any parts of years thereof, whereas a moderate rate of liver fibrosis e.g., in subjects having steatosis or chronic HCV/HBV infection, occurs over a period of about 8-40 years depending on age and gender of the subject, including 8 or 9 or 10 or 11 or 12 or 13 or 14 or 15 or 16 or 17 or 18 or 19 or 20 or 21 or 22 or 23 or 24 or 25 or 26 or 27 or 28 or 29 or 30 or 31 or 32 or 33 or 34 or 35 or 36 or 37 or 38 or 39 or 40 years and any parts of years thereof. Thus, "rapid progression" may also include a progression from early-stage fibrosis to late-stage or end-stage fibrosis in less than about 1 or 2 or 3 or 4 or 5 or 6 or 7 or 8 or 9 or 10 or 11 or 12 or 13 or 14 or 15 or 16 or 7 or 18 or 19 or 20 or 21 or 22 or 23 or 24 months or in less than 1 or 2 or 3 or 4 or 5 or 6 or 7 or 8 or 9 or 10 years.

The present invention is not limited by the medical condition associated with onset or progression of fibrosis. For example, the subject may have a medical condition associated with progression of fibrosis that is selected from the group consisting of an autoimmune disease, a metabolic liver disease, a disease with secondary involvement of the liver, α1-antitrypsin deficiency, Wilson disease, fructosemia, galactosemia, a glycogen storage disease, hemochromatosis, Gaucher disease, Zellweger syndrome, tyrosinemia, a congenital hepatic fibrosis, brucellosis, echinococcosis, chronic hepatitis B, chronic hepatitis C, non-alcoholic steatohepatitis (NASH), primary biliary cirrhosis, primary sclerosing cholangitis, reduced hepatic blood flow, Budd-Chiari syndrome, heart failure, hepatic veno-occlusive disease, portal vein thrombosis, hepatocellular carcinoma, alcohol toxicity, amiodarone toxicity, chlorpromazine toxicity, isoniazid toxicity, methotrexate toxicity, methyldopa toxicity, oxyphenisatin toxicity, tolbutamide toxicity, scarring due to prior liver surgery, bile duct strictures due to impacted gallstones, diabetes, diabetic renal disease, hyperglycemia, a microvascular complication of diabetes, a macrovascular complication of diabetes, retinopathy, nephropathy, cardiomyopathy, peripheral vascular disease, a cerebrovascular disorder, atherosclerosis, and Chrohn's disease.

In a preferred example, the subject has a medical condition associated with progression of liver fibrosis such as chronic hepatitis B infection or chronic hepatitis C infection or non-alcoholic fatty liver disease (NAFLD) or non-alcoholic steatohepatitis (NASH), or has a medical condition associated with progression of renal fibrosis such diabetes or diabetic renal disease, or has a medical condition associated with intestinal fibrosis such as Chrohn's disease, or has a condition associated with pulmonary fibrosis such as IPF.

The method according to any example of the invention described herein may further comprise performing one or more additional genotyping assays on the DNA-containing sample obtained from the subject, wherein the one or more additional genotyping assays are configured to discriminate single nuclear polymorphism (SNP) genotypes in the human RNF7 gene, wherein the SNPs are selected from rs16851720 and a SNP in linkage disequilibrium with rs16851720. Preferably, the one or more additional genotyping assays are configured to discriminate single nuclear polymorphism (SNP) genotypes in rs16851720. Even more preferably, the one or more additional genotyping assays are configured to discriminate single nuclear polymorphism (SNP) genotypes in the SNP locus rs16851720, and wherein detection of an AA genotype in rs16851720 in combination with the diagnostic/prognostic SNPs of the invention in both the IL28B and MERTK genes indicates a strong likelihood that the subject will develop fibrosis and/or progress rapidly to a late-stage fibrosis. As exemplified herein, the predictive power of this multiplex assay is enhanced significantly. For example, the combination of SNP alleles at rs12979860 and rs4374383 and rs168720 provides a more than additive O.R.=8.16; p<0.0001.

Standard methods are employed to perform the diagnostic/prognostic test of the present invention. For example, PCR assays and/or real-time PCR assays and/or minisequencing assays and/or next generation sequencing assays and/or isothermal nucleic acid sequence-based amplification assays (NASBA) and/or oligonucleotide ligation-PCR assays may be employed. Multiplex assays are particularly convenient for discriminating between alleles at the various SNP loci described herein, and in this context multiplex PCR and multiplex sequencing formats are particularly preferred.

Components for performing the invention may be provided in the form of a kit, optionally with instructions for use in the subject method. Exemplary kits will comprise two or more nucleic acids that discriminate between different target genotypes in each of IL28B and MERTK genes, or three or more nucleic acids that discriminate between different target genotypes in each of IL28B and MERTK and RNF7 genes. Preferred nucleic acids for performing the invention will comprise sequences derived from the publicly-available sequences flanking the diagnostic/prognostic SNPs in each of IL28B and MERTK described herein and, optionally, from the publicly-available sequences flanking the diagnostic/prognostic SNPs in RNF7 described herein. Thus, the nucleic acids are suitable for discriminating between SNP alleles at rs12979860 or rs8099917 in combination with SNP alleles at rs10211152 or rs4374383 or rs17175626 or rs6748256. Alternatively, the nucleic acids are suitable for discriminating between SNP alleles at rs12979860 or rs8099917 in combination with SNP alleles at rs10211152 or rs4374383 or rs17175626 or rs6748256 and in combination with SNP alleles at rs16851720. Preferred nucleic acids for such allele discrimination have a minimum length, 5'-terminus and 3'-terminus compatible with the assay chemistry employed. Such parameters are determined without under experimentation. Optionally, the nucleic acids are differentially labeled i.e., coded to permit discrimination between IL28B and MERTK and RNF7 end-products of the assay in multiplex reactions. Preferred labels for nucleic acids are fluorophores or coloured dyes known in the art.

Preferred nucleic acids for use in performing the invention, e.g., in sequence-based assay chemistry, comprise at least 6 or 7 or 8 or 9 or 10 or 11 or 12 nucleotides in length having a sequence that is complementary to sequence in human genomic DNA upstream of a polymorphic nucleotide defining a specific SNP described herein, and have a 3'-end terminating immediately upstream of or adjacent to the polymorphic nucleotide.

For sequence-based assay chemistry, such kits may also comprise one or more ddNTPs comprising a base that corresponds to a SNP nucleotide at rs12979860 or rs8099917 or rs10211152 or rs4374383 or rs17175626 or rs6748256 or rs16851720. For example, dNTPs for use in identifying a strong likelihood of fibrosis or fibrosis progression may comprise ddCTP for chain termination in rs12979860 or rs10211152 and/or a dTTP for chain termination in rs8099917 and/or ddGTP for chain termination in rs4374383. Optionally, the ddNTPs are differentially labeled i.e., coded to permit discrimination between end-products of the assay in multiplex reactions. Preferred labels for nucleic acids are fluorophores or coloured dyes known in the art, subject to the proviso that such labels are different from any labels employed to code nucleic acid probes or primers.

Optionally, the kit further comprises one or more enzymes for use in performing an amplification or sequencing reaction appropriate to the assay chemistry.

The present invention also provides a kit for performing the method according to any example described herein.

The present invention also provides a method of treating a subject for fibrosis or for a medical condition associated with progression of fibrosis, said method comprising performing the method according to any example hereof on a DNA-containing sample obtained from a subject having no visible fibrosis or early signs of fibrosis to thereby determine a likelihood that the fibrosis develop or that fibrosis will progress rapidly to a late-stage fibrosis in the subject and then treating the fibrosis and/or the medical condition in a subject having a strong likelihood of developing fibrosis or progressing rapidly to a late-stage fibrosis.

In one example, the method may comprise:
(a) (i) receiving a test result obtained by performing the method according to any example hereof, wherein the test results determine that fibrosis has developed in the subject or that there a strong likelihood that the subject is susceptible to fibrosis and/or that fibrosis will progress rapidly to a late-stage in the subject; or (ii) receiving an indication or recommendation to treat a subject for the fibrosis or the medical condition based on a test result obtained by performing the method according to any example hereof, wherein the test results determine that fibrosis has developed in the subject or that there a strong likelihood that the subject is susceptible to fibrosis and/or that fibrosis will progress rapidly to a late-stage in the subject; and (b) treating a subject for the fibrosis and/or the medical condition based on the test result or indication or recommendation.

In performing this therapeutic method, it is contemplated that, as a first step, a DNA-containing sample obtained from a subject having no visible fibrosis or having early fibrosis is forwarded to be analyzed by the method. For example, a physician may obtain the sample and forward the sample to a pathology laboratory for testing.

As with the diagnostic/prognostic assay of the invention, the subject to be treated will generally have a pre-existing diagnosis of a medical condition associated with onset or progression of fibrosis. For example, the subject may suffer from an autoimmune disease, a metabolic liver disease, a disease with secondary involvement of the liver, α1-antitrypsin deficiency, Wilson disease, fructosemia, galactosemia, a glycogen storage disease, hemochromatosis, Gaucher disease, Zellweger syndrome, tyrosinemia, a congenital hepatic fibrosis, brucellosis, echinococcosis, chronic hepatitis B, chronic hepatitis C, non-alcoholic steatohepatitis (NASH), primary biliary cirrhosis, primary sclerosing cholangitis, reduced hepatic blood flow, Budd-Chiari syndrome, heart failure, hepatic veno-occlusive disease, portal vein thrombosis, hepatocellular carcinoma, alcohol toxicity, amiodarone toxicity, chlorpromazine toxicity, isoniazid toxicity, methotrexate toxicity, methyldopa toxicity, oxyphenisatin toxicity, tolbutamide toxicity, scarring due to prior liver surgery, bile duct strictures due to impacted gallstones, diabetes, diabetic renal disease, hyperglycemia, a microvascular complication of diabetes, a macrovascular complication of diabetes, retinopathy, nephropathy, cardiomyopathy, peripheral vascular disease, a cerebrovascular disorder, atherosclerosis, or Chrohn's disease.

Treatment may comprise administration of an anti-fibrotic compound and/or a compound that treats the medical condition causing the fibrosis to thereby alleviate the fibrosis or reduce or slow or arrest progression of fibrosis.

Exemplary therapies for fibrosis include administration a corticosteroid, penicillamine, tumour necrosis factor inhibitor (anti-TNF agent), a pan-caspase inhibitor, or other anti-fibrotic medicament.

Exemplary therapies for treatment of a subject having a chronic hepatitis virus infection e.g., HCV or HBV, may comprise administering an antiviral compound e.g., ribavirin, and/or pegylated IFNα, and/or a direct-acting antiviral (DAA) compound such as boceprevir or telaprevir, and/or a protease inhibitor e.g., asunaprevir, danoprevir, vaniprevir, ritonavir, simeprevir, MK-5172, BI-201335, or ABT-450, and/or a NSSB polymerase inhibitor such as tegobuvir, filibuvir, BI-207127, VX-222, ANA598, ABT-333, RG7128 (mericitabine), or GS-7977 (sofosbuvir), and/or a NSSA inhibitor such as daclatasvir, BT-267, GS-5885, or PPI-461, to a subject in need thereof.

Exemplary therapies for treatment of a subject having hepatotoxicity e.g., in the case of hemochromatosis, may comprise removing a toxicity-causing agent or heavy metal or fatty acid from the body or body organ of a subject in need thereof.

Constriction of ducts e.g., as a consequence of surgical intervention may require surgical intervention to decompressing bile ducts.

This invention also provides a device configured to provide an indication of fibrosis stage or a probability or likelihood that a subject having no visible fibrosis or having early-stage fibrosis or having a medical condition associated with onset or progression of fibrosis will develop fibrosis or progress rapidly to a late-stage fibrosis, wherein the device comprises:

(a) an input interface configured to receive data comprising (i) the combined IL28B/MERTK genotype of the subject determined performing the method as described in any example hereof, (ii) the age of the subject, and (iii) the gender of the subject;

(b) a computer-readable storage medium for storing data at least for the combined IL28B/MERTK genotype or the combined IL28B/MERTK/RNF7 genotype of the subject, the age of the subject, and the gender of the subject;

(c) a data processor that is executed to calculate a prognostic score based on the stored data; and (d) a port or readable interface for communicating the stored data and/or the prognostic score to a user.

In one example, the data processor comprises computer-executable mathematical algorithms (1)-(3) for calculating a Fibrosis Probability Score (FPS) that is correlated with a probability or likelihood that a subject will develop fibrosis and/or progress to a particular stage of fibrosis and/or progress rapidly to a late-stage fibrosis:

$$G = (C1*rs12979860) + (C2*rs8099917) + (C3*rs10211152) + (C4*rs4374383) + (C5*rs16851720) \quad (1)$$

$$Z = [X1 + G + (C6*age)] \quad (2)$$

$$FPS = 1 - [1/(1 + \exp(Z))] \quad (3)$$

wherein:

C1 is a coefficient for weighting applied to rs12979860 genotypes;

C2 is a coefficient for weighting applied to rs8099917 genotypes;

C3 is a coefficient for weighting applied to rs10211152 genotypes;

C4 is a coefficient for weighting applied to rs4374383 genotypes;

C5 is a coefficient for weighting applied to rs16851720 genotypes;

rs12979860=1.0 for a rs12979860-CC genotype, or −1.0 for a rs12979860-CT or rs12979860-TT genotype;

rs8099917=1.0 for a rs8099917-TT genotype, or −1.0 for a rs8099917-TG genotype or rs8099917-GG genotype;

rs10211152=1.0 for a rs10211152-CC genotype, or −1.0 for a rs10211152-TC genotype or rs10211152-TT genotype;

rs4374383=1.0 for a rs4374383-AG genotype, or 1.0 for a rs4374383-GG genotype, or −1.0 for a rs4374383-AA genotype;

rs16851720=1.0 for a rs16851720-AA genotype, or −1.0 for a rs16851720-AC genotype or a rs16851720-CC genotype;

a genotype that has not been determined is applied a null value subject to the proviso that data for at least one genotype for each of IL28B and MERTK must be present;

X1 represents an intermediate score;

C6 is a coefficient for weighting applied to age of subject; and age is in years.

In one example, the data processor may comprise computer-executable mathematical algorithms (1)-(3) for calculating a fibrosis probability score (FPS) that is correlated with fibrosis stage or a likelihood that a subject will develop fibrosis and/or progress to a particular stage of fibrosis and/or progress rapidly to a late-stage fibrosis:

$$G=(C1*rs12979860)+(C2*rs8099917)+(C3*rs10211152)+(C4*rs4374383)+(C5*rs16851720) \quad (1)$$

$$Z=[X1+G+(C6*age)] \quad (2)$$

$$FPS=1-1/[1+exp(Z)] \quad (3)$$

wherein:

exp(Z) is $e^Z$ wherein e is Euler's number;

C1 is a coefficient for weighting applied to rs12979860 genotypes;

C2 is a coefficient for weighting applied to rs8099917 genotypes;

C3 is a coefficient for weighting applied to rs10211152 genotypes or genotypes of a MERTK SNP in linkage disequilibrium with rs10211152 selected from the group consisting of rs10165940, rs10168067, rs10205793, rs13387346, rs13402707, rs13416895, rs2230517, rs6723289, rs6723394, rs6735717 and rs13396030;

C4 is a coefficient for weighting applied to rs4374383 genotypes; and

C5 is a coefficient for weighting applied to rs16851720 genotypes;

rs12979860=1.0 for a rs12979860-CC genotype, or −1.0 for a rs12979860-CT or rs12979860-TT genotype;

rs8099917=1.0 for a rs8099917-TT genotype, or −1.0 for a rs8099917-TG genotype or rs8099917-GG genotype;

rs10211152=1.0 for a rs10211152-CC genotype, or −1.0 for a rs10211152-TC genotype or rs10211152-TT genotype;

rs10165940=1.0 for a rs10165940-GG genotype, or −1.0 for a rs10165940-AG genotype or rs10165940-AA genotype;

rs10168067=1.0 for a rs10168067-CC genotype, or −1.0 for a rs10168067-CG genotype or rs10168067-GG genotype;

rs10205793=1.0 for a rs10205793-GG genotype, or −1.0 for a rs10205793-AG genotype or rs10205793-AA genotype;

rs13387346=1.0 for a rs13387346-CC genotype, or −1.0 for a rs13387346-CT genotype or rs13387346-TT genotype;

rs13402707=1.0 for a rs13402707-CC genotype, or −1.0 for a rs13402707-CT genotype or rs13402707-TT genotype;

rs13416895=1.0 for a rs13416895-CC genotype, or −1.0 for a rs13416895-CG genotype or rs13416895-GG genotype;

rs2230517=1.0 for a rs2230517-GG genotype, or −1.0 for a rs2230517-AG genotype or rs2230517-AA genotype;

rs6723289=1.0 for a rs6723289-CC genotype, or −1.0 for a rs6723289-AC genotype or rs6723289-AA genotype;

rs6723394=1.0 for a rs6723394-CC genotype, or −1.0 for a rs6723394-AT genotype or rs6723394-TT genotype;

rs6735717=1.0 for a rs6735717-AA genotype, or −1.0 for a rs6735717-AG genotype or rs6735717-GG genotype;

rs13396030=1.0 for a rs13396030-GG genotype, or −1.0 for a rs13396030-AG genotype or rs13396030-AA genotype;

rs4374383=1.0 for a rs4374383-AG genotype, or 1.0 for a rs4374383-GG genotype, or −1.0 for a rs4374383-AA genotype;

rs16851720=1.0 for a rs16851720-AA genotype, or −1.0 for a rs16851720-AC genotype or a rs16851720-CC genotype;

a genotype that has not been determined is applied a null value subject to the proviso that data for at least one genotype for each of IL28B and MERTK must be present;

X1 represents an intermediate score;

C6 is a coefficient for weighting applied to age of subject; and age is in years.

As used throughout this specification and in the accompanying claims, the term "exp(Z)" shall be understood to mean $e^Z$ i.e., $exp(Z)=e^Z$ wherein e is Euler's number or constant.

Conveniently, each of C1-05 in formula (1) has a value less than 1.0, and preferably a value less than 0.9 or less than 0.8 or less than 0.7 or less than 0.6. Preferably, each of C1-05 in formula (1) has a value in a range between 0.2 and 0.6, such that any one of C1-05 has a value of about 0.20 or about 0.21 or about 0.22 or about 0.23 or about 0.24 or about 0.24 or about 0.25 or about 0.26 or about 0.27 or about 0.28 or about 0.29 or about 0.3 or about 0.31 or about 0.32 or about 0.33 or about 0.34 or about 0.35 or about 0.36 or about 0.37 or about 0.38 or about 0.39 or about 0.4 or about 0.41 or about 0.42 or about 0.43 or about 0.44 or about 0.44 or about 0.45 or about 0.46 or about 0.47 or about 0.48 or about 0.49 or about 0.50 or about 0.51 or about 0.52 or about 0.53 or about 0.54 or about 0.55 or about 0.56 or about 0.57 or about 0.58 or about 0.59 or about 0.6. Even more preferably, C1 has a value in a range from about 0.51 to 0.53 including any number therein to four decimal places, and/or C2 has a value in a range from 0.30 to 0.53 including any number therein to four decimal places, and/or C3 has a value in a range from 0.34 to 0.36 including any number therein to four decimal places, and/or C4 has a value in a range from 0.21 to 0.29 including any number therein to four decimal places, and/or C5 has a value in a range from 0.13 to 0.29 including any number therein to four decimal places.

Conveniently, X1 in formula (2) has a value in a range from about −4 to about −7 including −4.0 or −4.1 or −4.2 or −4.3 or −4.4 or −4.5 or −4.6 or −4.7 or −4.8 or −4.9 or −5.0 or −5.1 or −5.2 or −5.3 or −5.4 or −5.5 or −5.6 or −5.7 or −5.8 or −5.9 or −6.0 or −6.1 or −6.2 or −6.3 or −6.4 or −6.5 or −6.6 or −6.7 or −6.8 or −6.9 or −7.0. Preferably, X1 has a value in a range from about −4.0 to about −5.0, and more preferably from about −4.3 to about −4.6 including about −4.3 or about −4.31 or about −4.32 or about −4.33 or about −4.34 or about −4.35 or about −4.36 or about −4.37 or about −4.38 or about −4.39 or about −4.4 or about −4.41 or about −4.42 or about −4.43 or about −4.44 or about −4.45 or about −4.46 or about −4.47 or about −4.48 or about −4.49 or about −4.5 or −4.51 or about −4.52 or about −4.53 or about −4.54 or about −4.55 or about −4.56 or about −4.57 or about −4.58 or about −4.59 or about −4.6, or any number in the stated range to four decimal places. In a particularly preferred example, X1 has a value of −4.3072 or −4.4513 or −4.5508 or −4.5643.

Conveniently, C6 has a value in a range from about 0.03 to about 0.07, including 0.03 or 0.035 or 0.04 or 0.045 or 0.05 or 0.055 or 0.06 or 0.065 or 0.07. Preferably, C6 has a value in a range from 0.03 to 0.04, or in a range from 0.035 to 0.038 including about 0.0351 or about 0.0352 or about 0.0353 or about 0.0354 or about 0.0355 or about 0.0356 or about 0.0357 or about 0.0358 or about 0.0359 or about 0.0360 or about 0.0361 or about 0.0362 or about 0.0363 or about 0.0364 or about 0.0365 or about 0.0366 or about 0.0367 or about 0.0368 or about 0.0369 or about 0.0370 or about 0.0371 or about 0.0372 or about 0.0373 or about 0.0374 or about 0.0375 or about 0.0376 or about 0.0377 or about 0.0378 or about 0.0379 or about 0.0380. In a particularly preferred example, C6 is 0.0362 or 0.0368 or 0.0373 or 0.0374.

In yet another example, a weighting is applied to SNP genotypes linked to MERTK and RNF7 loci, and a probability of developing fibrosis and/or progressing to a particular stage of fibrosis and/or progressing rapidly to a late-stage fibrosis is calculated using computer-executable mathematical algorithms (4)-(6):

$$G=(C1*rs12979860)+(C2*rs8099917)+[(C7*rs10211152*rs4374383)+(C8*rs16851720*rs4374383)] \quad (4)$$

$$Z=[X1+G+(C6*age)] \quad (5)$$

$$FPS=1-[1/(1+exp(Z))] \quad (6)$$

wherein:
C1 is a coefficient for weighting applied to rs12979860 genotypes;
C2 is a coefficient for weighting applied to rs8099917 genotypes;
C7 is a coefficient for weighting applied to the combination of rs10211152 and rs4374383 genotypes;
C8 is a coefficient for weighting applied to the combination of rs4374383 and rs4374383 genotypes;
rs12979860=1.0 for a rs12979860-CC genotype, or −1.0 for a rs12979860-CT or rs12979860-TT genotype;
rs8099917=1.0 for a rs8099917-TT genotype, or −1.0 for a rs8099917-TG genotype or rs8099917-GG genotype;
rs10211152=1.0 for a rs10211152-CC genotype, or −1.0 for a rs10211152-TC genotype or rs10211152-TT genotype;
rs4374383=1.0 for a rs4374383-AG genotype, or 1.0 for a rs4374383-GG genotype, or −1.0 for a rs4374383-AA genotype;
rs16851720=1.0 for a rs16851720-AA genotype, or −1.0 for a rs16851720-AC genotype or a rs16851720-CC genotype;
a genotype that has not been determined is applied a null value subject to the proviso that data for at least one genotype for each of IL28B and MERTK must be present;
X1 represents an intermediate score;
C6 is a coefficient for weighting applied to age of subject; and
age is in years.

In accordance with formulae (4)-(6), values of C1, C2, X1 and C6 are as indicated in the preceding paragraphs. Preferably, C7 and C8 each have a value less than 1.0, and preferably a value less than 0.9 or less than 0.8 or less than 0.7 or less than 0.6 or less than 0.5 or less than 0.4 or less than 0.3. Preferably, each of C7-C8 has a value in a range between 0.2 and 0.3, such that any one of C1-05 has a value of about 0.20 or about 0.21 or about 0.22 or about 0.23 or about 0.24 or about 0.24 or about 0.25 or about 0.26 or about 0.27 or about 0.28 or about 0.29 or about 0.3. Even more preferably, C7 and/or C8 is/are in a range from about 0.20 to about 0.30 including any number therein to four decimal places.

In yet another example, the genotyping assay determines combined genotypes at each of rs10211152, rs12979860 and rs16851720, and the data processor comprises computer-executable mathematical algorithms (7)-(9) for determining a probability of developing fibrosis and/or progressing to a particular stage of fibrosis and/or progressing rapidly to a late-stage fibrosis:

$$G=(0.5209*rs12979860)+(0.3572*rs10211152)+(0.1357*rs16851720) \quad (7)$$

$$Z=-4.5643+G+(0.0373*Age) \quad (8)$$

$$FPS=1-[1/(1+exp(Z))] \quad (9)$$

wherein:
rs12979860=1.0 for a rs12979860-CC genotype, or −1.0 for a rs12979860-CT or rs12979860-TT genotype;
rs10211152=1.0 for a rs10211152-CC genotype, or −1.0 for a rs10211152-TC genotype or rs10211152-TT genotype;
rs16851720=1.0 for a rs16851720-AA genotype, or −1.0 for a rs16851720-AC genotype or a rs16851720-CC genotype; and
age is in years.

In yet another example, the genotyping assay determines combined genotypes at each of rs10211152 and rs12979860, and the data processor comprises computer-executable mathematical algorithms (10)-(12) for for determining a probability of developing fibrosis and/or progressing to a particular stage of fibrosis and/or progressing rapidly to a late-stage fibrosis:

$$G=(0.5238*rs12979860)+(0.3488*rs10211152) \quad (10)$$

$$Z=-4.5508+G+(0.0374*Age) \quad (11)$$

$$FPS=1-[1/(1+exp(Z))] \quad (12)$$

wherein:
rs12979860=1.0 for a rs12979860-CC genotype, or −1.0 for a rs12979860-CT or rs12979860-TT genotype;
rs10211152=1.0 for a rs10211152-CC genotype, or −1.0 for a rs10211152-TC genotype or rs10211152-TT genotype; and
age is in years.

In yet another example, the genotyping assay determines combined genotypes at each of rs4374383 and rs12979860 and rs16851720, and the data processor comprises computer-executable mathematical algorithms (13)-(15) for for determining a probability of developing fibrosis and/or progressing to a particular stage of fibrosis and/or progressing rapidly to a late-stage fibrosis:

$$G=(0.5195*rs12979860)+(0.2115*rs4374383*rs16851720) \quad (13)$$

$$Z=-4.3072+G+(0.0368*Age) \quad (14)$$

$$FPS=1-[1/(1+exp(Z))]) \quad (15)$$

wherein:
rs12979860=1.0 for a rs12979860-CC genotype, or −1.0 for a rs12979860-CT or rs12979860-TT genotype;
rs4374383=1.0 for a rs4374383-AG genotype, or 1.0 for a rs4374383-GG genotype, or −1.0 for a rs4374383-AA genotype;
rs16851720=1.0 for a rs16851720-AA genotype, or −1.0 for a rs16851720-AC genotype or a rs16851720-CC genotype; and
age is in years.

In yet another example, the genotyping assay determines combined genotypes at each of rs4374383 and rs12979860, and the data processor comprises computer-executable mathematical algorithms (16)-(18) for determining a probability of developing fibrosis and/or progressing to a particular stage of fibrosis and/or progressing rapidly to a late-stage fibrosis:

$$G=(0.5199*rs12979860)+(0.2857*rs4374383) \quad (16)$$

$$Z=-4.4513+G+(0.0362*\text{Age}) \quad (17)$$

$$\text{FPS}=1-[1/(1+\exp(Z))] \quad (18)$$

wherein:

rs12979860=1.0 for a rs12979860-CC genotype, or −1.0 for a rs12979860-CT or rs12979860-TT genotype;

rs4374383=1.0 for a rs4374383-AG genotype, or 1.0 for a rs4374383-GG genotype, or −1.0 for a rs4374383-AA genotype; and age is in years.

The device and algorithms for calculating integer Z according to any example herein above is conveniently modified to record one or more additional data points relevant to calculation of a likelihood or probability of developing fibrosis and/or progressing to a particular stage of fibrosis and/or progressing rapidly to a late-stage fibrosis. For example, one or more non-genetic factors relevant to liver fibrosis e.g., a level of gamma-glutamyl transferase (GGT) enzyme and/or a level of aspartate aminotransferase (AST) enzyme and/or a level of bilirubin and/or platelet count are useful in determining fibrosis. Elevated GGT level suggests hepatic disease, acute pancreatitis, renal disease, or alcohol in the liver. Elevated AST suggests viral hepatitis e.g., when the ratio of ALT:AST is elevated, biliary tract obstruction (cholangitis, choledocholithiasis), alcoholic hepatitis, or end-stage fibrosis e.g., when a ratio of AST:ALT is elevated. Elevated bilirubin suggests acute or chronic hepatitis, cirrhosis, biliary tract obstruction, toxic hepatitis, congenital liver enzyme abnormalities (Dubin-Johnson, Rotor's, Gilbert's, Crigler-Najjar syndromes), or hepatotoxicity. Accordingly, it is within the scope of the invention to modify the algorithms by addition of factors taking account of GGT and AST and bilirubin and platelet count. It is to be understood that a determination of each of AST, GGT, Bilirubin and platelets is optional and when not determined, the value ascribed to each non-determined integer is zero. When determined, the value ascribed to each of AST, GGT, Bilirubin and platelets is an art-recognized assay unit of measurement. For example, AST and GGT may be expressed in activity units per unit volume of serum or as a ratio of an upper limit of normal activity (ULN), whereas platelets may be expressed as cell number per unit volume of serum (N) e.g., (N×10$^9$ per liter), and bilirubin may be expressed as a weight per unit volume e.g., mg/dL or mg/liter.

In one example, formula (2) is modified to formula (19) as follows:

$$Z=[X1+G+(C6*\text{age})+(C7*\text{AST})+(C8*\text{GGT})+(C9*\text{Bilirubin})-(C10*\text{platelets})] \quad (19)$$

wherein:

C7 is a coefficient for weighting applied to AST levels having a value between about 0.004 and about 0.5, including a value in a range from 0.00427 to 0.0046;

C8 is a coefficient for weighting applied to GGT levels having a value between about 0.0026 and about 0.0028, including a value in a range from 0.00263 to 0.00279;

C9 is a coefficient for weighting applied to bilirubin levels having a value between about 0.024 and about 0.026, including a value in a range from 0.0246 to 0.0255;

C10 is a coefficient for weighting applied to platelet levels having a value between about 0.0052 and about 0.0055, including a value in a range from 0.00526 to 0.0054;

each of AST, GGT, Bilirubin and platelets is optional and when not determined, AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum (N) e.g., (N×10$^9$ per liter); and bilirubin when present is expressed as a weight per unit volume serum e.g., mg/dL or mg/liter. In accordance with this example, G is calculated as in formula (1), X1, C6 and Age are each as in formula (2), and FPS is calculated in accordance with formula (3) from the variable Z according to formula (19).

In another example, formula (8) is modified to formula (20) as follows:

$$Z=-4.5643+G+(0.0373*\text{Age})+(0.00429*\text{AST})+(0.00267*\text{GGT})+(0.0252*\text{Bilirubin})-(0.0054*\text{platelets}) \quad (20)$$

wherein:

AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum (N) e.g., (N×10$^9$ per liter); and bilirubin when present is expressed as a weight per unit volume serum e.g., mg/dL or mg/liter. In accordance with this example, G is calculated as in formula (7), X1, C6 and Age are each as in formula (8), and FPS is calculated in accordance with formula (9) from the variable Z according to formula (20). As exemplified herein, and shown in FIG. 7, an assay performed in accordance with this example provides FPS values which, when analyzed by ROC, have an AUC of 0.815.

In another example, formula (11) is modified to formula (21) as follows:

$$Z=-4.5508+G+(0.0374*\text{Age}))+(0.00427*\text{AST})+(0.00263*\text{GGT})+(0.0249*\text{Bilirubin})-(0.00526*\text{platelets}) \quad (21)$$

wherein:

AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum (N) e.g., (N×10$^9$ per liter); and bilirubin when present is expressed as a weight per unit volume serum e.g., mg/dL or mg/liter. In accordance with this example, G is calculated as in formula (10), X1, C6 and Age are each as in formula (11), and FPS is calculated in accordance with formula (12) from the variable Z according to formula (21). As exemplified herein, an assay performed in accordance with this example provides FPS values which, when analyzed by ROC, have an AUC of 0.7916.

In another example, formula (14) is modified to formula (22) as follows:

$$Z=-4.3072+G+(0.0368*\text{Age})+(0.00452*\text{AST})+(0.00279*\text{GGT})+(0.0255*\text{Bilirubin})-(0.00538*\text{platelets}) \quad (22)$$

wherein:

AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum (N) e.g., (N×10$^9$ per liter); and bilirubin when present is expressed as a weight per unit volume serum e.g., mg/dL or mg/liter. In accordance with this example, G is calculated as in formula (13), X1, C6 and Age are each as in formula (14), and FPS is calculated in accordance with formula (15) from the variable Z according to formula (22). As exemplified herein, an assay performed in accordance with this example provides FPS values which, when analyzed by ROC, have an AUC of 0.804.

In another example, formula (17) is modified to formula (23) as follows:

$$Z=-4.4513+G+(0.0362*Age)+(0.0046*AST)+ \\ (0.00269*GGT)+(0.0246*Bilirubin)- \\ (0.00528*platelets) \qquad (23)$$

wherein:

AST when present is expressed in activity units per unit volume of serum or as a ratio of an upper limit of normal activity (ULN);

GGT when present is expressed in activity units per unit volume of serum or as a ratio of an upper limit of normal activity (ULN);

platelets when present are expressed as cell number per unit volume of serum (N) e.g., (N×10$^9$ per liter); and bilirubin when present is expressed as a weight per unit volume serum e.g., mg/dL or mg/liter. In accordance with this example, G is calculated as in formula (16), X1, C6 and Age are each as in formula (17), and FPS is calculated in accordance with formula (18) from the variable Z according to formula (23). As exemplified herein, an assay performed in accordance with this example provides FPS values which, when analyzed by ROC, have an AUC of 0.7817.

This invention also provides a system for managing treatment of fibrosis or a medical condition associated with progression of fibrosis, said system comprising a computer comprising:

(a) an input interface configured to receive prognostic score data for a subject having early-stage fibrosis or a medical condition associated with onset of fibrosis, wherein the data are generated by the device according to any example hereof, and wherein a plurality of data points are collected over a time course before commencement of therapy and/or during therapy and/or following cessation of therapy collected over time;

(b) an input interface configured to receive data indicating a medical condition associated with onset or progression of fibrosis in the subject and whether therapy is to treat the medical condition and/or the fibrosis;

(c) a reference database of therapies for fibrosis and medical conditions associated with fibrosis;

(d) a computer-readable storage medium for storing the data received at (a) and (b) and (c);

(e) a data processor that is executed to calculate a prognostic score based on the stored data;

(f) a processor for calculating a preferred therapy based on the stored data at (a) and (b) and (c); and (g) a port or readable interface for communicating the preferred therapy calculated by the processor to a user.

The computer and the device may be configured to be in communication with each other to facilitate transfer of prognostic score data from the device to the computer. For example, the computer and the device may be in wired communication with each other, or alternatively, in wireless communication with each other.

Alternatively, the computer and the device may not be configured to be in the same network. For example, prognostic score data may be input to the computer following their determination remotely using the device. This may means transferring the prognostic score data to the computer from a computer-readable medium, or inputting prognostic score data manually to the computer.

The system and device of the present invention have particular utility in monitoring therapy e.g., monitoring the efficacy of therapy for fibrosis or a medical condition associated with progression of liver fibrosis. In such applications, the system according to any example hereof may be implemented on a subject undergoing treatment for fibrosis or a condition associated therewith and therapy modified according to the prognostic score data obtained over time.

The skilled artisan will appreciate that, unless the context requires otherwise, the present invention according to any example described herein is suitable for predicting a likelihood or probability that fibrosis will occur in a subject having a medical condition associated with onset of fibrosis, and for predicting a stage to which fibrosis will progress, as well as for predicting a likelihood or probability that fibrosis, once commenced in a subject, will advance rapidly from early stage to a late stage. Unless the context requires otherwise, the present invention according to any example hereof is also useful in a diagnostic context, for staging fibrosis and or stratifying patients according to their stage of fibrosis e.g., early stage or late stage or substantial fibrosis or no detectable fibrosis. For example, the cohorts described herein include subjects at different stages of fibrosis and are stratified inter alia according to the severity of their fibrosis and genotype. Moreover, a subject who does not have a genetic predisposition to progress rapidly to late stage fibrosis is less likely during a fixed period of time from diagnosis to progress beyond an early stage of fibrosis than a subject having a genetic predisposition to progress rapidly to late stage fibrosis. Accordingly, the methods and means provided herein are suitable for both diagnosis and prognosis, including diagnosis of stage and prediction of fibrosis stage over time and fibrosis progression rate in a subject. For example, the same coefficients are applied in the algorithms described herein for predicting fibrosis stage and fibrosis rate in a subject. virtually the same) as it predicts fibrosis rate.

The invention is described further with reference to the following working examples.

Example 1

Patient Cohorts
Chronic HCV-Infected Subjects (CHC Cohort)

A cohort of 1000 Caucasian subjects having chronic hepatitis C virus (HCV) infection, all of whom had a liver biopsy that produced a Metavir fibrosis stage, and disease activity before treatment between 1999 and 2011, was included. Patients were excluded if they had evidence of other liver diseases by standard tests.
NAFLD Cohort A cohort of 502 consecutive patients with NAFLD and fulfilling all inclusion and exclusion criteria detailed below, was assessed.

Inclusion criteria were: (1) availability of blood samples for genetic analyses; and (2) histological diagnosis of NAFLD on a liver biopsy done less than 6 months before enrollment. The diagnosis of NAFLD was based on chronically elevated ALT for at least 6 months, alcohol consumption <20 g/day in the year before liver biopsy and evaluated by a questionnaire, and steatosis (>5% of hepatocytes) at histology with or without necroinflammation, and/or fibrosis.

Exclusion criteria were: (1) hepatocellular carcinoma; (2) other causes of liver disease or mixed etiologies (excessive alcohol consumption, hepatitis C, hepatitis B, autoimmune liver disease, Wilson's disease, hemochromatosis, α1-antitrypsin deficiency); (3) human immunodeficiency virus infection; (4) previous treatment with antiviral therapy, immunosuppressive drugs, and/or regular use of steatosis-inducing drugs, evaluated by interview; (5) therapy with medications known to affect uric acid (UA) metabolism; and (7) active intravenous drug addiction.

Chronic Hepatitis B Virus-Infected Subjects (CHB Cohort)

600 CHB patients that had been HBsAg-positive for more than 6 months and were untreated for HBV infection, and had a liver biopsy with scoring for Metavir fibrosis stage and disease activity before treatment, were included.

Patients with hepatitis C virus (HCV), hepatitis delta virus (HDV), and human immunodeficiency (HIV) virus coinfections, other concomitant liver diseases, current or previous hepatic decompensation, current or previous antiviral treatment, and/or an absolute contraindications to liver biopsy (platelets, <60×109/L; INR>1.35) were excluded.

Idiopathic Pulmonary Fibrosis (IPF) Cohort

Patients with IPF satisfy the following inclusion criteria. Mean age at the time of presentation is about 48-72 years including males and females, but predominantly male. Patients may have a familial form of the disease with diagnosis at 35-67 years of age. Patients suffer from dyspnoea, cough, basal crepitations and clubbing of the nails. Lung function tests reveal restrictive lung function impairment and a reduced diffusing capacity. IPF diagnosis is confirmed histologically by open lung biopsy, revealing a pattern of usual interstitial pneumonia (UIP). Patients have been receiving therapy comprising corticosteroids, optionally in combination with an immunosuppressant such as azathioprine or cyclophosphamide. Patients may be eligible for lung transplantation or have had lung transplantation. Cases with only a radiographic diagnosis of an interstitial lung disease are excluded.

Chronic Kidney Disease Cohort

Patients satisfy the following inclusion criteria: Adult patients aged at least 20 years and undergoing percutaneous needle kidney biopsy for nephrotic syndrome, nephritis, or unexplained renal failure and having one or more reasons for renal biopsy, such as cellular casts in urine for more than 3 months, and/or a daily protein excretion rate of more than 1 □ gram for more than 3 months, or kidney injury of unknown origin and not due to prerenal azotemia, nephrotoxic agents, septicemia, or local kidney infections, or urinary tract obstruction. Exclusion criteria are dialysis patients or renal transplant recipients, active malignancy, rare kidney diseases including Alport's syndrome, lipoprotein glomerulopathy, thin basement membrane disease and immunotactoid glomerulopathy. Control groups comprise subjects receiving nephrectomy for localized circumscribed kidney tumor, and having normal renal function and no other significant comorbidities.

Liver Histopathology

Biopsies were interpreted by a single expert liver pathologist in each center who was blinded to patient clinical characteristics, serum measurements and IL28B genotyping. All biopsies had a minimum length of 15 mm or the presence of at least 11 complete portal tracts; inadequate biopsies were excluded as described by Colloredo et al., *J Hepatol.* 39, 239-244, 2003.

Liver histopathology for cases with CHC or CHB was according to METAVIR (Bedossa et al., *Hepatology* 24, 289 (1996). Fibrosis was staged from F0 (no fibrosis) to F4 (cirrhosis).

Necroinflammation (A) was graded as A0 (absent), A1 (mild), A2 (moderate), or A3 (severe).

For NAFLD, the Kleiner classification was used to compute the non-alcoholic fatty liver disease activity (NAS) score (from 0 to 8, on a scale including separate scores for steatosis, lobular inflammation, and hepatocellular ballooning), and to stage fibrosis from 0 to 4 (Kleiner et al., *Hepatology* 41, 1313-1321, 2005).

Kidney Histopathology

Formalin-fixed, paraffin-embedded kidney biopsy specimens of CKD patients and normal kidney tissues of control subjects are sectioned in 4 □m and stained with hematoxylin and eosin for histological examination. To determine the percentage of interstitial fibrosis, sections are stained with a Masson's trichrome kit (Accustain, Sigma-Aldrich, St Louis, Mo., USA) according to the manufacturer's instructions. The percentage of global obsolescence of glomeruli and the severity of tubulointerstitial injury are examined under 20 randomly selected high-power fields (×400). Glomerulosclerosis is determined using a percentage of glomeruli expressing global or segmental sclerosis. Tubular damage, fibrosis and inflammatory cell infiltration in cortical interstitium are graded by a scoring system from 0 to 4 (0, no changes; 1, changes affecting <25%; 2, changes affecting 25-50%; 3, changes affecting 50-75%; and 4, changes affecting >75% of the cortical parenchyma), such as described by Lin et al., *J. Am. Soc. Nephrol.* 16, 2702-2713. 2005 or Lee et al., *Cell Transplant* 21, 2569-2585, 2012. Sections are analyzed by a pathologist blinded from clinical or laboratory data on patients.

Lung Histopathology

Formalin-fixed, paraffin-embedded surgical lung biopsy (SLB) specimens of IPF patients and normal lung tissues of control subjects are sectioned in 4 □µm and stained with hematoxylin and eosin for histological examination. Target areas for biopsy are selected on the basis of HRCT features and discussed with the radiologist. Ideally, biopsy specimens are taken from areas that are intermediate in degree of fibrosis, i.e., not from most fibrotic areas or from normal areas, and from multiple lobes of patients. For patients having both lungs equally affected, SLB is commonly performed in the left lung, because lung margins are thinner and easy to resect, and because right lung is usually dominant functionally.

Genotyping

Genotyping of cohort samples for IL28B rs8099917 and MERTK rs4374383 SNPs was undertaken using the TaqMan SNP genotyping allelic discrimination method (Applied Biosystems, Foster City, Calif., USA). The rs8099917 genotyping kit was supplied by Applied Biosystems and rs12979860 genotyping was performed using a custom designed genotyping assay from Applied Biosystems. Genotyping was performed using the StepOne RT system and analyzed with StepOne software v.2.3.0 (Applied Biosystems, Foster City, Calif., USA). All genotyping was undertaken blinded to clinical variables.

Genotyping of cohort samples for IL28B rs12979860, MERTK rs10211152, and RNF7 rs16851720 was performed using Sequenom Autoflex Mass Spectrometer. After submission of SNP details, PCR oligonucleotides were designed and applied to the DNA samples were genotyped using the Sequenom MassARRAY system and iPLEX Gold chemistry.

Determination of Fibrosis Progression Rate

The fibrosis progression rate (FPR) was determined by calculating the ratio between the fibrosis stage and the estimated disease duration (in years). Two approaches were used to assess fibrosis progression.

First, patients were stratified into two groups of stage-constant FPRs according to the median rate (i.e., 0.076 fibrosis units/year), which was used as a cutoff. Factors associated with rapid FPR (i.e., higher than a median progression rate) were analyzed by univariate and multivariate regression analysis.

Second, Cox regression analysis was employed to model the time taken for significant fibrosis (Metavir Stage F2 or F3 or F4) to occur. After checking the normality of the quantified variables, appropriate logarithmic transformations were made. A Cox proportional-hazards regression model was fitted, and the covariates were considered significant if $P<0.05$. The proportional hazard assumption was checked and a final model was proposed, considering only the significant terms. Univariate and multivariate Cox-regression was used to explore the possible predictors of significant fibrosis.

Non-Additive Interaction Between IL28B and MERTK Genotypes in Rapid Progression of Fibrosis Patients in one or more cohorts described herein are graded with respect to the extent of fibrosis in the relevant organ i.e., liver, kidney or lung, and the extent of fibrosis and rate of progression of fibrosis from the time of diagnosis are scored. Patient SNP genotypes linked to IL28B and MERTK were determined and correlated to extent of fibrosis and fibrosis progression rate for patients in the one or more cohorts.

By way of a non-limiting example, data are provided herein for progression of liver fibrosis based on data obtained from the CHC cohort.

A summary of the associations of different IL28B SNPs with fibrosis progression when considered alone, or in combination with the MERTK SNP rs4374383 in a sample of subjects from the cohorts (n=400), is presented in Table 1. The data indicate that, of the SNPs indicated, only the combination of IL28B SNP rs12979860 and MERTK SNP rs4374383 or the combination of IL28B SNP rs8099917 and MERTK SNP rs4374383 provide a strong correlation with fibrosis progression (data not shown).

TABLE 1

| SNP | OR (95% CI) (single SNP) | P value (single SNP) | OR (95% CI) (IL28B SNP + rs4374383) | P value (combination) |
|---|---|---|---|---|
| MERTK rs4374383 | 1.89 | <0.0001 | | |
| IL28B rs12979860 | 2.17 | <0.0001 | 4.61 | <0.001 |
| IL28B rs8099917 | 1.55 | <0.0001 | 3.0 | <0.0001 |
| IL28B rs1297980275 | 1.38 | 0.07 | 2.28 | 0.4 |
| IL28B rs1503391 | 1.37 | 0.2 | 1.81 | 0.4 |
| IL28B rs17461620 | 1.33 | 0.2 | 1.53 | 0.6 |
| IL28B rs1931704 | 1.96 | 0.1 | 2.61 | 0.1 |
| IL28B rs2066911 | 1.32 | 0.2 | 2.88 | 0.1 |
| IL28B rs3033390 | 1.13 | 0.6 | 2.83 | 0.02 |
| IL28B rs926494 | 1.67 | 0.1 | 2.4 | 0.02 |

TABLE 1-continued

| SNP | OR (95% CI) (single SNP) | P value (single SNP) | OR (95% CI) (IL28B SNP + rs4374383) | P value (combination) |
|---|---|---|---|---|
| IL28B rs557905 | 1.37 | 0.2 | 2.07 | 0.3 |
| IL28B rs6806020 | 1.35 | 0.2 | 2.85 | 0.1 |
| IL28B rs7512595 | 1.29 | 0.4 | 2.4 | 0.4 |
| IL28B rs1503391 | 1.37 | 0.2 | 1.81 | 0.4 |

For reciprocal analysis, a summary of the associations of different MERTK SNPs with risk of late-stage liver fibrosis when considered alone, or in combination with the IL28B SNP rs12979860 in a sample of subjects from the cohorts is presented in Table 2. Sample size (n) for most analyses was 1000, except for data on rs12979860 alone and the combination of rs12979860 and rs4374383 which are taken from Table 1 for completeness. The data indicate that, of the SNPs indicated, only the combination of IL28B SNP rs12979860 and MERTK SNP rs10211152 and the combination of IL28B SNP rs12979860 and MERTK SNP rs4374383 provide a strong correlation with fibrosis progression. Of these, rs10211152 is more likely to be a causative SNP associated with liver fibrosis progression and/or liver fibrosis progression rate.

TABLE 2

| SNP | OR (95% CI) (single SNP) | P value (single SNP) | OR (95% CI) (MERTK + rs12979860) | P value (combination) |
|---|---|---|---|---|
| IL28B rs12979860 | 2.17 | <0.0001 | | |
| MERTK rs10211152 | 2.82 | <0.0001 | 7.4 | <0.0001 |
| MERTK rs4374383 | 1.89 | <0.0001 | 4.61 | <0.001 |
| MERTK rs11685190 | 1.44 | 0.1 | 3.48 | 0.001 |
| MERTK rs13404771 | 1.34 | 0.1 | 3.51 | <0.0001 |
| MERTK rs2230515 | 1.18 | 0.1 | 3.73 | <0.0001 |
| MERTK rs10185747 | 1.27 | 0.1 | 3.13 | <0.0001 |
| MERTK rs10195619 | 1.19 | 0.1 | 3.78 | <0.0001 |
| MERTK rs10496440 | 1.21 | 0.2 | 3.17 | <0.0001 |
| MERTK rs13016143 | 1.04 | 0.7 | 2.45 | <0.0001 |
| MERTK rs17175626 | 1.28 | 0.3 | 4.19 | 0.003 |
| MERTK rs34787974 | 1.37 | 0.2 | 4 | <0.0001 |
| MERTK rs6748256 | 1.46 | 0.01 | 4.22 | <0.0001 |
| MERTK rs9937047 | 1.21 | 0.3 | 2.19 | 0.003 |

Collectively, the data presented in Tables 1-2 provide solid evidence for interaction between specific IL28B and MERTK SNP genotypes, in particular rs12979860, rs8099917, rs10211152 and rs4374383, in their association with susceptibility to significant liver fibrosis or late-stage liver fibrosis and/or liver fibrosis progression and/or liver fibrosis progression rate.

Figure 2:
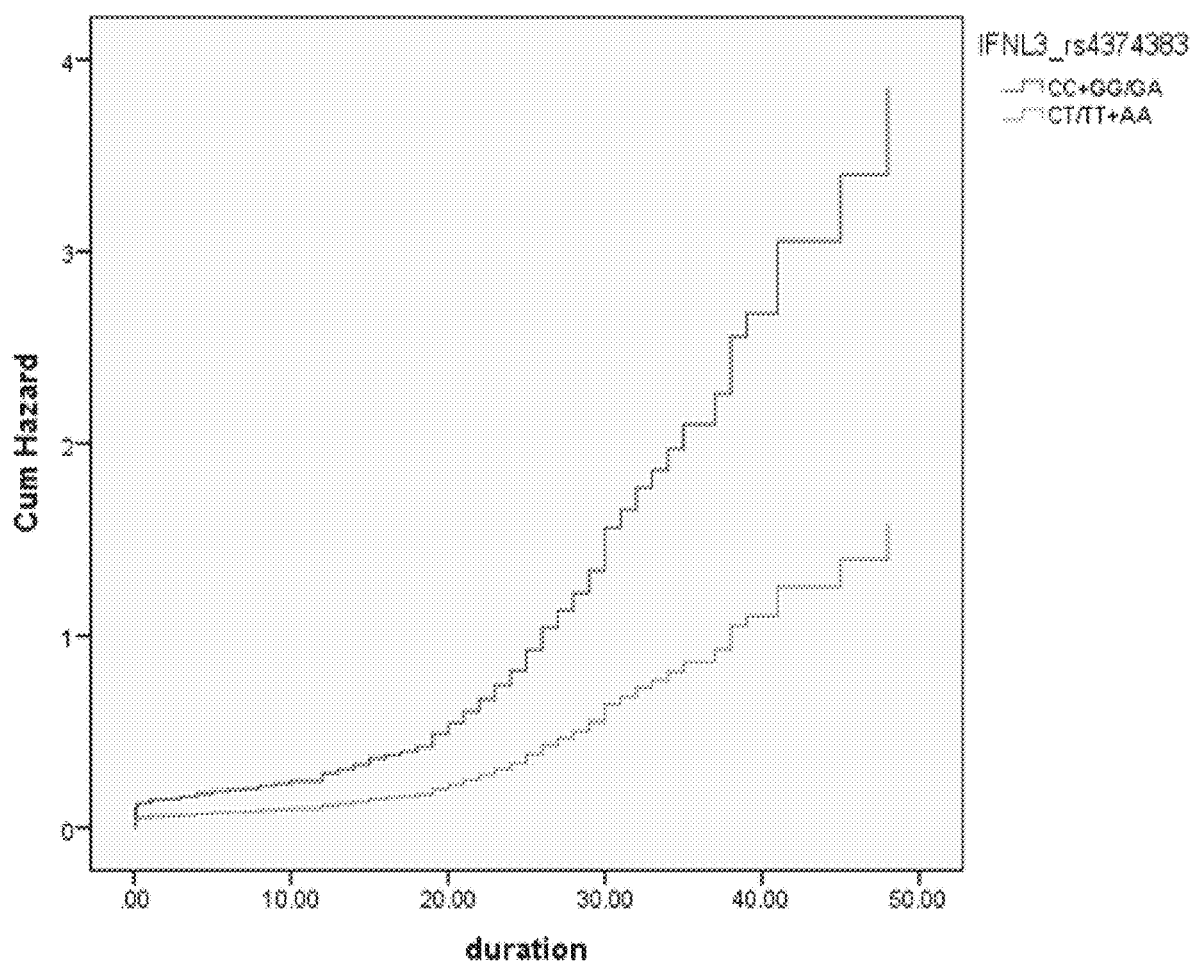
FIG. 2 is a graphical representation showing the cumulative Cox proportional-hazard regression for progression of liver fibrosis in subjects having chronic HCV-infection (y-axis), based on their duration of infection in years (x-axis), and stratified according to their combined genotypes at rs12979860 and rs4374383. The combined genotypes indicated in the figure are rs12979860-CC and rs4374383-AG/GG ("CC+GG/GA"; upper curve), and the alternate combined genotype rs12979860-CT/TT and rs4374383-AA ("CT/TT+AA"; lower curve).

Data provided in FIG. 1 show the cumulative probability of progression of liver fibrosis in subjects having chronic HCV-infection based on their ages at the time of infection, and stratified according to their combined genotypes at rs12979860 and rs4374383. The data show that the probability of progression to late-stage liver fibrosis i.e., Metavir Stage F2/F3/F4, is elevated in persons having the rs12979860-CC and/or the rs4374383-AG/GG genotypes, and that such persons are at higher risk of developing end-stage fibrosis relative to those persons having the alternative genotypes at these loci, especially when the subjects are older than about 20 years of age at the time of infection with HCV. The risk of developing late-stage fibrosis is also shown to increase with age from about 20 years of age, with the effect of genotype also increasing with age at the time of infection. Persons having the combined rs12979860-CC and rs4374383-AG/GG genotype are at higher risk across all age groups from about 20 years at the time of infection onwards. Thus, the combined effect of age and genotype influences pathology of liver fibrosis in HCV-infected subjects. The population sample consisted of 1000 Caucasian subjects having chronic HCV infection. Similarly, data provided in FIG. 2 show that the risk of progression to significant liver fibrosis i.e., Metavir Stage F2 or F3 or F4 in a cohort of 1000 subjects having chronic HCV infection, is elevated in persons having the combined rs12979860-CC and rs4374383-AG/GG genotype. The risk of developing late-stage fibrosis is also shown to over time. The data are consistent with a non-additive interaction between rs12979860-CC and rs4374383-AG/GG genotypes that is associated with progression to significant liver fibrosis, including late-stage liver fibrosis, in subjects having chronic HCV infection.

Figure 4:
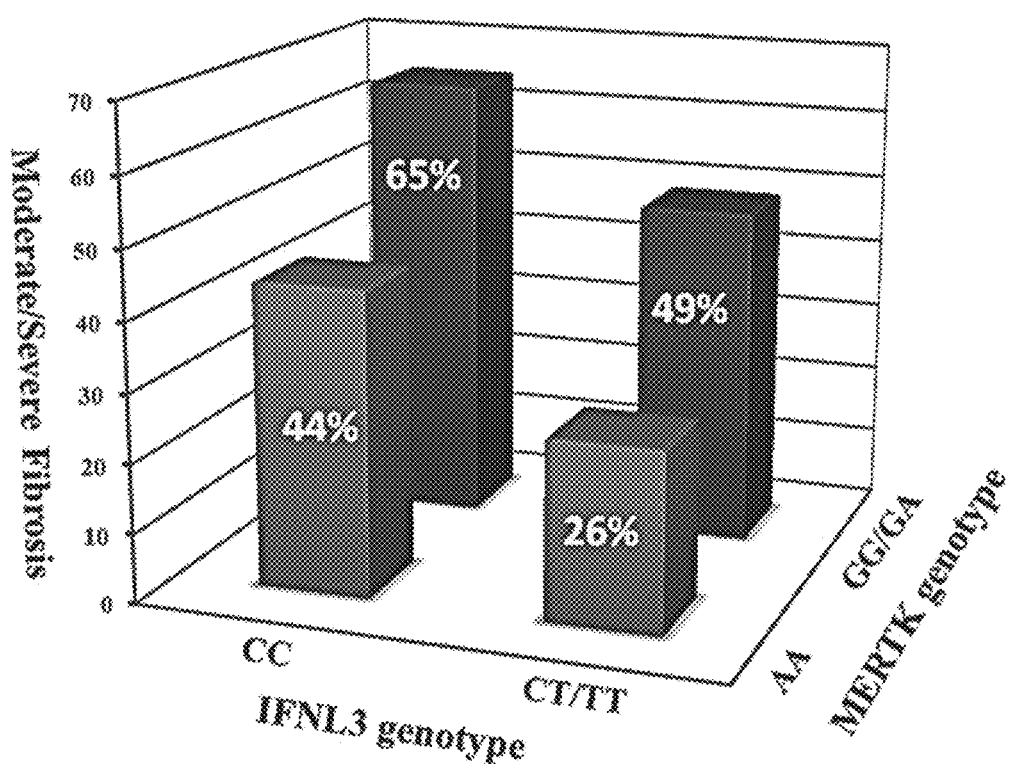
FIG. 4 is a graphical representation showing the stratification of subjects developing late-stage liver fibrosis i.e., Metavir Stage F2-F4 (termed "moderate/severe fibrosis" in the figure) according to their combined genotypes at rs12979860 and rs4374383. The IL28B genotypes (shown as "IFNL3 genotype" in the figure) are rs12979860-CC ("CC") and rs12979860-CT/TT ("CT/TT"), and the MERTK genotypes are rs4374383-AG/GG ("GG/GA") and rs4374383-AA ("AA").
Figure 5:
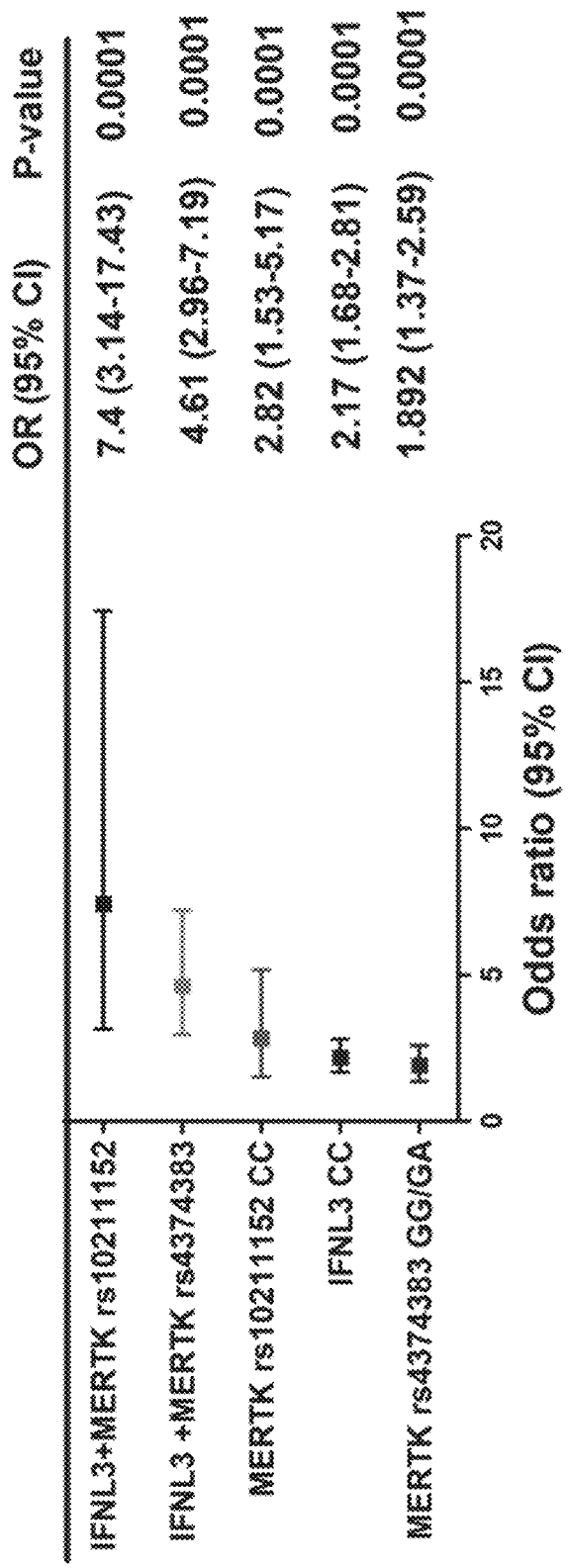
FIG. 5 is a graphical representation showing the non-additive interaction between the IL28B genotype rs12979860-CC ("IFNL3 CC" or "IFNL3" in the figure) and either (i) the MERTK genotype rs4374383-AG/GG ("MERTK rs4374383 GG/GA" or "MERTK rs4374383" in the figure) or (ii) the MERTK genotype rs10211152-CC (MERTK rs10211152 CC" or "MERTK rs10211152" in the figure). The likelihoods, as determined by Odds Ratio (OR) at the 95% confidence interval (95% CI), that subjects carrying one of each genotype or both genotypes are at risk of late-stage liver fibrosis, are shown in the figure. Statistical significance of the data (p<0.0001) is also shown.

The inventors also stratified subjects in the primary HCV cohort or 1000 subjects that developed significant fibrosis i.e., Metavir Stage F2/F3/F4 according to their combined genotypes at rs12979860 and rs4374383. Data shown in FIG. 4 indicate that amongst subjects progressing to exhibit significant fibrosis or late-stage liver fibrosis, 65% have the combined rs12979860-CC and rs4374383-AG/GG genotype, 44% have the combined rs12979860-CC and rs4374383-AA genotype, 49% have the combined rs12979860-CT/TT and rs4374383-AG/GG genotype, and only 26% have the combined rs12979860-CT/TT and rs4374383-AA genotype. Data support the association of rs12979860-CC and rs4374383-AG/GG genotypes with late-stage liver fibrosis and with progression of liver fibrosis e.g., in HCV-infected subjects. The likelihoods, as determined by Odds Ratio (OR) at the 95% confidence interval (95% CI), that subjects carrying the IL28B genotype rs12979860-CC and/or the MERTK genotype rs4374383-AG/GG will progress to late-stage liver fibrosis, is shown in FIG. 5. Thus, there is a strong correlation, which is consistent with a non-additive interaction, between the combined rs12979860-CC and rs4374383-AG/GG genotype and late-stage liver fibrosis in subjects having chronic HCV infection.

Figure 3:
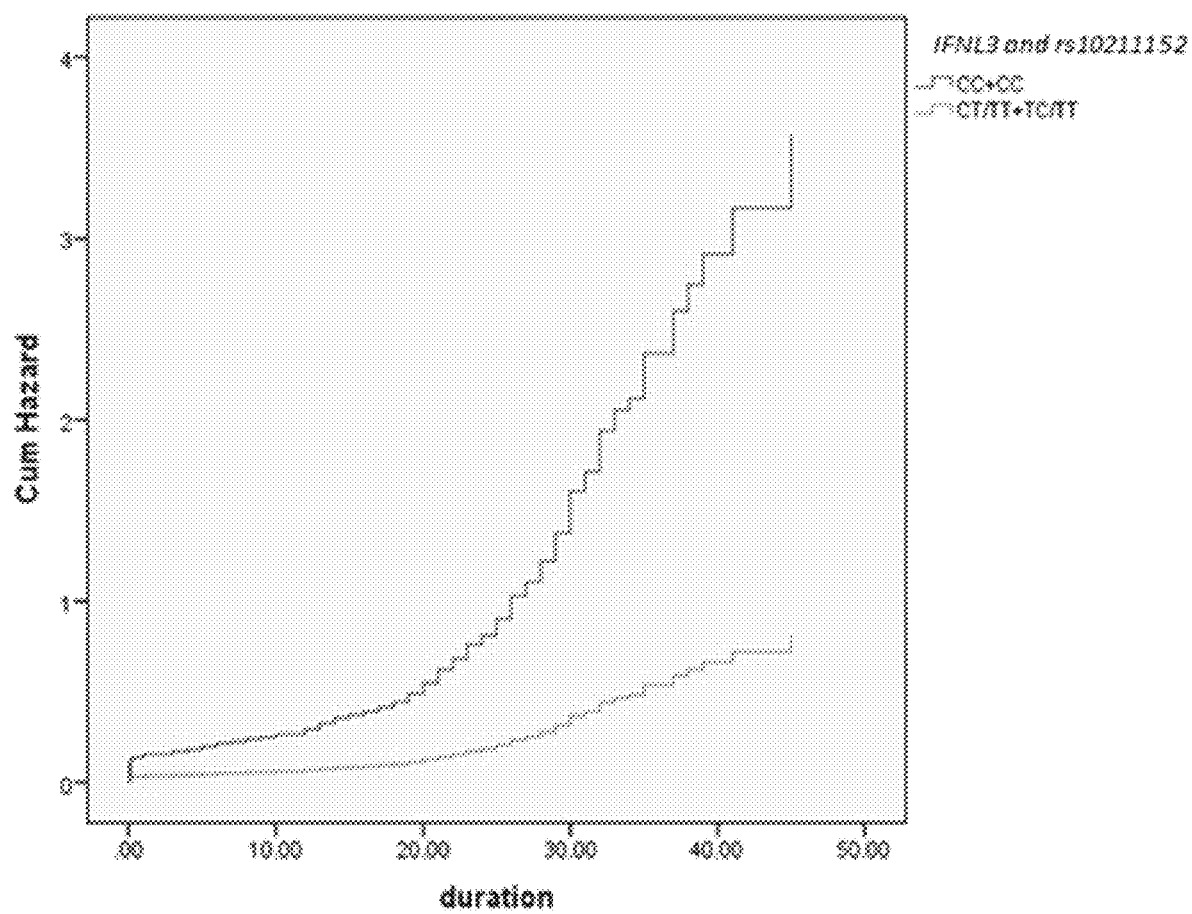
FIG. 3 is a graphical representation showing the cumulative Cox proportional-hazard regression for progression of liver fibrosis in subjects having chronic HCV-infection (y-axis), based on their duration of infection in years (x-axis), and stratified according to their combined genotypes at rs12979860 and rs10211152. The combined genotypes indicated in the figure are rs12979860-CC and rs10211152-CC ("CC+CC"; upper curve), and the alternate combined genotype rs12979860-CT/TT and rs10211152-TC/TT ("CT/TT+TC/TT"; lower curve).

Using a cohort of 1000 subjects with chronic HCV infection, the inventors produced cumulative Cox proportional-hazard regression for progression of liver fibrosis in subjects having chronic HCV-infection, based on their duration of infection in years, and stratified according to their combined genotypes at rs12979860 and rs10211152 i.e., the diagnostic/prognostic combined genotype rs12979860-CC and rs10211152-CC, and the alternate combined genotype rs12979860-CT/TT and rs10211152-TC/TT. Data presented in FIG. 3 show that the risk of progression to significant liver fibrosis i.e., Metavir Stage F2-F4, is elevated in persons having the combined rs12979860-CC and rs10211152-CC genotype. The risk of developing late-stage fibrosis is also shown to increase over time. The data are consistent with a non-additive interaction between rs12979860-CC and rs10211152-CC genotypes that is associated with progression to significant liver fibrosis, including late-stage liver fibrosis, in subjects having chronic HCV infection.

Figure 6:
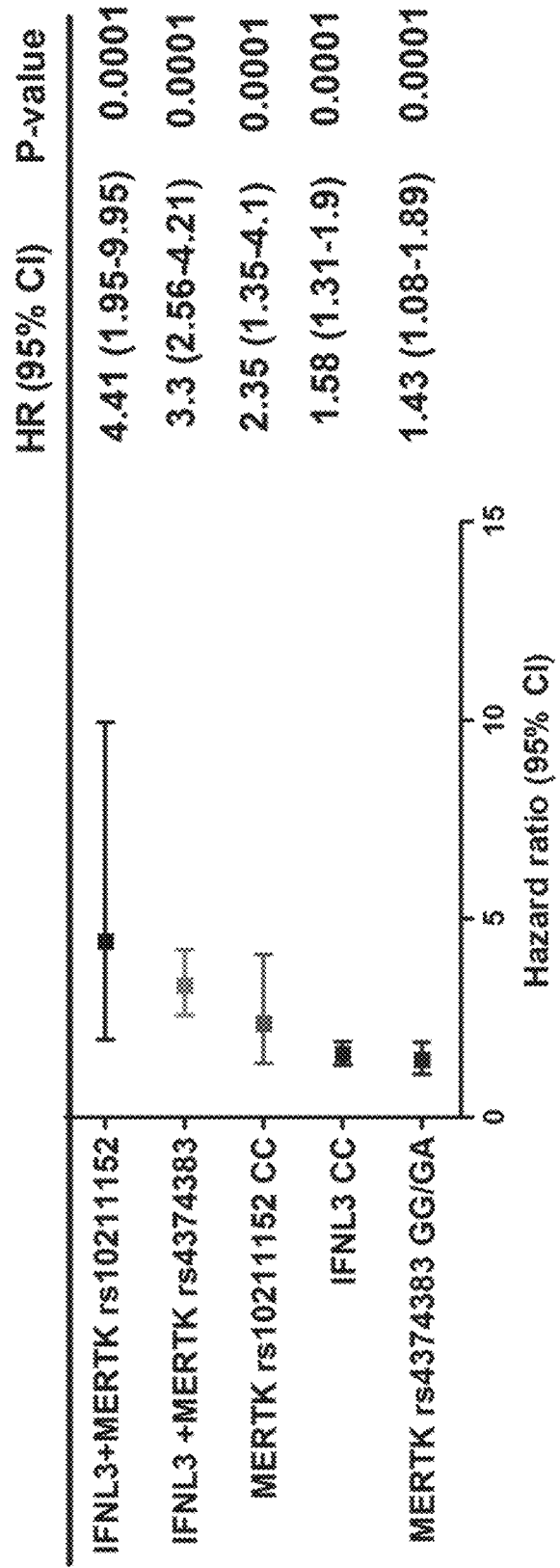
FIG. 6 is a graphical representation showing the non-additive interaction between the IL28B genotype rs12979860-CC ("IFNL3 CC" or "IFNL3" in the figure) and either (i) the MERTK genotype rs4374383-AG/GG ("MERTK rs4374383 GG/GA" or "MERTK rs4374383" in the figure) or (ii) the MERTK genotype rs10211152-CC (MERTK rs10211152 CC" or "MERTK rs10211152" in the figure), in development of significant liver fibrosis i.e., Metavir Stage F2-F4, in HCV-infected subjects. After checking the normality of the quantified variables, appropriate logarithmic transformations were made, and a Cox proportional-hazards regression model was fitted, and the covariates were considered significant if P<0.05. The proportional hazard assumption was checked and a final model was proposed, considering only the significant terms. Univariate and multivariate Cox-regression was used to explore the possible predictors of significant fibrosis. The likelihoods, as determined by Hazard Ratio (HR) at the 95% confidence interval (95% CI), that subjects carrying one of each genotype or both genotypes are at higher cumulative probability of rapid progression to late-stage liver fibrosis, are shown in the figure. Statistical significance of the data (p<0.0001) is also shown.

FIG. 5 also shows a non-additive interaction between the IL28B genotype rs12979860-CC and either (i) the MERTK genotype rs4374383-AG/GG or (ii) the MERTK genotype rs10211152-CC. The data indicate that there is a strong correlation, which is more than merely additive, between the combined rs12979860-CC and rs4374383-AG/GG genotype, and between the combined rs12979860-CC and rs10211152-CC genotype, and late-stage liver fibrosis in subjects having chronic HCV infection. Data indicate further that rs10211152 may be a causative allele in progression to late-stage fibrosis given the strength of the association involving the rs10211152-CC genotype. Similar conclusions are drawn from the data provided in FIG. 6. The data indicate further that rs10211152 may be a causative allele in progression to significant fibrosis, given the strength of the association involving the rs10211152-CC genotype.

Non-Additive Interaction Between IL28B and MERTK and RNF7 Genotypes in Progression of Fibrosis Patients in one or more cohorts described herein are graded with respect to the extent of fibrosis in the relevant organ i.e., liver, kidney or lung, and the extent of fibrosis and rate of progression of fibrosis from the time of diagnosis are scored. Patient SNP genotypes linked to IL28B and MERTK and several other fibrosis genes including TULP1, RNF7 and PNPLA3 were determined and correlated to extent of fibrosis and fibrosis progression rate for patients in the one or more cohorts.

By way of a non-limiting example, data are provided herein for progression of liver fibrosis based on data obtained from the CHC cohort.

In one example, odds ratios were obtained showing the association of each of MERTK rs4374383, IL28B rs12979860, TULP1 rs9380516, RNF7 rs16851720 and PNPLA3 rs738409 with significant fibrosis in a cohort of 1000 HCV-infected patients. Data provided in Table 3 indicate single genotype associations between each of MERTK rs4374383 and IL28B rs12979860 and significant fibrosis, as expected. The effects of combining either the MERTK rs4374383 or the IL28B rs12979860 genotype with genotypes linked to TULP1 or RNF7 or PNPLA3 was also tested. Data provided in Table 3 indicate that, of the SNP genotypes linked to the additional fibrosis genes that were tested, only RNF7 rs16851720 provides a significant association with fibrosis progression when combined with MERTK rs4374383 or IL28B rs12979860. In contrast, TULP1 decreased the predictive value of MERTK when rs9380516 and rs4374383 were combined, and no improvement was observed, relative to the predictive value of IL28B alone, when rs9380516 and rs12979860 were combined. Similarly, only marginal improvements in predictive capacity that were not highly significant were observed from combinations involving PNPLA3 rs738409 with either MERTK rs4374383 or IL28B rs12979860.

TABLE 3

| SNP | OR for SNP (95% CI) | SNP P value | SNP plus rs4374383 | P value (combination) | SNP plus rs12979860 | P value (combination) |
|---|---|---|---|---|---|---|
| TULP1 rs9380516 | 1.35 | 0.03 | 1.64 | 0.09 | 1.94 | 0.01 |
| RNF7 rs16851720 | 1.31 | 0.03 | 2.15 | 0.01 | 3.33 | <0.0001 |
| PNPLA3 rs738409 | 1.94 | 0.02 | 2.26 | 0.01 | 2.68 | 0.01 |
| MERTK rs4374383 | 1.89 | <0.0001 | | | 4.61 | <0.0001 |
| IL28B rs12979860 | 2.17 | <0.0001 | 4.61 | <0.0001 | | |

Data showing the contributions of different genotypes for the combinations MERTK rs4374383 and IL28B rs12979860 with RNF7 rs16851720, TULP1 rs9380516 and PNPLA3 rs738409 are provided in Table 4.

TABLE 4

| Variables | Fibrosis Stage <2 | Fibrosis stage ≥2 | Univariate Analysis P value | Multivariate Analysis OR (95% CI) | P value |
|---|---|---|---|---|---|
| IL28B + MERTK + RNF7 | | | | | |
| CC + GG/GA + AA (%) | 62(29) | 150(71) | <0.0001 | 8.16 (3.51-18.96) | <0.0001 |
| CT/TT + AA + CA/CC (%) | 27(77) | 8(23) | | | |
| IL28B + MERTK + TULP1 | | | | | |
| CC + GG/GA + CC | 79(35.3) | 145(64.7) | | | |
| CT/TT + AA + CT/TT | 23(71.9) | 9(28.1) | <0.0001 | 4.69 (2.07-10.67) | <0.0001 |
| IL28B + MERTK + PNPLA3 | | | | | |
| CC + GA/AA + GG | 5(29.4) | 12(70.6) | 0.005 | 5.02 (1.63-15.47) | 0.005 |
| CT/TT + AA + CC/CG | 67(67.7) | 32(32.3) | | | |

The data provided in Table 4 indicate that the combined MERTK rs4374383-GG/GA, IL28B rs12979860-CC and TULP1 rs9380516-CC genotype, and the combined MERTK rs4374383-GG/GA, IL28B rs12979860-CC and PNPLA3 rs738409-GG genotype, provide strong associations with fibrosis progression in HCV-infected subjects. However, the predictive value of those genotype combinations is only marginally improved compared to the effect of the combined MERTK rs4374383-GG/GA and IL28B rs12979860-CC genotype alone (OR 4.61; p<0.0001), and much lower than the effect of the combined MERTK rs10211152-CC and IL28B rs12979860-CC genotype alone (OR 7.4; p<0.0001). Consistent with the data provided in Table 3, the data in Table 4 suggest that there is no interaction between the combined MERTK rs4374383 and IL28B rs12979860 genotype and either the TULP1 rs9380516-CC genotype or the PNPLA3 rs738409-GG genotype in predicting progression of fibrosis.

On the other hand, the data provided in Table 4 also indicate a strong interaction between MERTK rs4374383, IL28B rs12979860, and RNF7 rs16851720 in predicting progression of fibrosis, and demonstrate that the RNF7 rs16851720-AA genotype significantly enhances the predictive value of the combined MERTK rs4374383 and IL28B rs12979860 genotype (OR 8.16 cf 4.61; p<0.0001).

In another example, the inventors assessed whether or not there was any epistasis between RNF7 and the other fibrosis genes, PNPLA3 and TULP1. Odds ratios were obtained showing the association of each of TULP1 rs9380516, RNF7 rs16851720 and PNPLA3 rs738409, alone and in combination, with significant fibrosis in a cohort of 1000 HCV-infected patients. Data provided in Table 5 indicate that it is unlikely that any positive interaction occurs between these SNP genotypes in fibrosis progression. Accordingly, IL28B, MERTK and RNF7 appears to operate through a different mechanism than TULP1 or PNPLA3, or alternatively, the genotypes identified by the present inventors linked to IL28B and/or MERTK and/or RNF7 are more likely to be causative genotypes in liver fibrosis susceptibility and/or severity and/or progression.

TABLE 5

| SNP | OR for SNP (95% CI) | P value | SNP plus TULP1 | P value | SNP plus RNF7 | P value | SNP plus PNPLA3 | P value |
|---|---|---|---|---|---|---|---|---|
| TULP1 rs9380516 | 1.35 | 0.03 | | | 0.9 | 0.6 | 1.13 | 0.6 |
| RNF7 rs16851720 | 1.31 | 0.03 | 0.9 | 0.6 | | | 1.96 | 0.06 |
| PNPLA3 rs738409 | 1.94 | 0.02 | 1.13 | 0.6 | 1.96 | 0.06 | | |

Data provided in Table 6 demonstrate interactions between other IL28B, MERTK and RNF7 SNPs of the invention not described by way of Tables 1-5 or FIGS. 1-7 hereof, in predicting fibrosis susceptibility and/or severity and/or progression. In particular, data indicate that the combination of IL28B rs12979860-CC and MERTK rs10211152-CC and RNF7 rs16851720-AA is much more highly predictive of fibrosis susceptibility and/or severity and/or progression than other linked genotypes having a strong association with fibrosis susceptibility and/or severity and/or progression.

These data provide further support for a mechanistic link between apoptosis and fibrogenesis and/or progression of fibrosis.

TABLE 6

| Variables | Prevalence in Caucasians | | Multivariate Analysis | |
|---|---|---|---|---|
| | Bad combination | Good combination | OR (95% CI) | P value |
| rs10211152 + rs12979860 + rs16851720 | | | | |
| CC + CC + AA (%) | 26.4% | 1.3% | 10.42 (4.22-57.84) | 0.001 |
| CT/TT + CT/TT + AC/CC (%) | | | | |
| rs10211152 + rs8099917 | | | | |
| CC + TT | 52% | 1.9% | 4.26 (1.44-7.46) | <0.0001 |
| CT/TT + TG/GG | | | | |
| rs4374383 + rs8099917 | | | | |
| GG/GA + TT | 51.4% | 9.3% | 3 (1.89-4.75) | <0.0001 |
| AA + TG/GG | | | | |
| rs16851720 + rs8099917 | | | | |
| AA + TT | 37.2% | 14.1% | 2.29 (1.54-3.41) | <0.0001 |
| AC/CC + TG/GG | | | | |
| rs4374383 + rs8099917 + rs16851720 | | | | |
| GG/GA + TT + AA | 29.3% | 2.4% | 5.42 (1.41-8.97) | <0.0001 |
| AA + TG/GG + CA/CC | | | | |
| rs10211152 + rs8099917 + rs16851720 | | | | |
| CC + TT + AA | 35.3% | 1.1% | 5.86 (1.51-22.23) | 0.001 |
| CT/TT + TG/GG + AC/CC | | | | |

Overall, the data provided herein suggest the following risks of faster fibrosis progression dependent on patient combined genotypes compared to those subjects having a favorable combined genotype at the same loci, other factors being equal i.e., considering the effect of genotype alone:

a) IL28B rs12979860+MERTK rs4374383: There is a 76% likelihood of faster progression;
b) IL28B rs12979860+MERTK rs10211152: There is a 81.5% likelihood of faster progression;
c) IL28B rs12979860+MERTK rs4374383+RNF7 rs16851720: There is a 79% likelihood of faster progression; and
d) IL28B rs12979860+MERTK rs10211152+RNF7 rs16851720: There is a 83.5% likelihood of faster progression.

Assay Stratification According to Prevalence of Genotypes

Data provided in Table 7 shows the IL28B, MERTK and RNF7 SNP fast progression genotype frequencies in healthy controls from Asia, Europe and Africa, and Table 8 shows the SNP allele and genotype frequencies for these genetic groups, as a basis for assays stratification according to genetic diversity of test populations as described herein. Table 9 expands on data summarized above wherein the data processor comprises computer-executable mathematical algorithms (1)-(3) for calculating a fibrosis probability score (FPS) that is correlated with a fibrosis stage or a likelihood that a subject will develop fibrosis and/or progress to a particular stage of fibrosis and/or progress rapidly to a late-stage fibrosis and shows the prevalence of the specific combined genotypes in European chronic hepatitis C populations and the positive likelihood that a person having each combined genotype will progress rapidly to severe or late-stage fibrosis.

TABLE 7

| Gene | SNPs | European | Asian | African |
|---|---|---|---|---|
| IFNL3 | rs12979860CC | | | |
| MERTK | rs4374383G* | 39% | 35% | 11% |
| IFNL3 | rs12979860CC | | | |
| MERTK | rs4374383G* | | | |
| RFN7 | rs16851720AA | 25% | 29% | 6% |
| IFNL3 | rs12979860CC | | | |
| MERTK | rs10211152CC | 43% | 85% | 13% |
| IFNL3 | rs12979860CC | | | |
| MERTK | rs10211152CC | | | |
| RFN7 | rs16851720AA | 28% | 73% | 7% |
| IFNL3 | rs8099917TT | | | |
| MERTK | rs4374383G* | 57% | 35% | 62% |

TABLE 7-continued

| Gene | SNPs | European | Asian | African |
|---|---|---|---|---|
| IFNL3 | rs8099917TT | | | |
| MERTK | rs4374383G* | | | |
| RFN7 | rs16851720AA | 36% | 30% | 32% |
| IFNL3 | rs8099917TT | | | |
| MERTK | rs10211152CC | 63% | 87% | 75% |
| IFNL3 | rs8099917TT | | | |
| MERTK | rs10211152CC | | | |
| RFN7 | rs16851720AA | 40% | 74% | 39% |

TABLE 8

| SNP | Ethnicity | Allele 1 | Allele 2 | Genotype | | |
|---|---|---|---|---|---|---|
| | | T | C | TT | TC | CC |
| rs12979860 | EUR | 32.00% | 68.00% | 10.60% | 42.50% | 47.00% |
| | ASN | 7.50% | 92.50% | 0.56% | 15.00% | 85.00% |
| | AFR | 60.00% | 40.00% | 36.20% | 48.40% | 15.40% |
| | | G | T | GG | GT | TT |
| rs8099917 | EUR | 17.00% | 83.00% | 2.40% | 29.30% | 68.30% |
| | ASN | 6.60% | 93.40% | 0.44% | 13.30% | 86.70% |
| | AFR | 5.90% | 94.10% | 0.35% | 11.80% | 88.20% |
| | | A | G | AA | AG | GG |
| rs4374383 | EUR | 38.30% | 61.70% | 16.40% | 43.80% | 39.80% |
| | ASN | 76.90% | 23.10% | 59.40% | 35.00% | 5.60% |
| | AFR | 52.00% | 48.00% | 29.30% | 45.50% | 25.20% |
| | | T | C | TT | TC | CC |
| rs10211152 | EUR | 4.00% | 96.00% | 0.30% | 7.40% | 92.30% |
| | ASN | 0.00% | 100.00% | 0.00% | 0.00% | 100.00% |
| | AFR | 8.50% | 91.50% | 1.60% | 13.80% | 84.60% |
| | | C | A | CC | AC | AA |
| rs16851720 | EUR | 0.198 | 0.802 | 0.034 | 0.327 | 0.639 |
| | ASN | 0.073 | 0.927 | 0.005329 | 0.147 | 0.853 |
| | AFR | 0.299 | 0.701 | 0.114 | 0.37 | 0.516 |

TABLE 9

| Combination | Prevalence | Likelihood of significant fibrosis (F2-F4) |
|---|---|---|
| IL28B rs12979860 + MERTK rs4374383 | | |
| CC + GG/GA (bad combination) | 34.5% | 68.7% |
| CT/TT + AA (good combination) | 12.1% | 32.2% |
| IL28B rs12979860 + MERTK rs10211152 | | |
| CC + CC (bad combination) | 39.4% | 65.7% |
| CT/TT + CT/TT (Good combination) | 3.4% | 20.6% |
| IL28B rs12979860 + MERTK rs4374383 + RNF7 rs16851720 | | |
| CC + GG/GA + AA (bad combination) | 21.2% | 70.8% |
| CT/TT + AA + CA/CC (good combination) | 3.6% | 22.9% |
| IL28B rs12979860 + MERTK rs10211152 + RNF7 rs16851720 | | |
| CC + CC + AA (bad combination) | 26.4% | 68.9% |
| CT/TT + CT/TT + CA/CC (Good combination) | 1.3% | 15.4% |

Algorithms for Performing the Assays of the Invention

Based on assays of the different combined genotypes set forth in Table 9, the inventors developed four specific algorithms in addition to those presented herein above, to evaluate the likelihood that a patient will progress rapidly to severe fibrosis including late-stage fibrosis. The algorithms shown in these examples combine specific genotype effects with age, GGT, AST, and bilirubin levels in serum, and with platelet count.

Model 1: Assay rs10211152+rs12979860+rs1681720 (ROC=0.815)

The probability of progressing to severe fibrosis is determined by a Fibrosis Probability Score (FPS)=1−[1/(1+exp(Z))], wherein:

$$Z=-4.5643+(0.5209*rs12979860)+(0.3572*rs10211152)+(0.1357*rs16851720)+(0.0373*Age)$$

wherein:
if rs12979860-CC the value is 1, or if rs12979860-CT the value is −1.0, or if rs12979860-TT the value is −1.0;
if rs16851720-AA the value is 1, or if rs16851720-AC the value is −1.0, or if rs16851720-CC the value is −1.0; and
if rs10211152-CC the value is 1, or if rs10211152-CT the value is −1.0, or if rs10211152-TT the value is −1.0.

Figure 7:
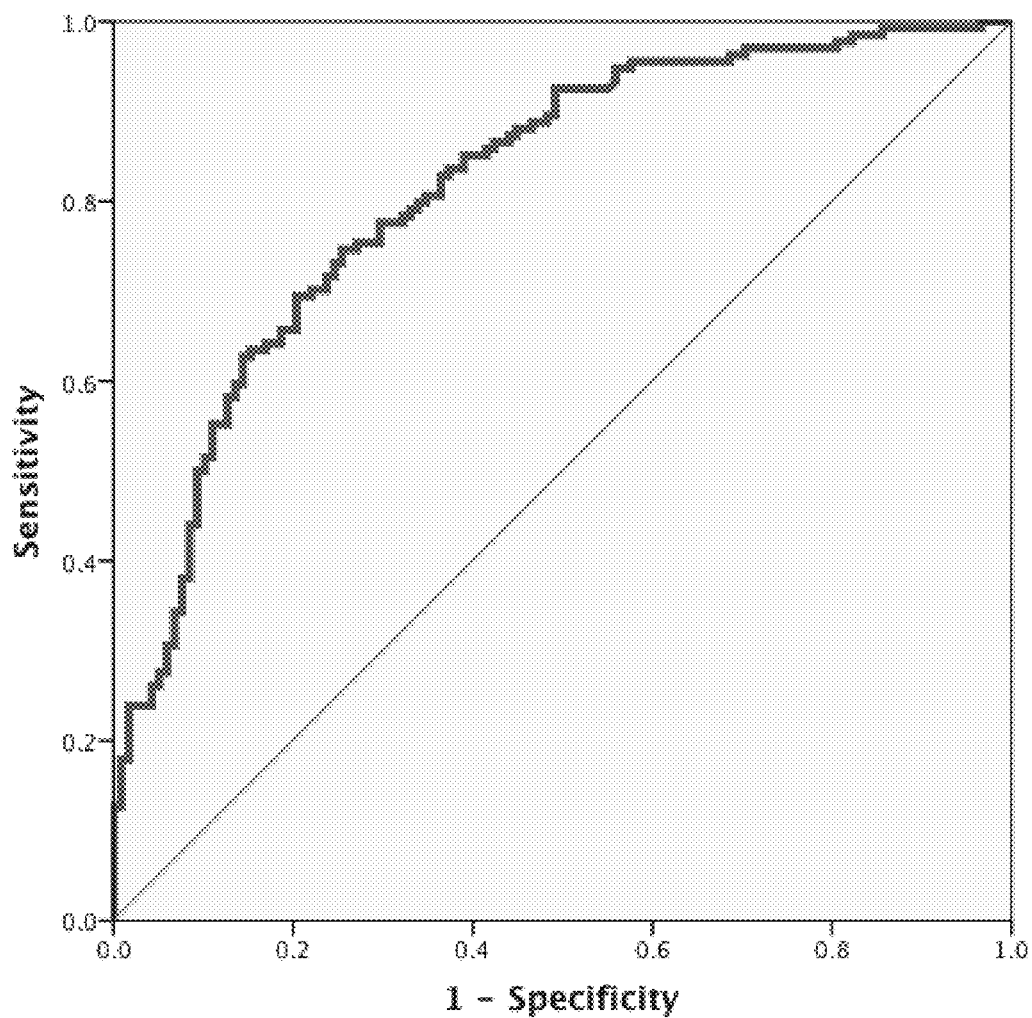
FIG. 7 is a graphical representation showing an exemplary ROC curve for a genotyping assay of the present invention, employing the combined rs10211152-CC and rs12979860-CC and rs16851720-AA genotype. Fibrosis Probability Scores were calculated for a population of subjects infected with HCV according to the algorithms (7)-(9) wherein Z was calculated according to formula (20) hereof.

By way of example, data provided in FIG. 7 show the FPS calculated for a population of subjects infected with HCV according to the above algorithm. The data indicate an area under the curve (AUC) of 0.815 (95% CI: 0.76-0.867, P=0.0001) for the genotype combination. Sensitivity, specificity, and positive likelihood ratio are derivable from the data provided. Similar data were obtained for other gene combinations employing one or more of the algorithms set forth in formulae (1)-(22) hereof as described.

For example, for the fastest-progression (worst case) genotype, aged 70:

$$Z=0.94$$

$$FPS=1-[1/(1+e^Z)]=1-[1/(1+2.55998)]=1-0.28=0.72.$$

In another example, for the slowest progression (best case) genotype, aged 70:

$$Z=-1.07$$

$$FPS=1-[1/(1+e^Z)]=1-[1/(1+0.343)]=1-0.75=0.25.$$

In another example, for the fastest-progression (worst case) genotype, aged 20:

$$Z=-0.9275$$

$$FPS=1-[1/(1+e^Z)]=1-[1/(1+0.395)]=1-0.717=0.283.$$

In another example, for the slowest-progression (best case) genotype, aged 20:

$$Z=-2.94$$

$$FPS=1-[1/(1+e^Z)]=1-[1/(1+0.0529)]=1-0.95=0.05.$$

Model 2: Assay rs10211152+rs12979860 (ROC=0.7916)

Fibrosis Probability Score=$1-[1/(1+\exp(Z))]$, wherein:

$$Z=-4.5508+(0.5238*rs12979860)+\\(0.3488*rs10211152)+(0.0374*Age)+\\(0.00427*AST)+(0.00263*GGT)+(0.0249*Bilirubin)-(0.00526*platelets)$$

wherein:
if rs12979860-CC the value is 1, or if rs12979860-CT the value is −1.0, or if rs12979860-TT the value is −1.0; and
if rs10211152-CC the value is 1, or if rs10211152-CT the value is −1.0, or if rs10211152-TT the value is −1.0.

Model 3: Assay of rs12979860+rs4374383+rs16851720 (ROC=0.804)

Fibrosis Probability Score=$1-[1/(1+\exp(Z))]$, wherein:

$$Z=-4.3072+(0.5195*rs12979860)+(0.2115*\\(rs4374383*rs16851720))+(0.0368*Age)+\\(0.00452*AST)+(0.00279*GGT)+(0.0255*Bilirubin)-(0.00538*platelets)$$

wherein:
if rs12979860-CC the value is 1, or if rs12979860-CT the value is −1.0, or if rs12979860-TT the value is −1.0;
if rs4374383-GG the value is 1, or if rs4374383-GA the value is 1, or if rs4374383-AA the value is −1.0; and
if rs16851720-AA the value is 1, or if rs16851720-AC the value is −1.0, or if rs16851720-CC the value is −1.0.

Model 4: Assay of rs12979860+rs4374383 (ROC=0.7847)

Fibrosis Probability Score=$1-[1/(1+\exp(Z))]$, wherein:

$$Z=-4.4513+(0.5199*rs12979860)+\\(0.2857*rs4374383)+(0.0362*Age)+\\(0.0046*AST)+(0.00269*GGT)+(0.0246*Bilirubin)-(0.00528*platelets)$$

wherein:
if rs12979860-CC the value is 1, or if rs12979860-CT the value is −1.0, or if rs12979860-TT the value is −1.0; and
if rs4374383-GG the value is 1, or if rs4374383-GA the value is 1, or if rs4374383-AA the value is −1.0.

Example 2

Having determined that the combination of IL28B SNP rs12979860 and MERTK SNP rs10211152 provides a strong correlation with fibrosis progression in the HCV CHC cohort, and that rs10211152 is most likely to be a causative SNP associated with liver fibrosis progression and/or liver fibrosis progression rate, the inventors sought to confirm these data in a replication cohort of chronically HCV-infected subjects.

Patient Cohorts

A cohort of 957 Caucasian subjects having chronic HCV infection, all of whom had a liver biopsy that produced a Metavir fibrosis stage, and disease activity before treatment, was used on this study. Patients were excluded if they had evidence of other liver diseases by standard tests.

Liver Histopathology and Genotyping

Liver histopathology and genotyping of cohort samples for IL28B rs12979860 and MERTK rs10211152 was performed in accordance with Example 1.

Determination of Fibrosis Progression Rate

The fibrosis progression rate (FPR) was determined by calculating the ratio between the fibrosis stage and the estimated disease duration (in years). Two approaches were used to assess fibrosis progression.

First, patients were stratified into two groups of stage-constant FPRs according to the median rate (i.e., 0.076 fibrosis units/year), which was used as a cutoff. Factors associated with rapid FPR (i.e., higher than a median progression rate) were analyzed by univariate and multivariate regression analysis.

Second, Cox regression analysis was employed to model the time taken for significant fibrosis (Metavir Stage F2 or F3 or F4) to occur. After checking the normality of the quantified variables, appropriate logarithmic transformations were made. A Cox proportional-hazards regression model was fitted, and the covariates were considered significant if P<0.05. The proportional hazard assumption was checked and a final model was proposed, considering only the significant terms. Univariate and multivariate Cox-regression was used to explore the possible predictors of significant fibrosis.

Non-Additive Interaction Between IL28B and MERTK Genotypes in Rapid Progression of Fibrosis Patients were graded with respect to the extent of fibrosis in the liver, and the extent of fibrosis and rate of progression of fibrosis from the time of diagnosis. Patient SNP genotypes linked to IL28B and MERTK were determined and correlated to extent of fibrosis and fibrosis progression rate for each of the patients.

Data from the replication cohort confirmed the existence of an interaction between specific IL28B and MERTK SNP genotypes and demonstrates that the combination of IL28B SNP rs12979860 and MERTK SNP rs10211152 provides a strong correlation with fibrosis progression.

The inventors stratified subjects in the replication HCV cohort that developed significant fibrosis i.e., Metavir Stage F2/F3/F4 according to their combined genotypes at rs12979860 and rs10211152. Data (not shown here) support the association of rs12979860-CC and rs10211152-CC genotypes with late-stage liver fibrosis and with progression of liver fibrosis e.g., in HCV-infected subjects. The likelihoods, as determined by Odds Ratio (OR) at the 95% confidence interval (95% CI), that subjects carrying the IL28B genotype rs12979860-CC and/or the MERTK genotype rs10211152-CC will progress to late-stage liver fibrosis was found to be 6.42 (95% CI=3.78-10.9, p=$2.18\times10^{-4}$). A similar effect was observed with increased hazard of progression to significant fibrosis with HR: 3.17 (95% CI: 1.78-5.66, p=$9.1\times10^{-4}$). Thus, a strong correlation, consistent with a non-additive interaction, between the combined rs12979860-CC and rs10211152-CC genotype and late-stage liver fibrosis was observed in subjects from the replication cohort having chronic HCV infection. These findings are consistent with the findings in Example 1 that a non-additive interaction exists between rs12979860-CC and rs10211152-CC genotypes which is associated with progression to significant liver fibrosis, including late-stage liver fibrosis, in subjects having chronic HCV infection.

To confirm that there is a non-additive interaction between the IL28B rs12979860 and MERTK rs10211152, the inventors also utilized a logistic likelihood ratio test comparing the full model, including multiplicative interaction term, with the reduced model, without the interaction term, in the replication cohort. In doing so, the inventors have shown that a clear interaction exists between rs12979860 and rs10211152 (p-value for interaction=2.02× $10^{-10}$). This association reached formal significance after adjustment for multiple testing ($p_{corrected}$ for 21 combinations of 7 SNPs=0.002).

Example 3

Based on the finding in Examples 1 and 2 that the combination of IL28B SNP rs12979860 and MERTK SNP rs10211152 provides a strong correlation with fibrosis progression in subjects having chronic HCV infection, the inventors sought to determine whether this combination of markers could have similar utility in predicting the development of liver fibrosis, including progression to significant fibrosis or late-stage liver fibrosis, in subjects suffering from non-alcoholic fatty liver disease (NAFLD).

In this regard, fibrosis is regarded as the best predictor of adverse clinical outcomes in FAFLD, which is the most growing and common cause of liver disease in western countries.

Patient Cohorts

A cohort of 502 consecutive European Caucasian patients with histologically proven NAFLD, and fulfilling all inclusion and exclusion criteria detailed below, was assessed.

Inclusion criteria were: (1) availability of blood samples for genetic analyses; and (2) histological diagnosis of NAFLD on a liver biopsy done less than 6 months before enrollment. The diagnosis of NAFLD was based on chronically elevated ALT for at least 6 months, alcohol consumption <20 g/day in the year before liver biopsy and evaluated by a questionnaire, and steatosis (>5% of hepatocytes) at histology with or without necroinflammation, and/or fibrosis.

Exclusion criteria were: (1) hepatocellular carcinoma; (2) other causes of liver disease or mixed etiologies (excessive alcohol consumption, hepatitis C, hepatitis B, autoimmune liver disease, Wilson's disease, hemochromatosis, α1-antitrypsin deficiency); (3) human immunodeficiency virus infection; (4) previous treatment with antiviral therapy, immunosuppressive drugs, and/or regular use of steatosis-inducing drugs, evaluated by interview; (5) therapy with medications known to affect uric acid (UA) metabolism; and (7) active intravenous drug addiction.

Liver Histopathology and Genotyping

Biopsies were interpreted by a single expert liver pathologist in each center who was blinded to patient clinical characteristics, serum measurements and IL28B genotyping. All biopsies had a minimum length of 15 mm or the presence of at least 11 complete portal tracts; inadequate biopsies were excluded as described by Colloredo et al., *J Hepatol.* 39, 239-244, 2003.

Necroinflammation (A) was graded as A0 (absent), A1 (mild), A2 (moderate), or A3 (severe).

The Kleiner classification was used to compute the non-alcoholic fatty liver disease activity (NAS) score (from 0 to 8, on a scale including separate scores for steatosis, lobular inflammation, and hepatocellular ballooning), and to stage fibrosis from 0 to 4 (Kleiner et al., *Hepatology* 41, 1313-1321, 2005).

Determination of Fibrosis Progression Rate

The fibrosis progression rate (FPR) was determined by calculating the ratio between the fibrosis stage and the estimated disease duration (in years).

Non-Additive Interaction Between IL28B and MERTK Genotypes in Rapid Progression of Fibrosis Patients were graded with respect to the extent of fibrosis in the liver, and the extent of fibrosis and rate of progression of fibrosis from the time of diagnosis. Patient SNP genotypes linked to IL28B and MERTK were determined and correlated to extent of fibrosis and fibrosis progression rate for each of the patients.

Figure 8:
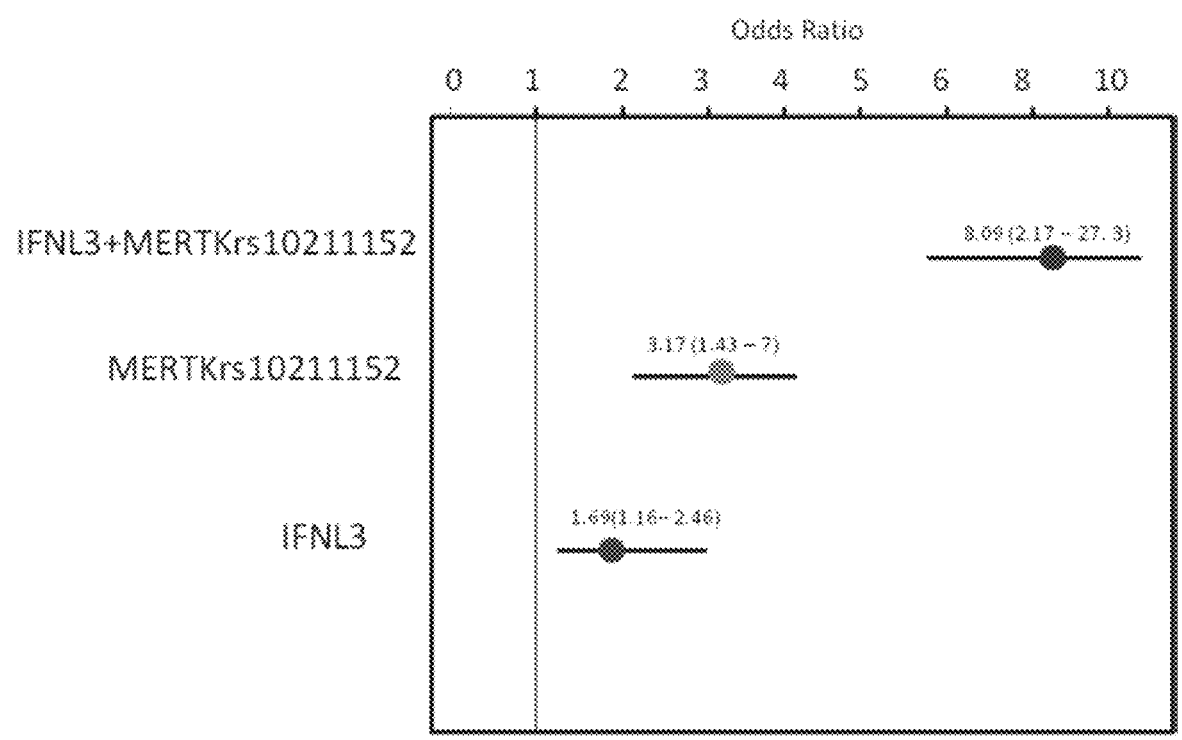
FIG. 8 is a graphical representation showing the non-additive interaction between the IL28B genotype rs12979860-CC ("IFNL3 CC" or "IFNL3" in the figure) and the MERTK genotype rs10211152-CC (MERTK rs10211152 CC" or "MERTK rs10211152" in the figure), in development of significant liver fibrosis in NAFLD subjects (n=502).

The inventors stratified subjects in the NAFLD cohort that developed significant fibrosis according to their combined genotypes at rs12979860 and rs10211152. The data support the association of rs12979860-CC and rs10211152-CC genotypes with fibrosis stage and with progression of liver fibrosis e.g., in NAFLD subjects (FIG. 8). The likelihoods, as determined by Odds Ratio (OR) at the 95% confidence interval (95% CI), that a NAFLD subject carrying the IL28B genotype rs12979860-CC and/or the MERTK genotype rs10211152-CC will develop significant fibrosis was found to be 8.09 (95% CI=2.17-27.3, p=0.001). There was also evidence of an interaction between at rs12979860 and rs10211152 (p-value for interaction=1×$10^{-5}$). This interaction was also apparent from the data presented in FIG. 7, which clear illustrates that the combined effect of rs12979860 and rs10211152 is more than additive in predicting the likelihood of development of liver fibrosis, including progression to significant fibrosis or late-stage liver fibrosis, in subjects suffering from NAFLD.

We claim:

1. A method of determining a likelihood that a subject having a medical condition associated with onset or progression of fibrosis is predisposed to developing fibrosis or is predisposed to progressing to a particular stage of fibrosis or is predisposed to a rapid progression of fibrosis, the method comprising:
    (i) performing one or more genotyping assays on a DNA-containing sample obtained from the subject, wherein the one or more genotyping assays comprise contacting one or more nucleic acids configured to independently discriminate single nuclear polymorphism (SNP) genotypes in or at least linked to both the human IL28B gene and the human MERTK gene with the DNA-containing sample, wherein the SNP in or at least linked to human IL28B gene is rs12979860 and the SNP in or at least linked to human MERTK gene is rs4374383, wherein the assay results indicate a likelihood that the subject will develop fibrosis and/or progress to a particular stage of fibrosis and/or progress rapidly to a late-stage fibrosis; and
    (ii) treating the fibrosis and/or the medical condition in a subject having a strong likelihood of developing fibrosis or progressing to a particular stage of fibrosis or progressing rapidly to a late-stage fibrosis based on the assay results at (i).

2. A method of determining a likelihood that a subject having a medical condition associated with onset or progression of fibrosis will develop fibrosis and/or progress to a particular stage of fibrosis and/or progress rapidly to a late-stage fibrosis, said method comprising:
    (a) performing one or more genotyping assays on a DNA-containing sample obtained from the subject, wherein the one or more genotyping assays comprise contacting one or more nucleic acids configured to independently discriminate between different genotypes in or at least linked to both the human IL28B gene and the human MERTK gene with the DNA-containing sample, wherein the genotypes in or at least linked to the human IL28B gene are alleles of a single nuclear polymorphism (SNP) that is rs12979860, and wherein the genotypes in or at least linked to the human MERTK gene are alleles of a SNP that is rs4374383; and (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:

(i) a CC genotype in rs12979860; and
(ii) an AG genotype or GG genotype in rs4374383,
thereby determining a likelihood that the subject will develop fibrosis and/or progress to a particular stage of fibrosis and/or progress rapidly to a late-stage fibrosis; and (c) treating the fibrosis and/or the medical condition in a subject determined at (a) and (b) as having a strong likelihood of developing fibrosis or progressing to a particular stage of fibrosis or progressing rapidly to a late-stage fibrosis.

3. The method according to claim 1, wherein the method comprises:
(a) performing the one or more genotyping assays, wherein the genotypes in the human IL28B gene are in the SNP rs12979860, and wherein the genotypes in the human MERTK gene are in the SNP rs4374383; and
(b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
(i) a CC genotype in rs12979860; and
(ii) an AG genotype or GG genotype in rs4374383.

4. The method according to claim 1, wherein performing one or more genotyping assays on the DNA-containing sample comprises performing the genotyping assays under conditions that discriminate between the following combinations of genotypes in the sample DNA:
(a) between homozygotes (CC), heterozygotes (CT) and alternate homozygotes (TT) at rs12979860; and
(b) between homozygotes (GG), heterozygotes (AG) and alternate homozygotes (AA) at rs4374383.

5. The method according to claim 1, further comprising performing a genotype assay for a SNP selected from the group consisting of rs17175626 and rs6748256.

6. The method according to claim 1, further comprising performing one or more additional genotyping assays on the DNA-containing sample obtained from the subject, wherein the one or more additional genotyping assays are configured to discriminate single nuclear polymorphism (SNP) genotypes in or at least linked to the human RNF7 gene, wherein the SNPs are selected from rs16851720 and a SNP in linkage disequilibrium with rs16851720.

7. The method according to claim 6, wherein the method comprises performing one or more additional genotyping assays on the DNA-containing sample obtained from the subject, wherein the one or more additional genotyping assays are configured to discriminate between alleles at the SNP rs16851720, and wherein detection of an AA genotype in rs16851720 in combination with the SNPs in both the IL28B and MERTK genes indicates a strong likelihood that the subject will develop fibrosis and/or progress rapidly to a late-stage fibrosis.

8. The method according to claim 1, wherein the assays comprise PCR assays and/or real-time PCR assays and/or minisequencing assays and/or next generation sequencing assays and/or isothermal nucleic acid sequence-based amplification assays (NASBA) and/or oligonucleotide ligation-PCR assays.

9. The method according to claim 1, wherein the assays comprise multiplex assays for simultaneous discrimination between the SNPs in both the IL28B and MERTK genes.

10. The method according to claim 1, wherein the combined SNP genotypes in the human IL28B gene and the human MERTK gene provide a stronger likelihood that a subject is predisposed to a rapid progression of fibrosis than a likelihood obtained by adding the separate effect of each of said genotypes.

11. The method according to claim 1, further comprising the first step of providing a kit comprising nucleic acids that discriminate between different genotypes in the human IL28B and the human MERTK gene and the human RNF7 gene of the sample DNA, and then performing the one or more genotyping assays employing those nucleic acids.

12. The method according to claim 1, wherein the fibrosis is liver fibrosis.

13. The method according to claim 1, wherein the subject has a medical condition associated with progression of fibrosis selected from the group consisting of: a disease with secondary involvement of the liver, hemochromatosis, a congenital hepatic fibrosis, chronic hepatitis B, chronic hepatitis C, non-alcoholic steatohepatitis (NASH), primary biliary cirrhosis, primary sclerosing cholangitis, reduced hepatic blood flow, hepatic veno-occlusive disease, hepatocellular carcinoma, and scarring due to prior liver surgery.

14. A kit for performing the method according to claim 1, said kit comprising two or more nucleic acids that independently discriminate between different single nuclear polymorphism (SNP) genotypes in or at least linked to the human IL28B gene and the human MERTK gene, wherein the SNP in or at least linked to the human IL28B is rs12979860 and the SNP in or at least linked to the human MERTK is rs4374383.

15. The kit according to claim 14 further comprising:
(i) one or more nucleic acids that independently discriminate between one or more further SNP genotypes in or at least linked to human IL28B, wherein the SNPs are selected from rs8099917 and a SNP in linkage disequilibrium with rs8099917;
(ii) one or more nucleic acids that discriminate between one or more further SNP genotypes in or at least linked to human MERTK, wherein the SNPs are selected from rs10211152 and a SNP in linkage disequilibrium with rs10211152; and/or
(iii) one or more nucleic acids that discriminate between SNP genotypes in the human RNF7 gene, wherein the SNPs are selected from rs16851720 and a SNP in linkage disequilibrium with rs16851720.

16. The kit according to claim 14, wherein the nucleic acids are for use in multiplex assays for simultaneous discrimination between SNP genotypes in each of the genes.

17. The method of claim 1, wherein the DNA-containing sample is obtained from a subject having no visible fibrosis or early signs of fibrosis to thereby determine a likelihood that the fibrosis will progress rapidly to a late-stage fibrosis in the subject.

18. A method of treating a subject for fibrosis or for a medical condition associated with progression of fibrosis, said method comprising:
   (a) (i) receiving a test result obtained by performing the method according to claim 1 wherein the test results determine that fibrosis has developed in the subject or that there is a strong likelihood that fibrosis will develop or progress to a late fibrosis or progress rapidly to a late-stage fibrosis in the subject; or
   (ii) receiving an indication or recommendation to treat a subject for the fibrosis or the medical condition based on a test result obtained by performing the method according to claim 1, wherein the test results determine that fibrosis has developed in the subject or that there a strong likelihood that the subject is susceptible to fibrosis and/or that fibrosis will progress rapidly to a late-stage in the subject; and
   (b) treating a subject for the fibrosis and/or the medical condition based on the test result or indication or recommendation.

19. The method according to claim 18, further comprising the first step of forwarding a DNA-containing sample obtained from a subject having no visible fibrosis or having early fibrosis to be analyzed by the method.

20. The method according to claim 18, wherein the subject has a medical condition associated with progression of fibrosis and treatment comprises treating the medical condition, and wherein said medical condition is selected from the group consisting of: a disease with secondary involvement of the liver, hemochromatosis, a congenital hepatic fibrosis, chronic hepatitis B, chronic hepatitis C, non-alcoholic steatohepatitis (NASH), primary biliary cirrhosis, primary sclerosing cholangitis, reduced hepatic blood flow, hepatic veno-occlusive disease, hepatocellular carcinoma, and scarring due to prior liver surgery.

21. The method according to claim 17, wherein treating the medical condition associated with progression of fibrosis comprises administering to the subject a medicament to thereby stop the fibrosis or progression of the fibrosis and/or reverse fibrotic changes in a fibrotic tissue or fibrotic organ of the subject.

22. The method according to claim 1, wherein the fibrosis is liver fibrosis.

23. The method according to claim 22, wherein the fibrosis is associated with a hepatitis virus infection and treatment comprises administering an antiviral compound to a subject in need thereof.

24. The method according to claim 22, wherein the treatment comprises removing a toxicity-causing agent or heavy metal or fatty acid from the body or body organ of a subject in need thereof.

25. The method according to claim 22, wherein the treatment comprises decompressing bile ducts in a subject in need thereof.

26. The method according to claim 1, wherein treating the fibrosis comprises administering to the subject a corticosteroid, penicillamine, tumour necrosis factor inhibitor (anti-TNF agent), a pan-caspase inhibitor, or other antifibrotic medicament.

27. A method of monitoring the efficacy of therapy for fibrosis or a medical condition associated with progression of liver fibrosis, said method comprising implementing a system for managing treatment of fibrosis or a medical condition associated with progression of fibrosis on a subject undergoing treatment for fibrosis or a condition associated therewith, and modifying the therapy according to the prognostic score data obtained over time, wherein the system comprises a computer comprising:
   (a) an input interface configured to receive prognostic score data from one or more genotyping assays on a DNA-containing sample obtained from a subject, wherein the one or more genotyping assays comprise analysis of single nuclear polymorphism (SNP) genotypes in a rs12979860 SNP from a human IL28B gene and a rs4374383NA SNP from a human MERTK gene for a subject having early-stage fibrosis or a medical condition associated with onset of fibrosis from a device, and wherein a plurality of data points are collected over a time course before commencement of therapy and/or during therapy and/or following cessation of therapy collected over time;
   (b) an input interface configured to receive data indicating a medical condition associated with onset of fibrosis in the subject and whether therapy is to treat the medical condition and/or the fibrosis;
   (c) a reference database of therapies for fibrosis and medical conditions associated with fibrosis;
   (d) a computer-readable storage medium for storing the data received at (a) and (b) and (c);
   (e) a data processor that is executed to plot calculate a prognostic score based on the stored data;
   (f) a processor for calculating a preferred therapy based on the stored data at (a) and (b) and (c); and
   (g) a port or readable interface for communicating the preferred therapy calculated by the processor to a user.

28. The method according to claim 1, further comprising:
   (a) performing one or more additional genotyping assays on the DNA-containing sample obtained from the subject to discriminate one or more further SNP genotypes in or at least linked to human IL28B gene or human MERTK gene, wherein the one or more further SNPs in or at least linked to human IL28B gene are selected from rs8099917 and a SNP in linkage disequilibrium with rs8099917, and the one or more further SNPs in or at least linked to human MERTK gene are selected from rs10211152 and a SNP in linkage disequilibrium with rs10211152, wherein the assay results indicate a likelihood that the subject will develop fibrosis and/or progress to a particular stage of fibrosis and/or progress rapidly to a late-stage fibrosis.

29. The method according to claim 28, wherein the method further comprises:
   (a) performing the one or more additional genotyping assays, wherein the genotypes in the human IL28B gene are in the SNP rs12979860 and the SNP rs8099917, and wherein the genotypes in the human MERTK gene are in the SNP rs4374383; and
   (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:
      (i) a CC genotype in rs12979860 and a TT genotype in rs8099917; and
      (ii) an AG genotype or GG genotype in rs4374383.

30. The method according to claim 28, wherein the method further comprises:
   (a) performing the one or more genotyping assays, wherein the genotypes in the human IL28B gene are in the SNP rs12979860, and wherein the genotypes in the human MERTK gene are in the SNP rs10211152 and the SNP rs4374383; and (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:

(i) a CC genotype in rs12979860; and (ii) a CC genotype in rs10211152 and an AG genotype or GG genotype in rs4374383.

31. The method according to claim 28, wherein the method comprises:

(a) performing the one or more genotyping assays, wherein the genotypes in the human IL28B gene are in the SNP rs12979860 and the SNP rs8099917, and wherein the genotypes in the human MERTK gene are in the SNP rs10211152 and the SNP rs4374383; and (b) correlating the genotyping assay results to the likelihood that the subject will develop fibrosis or progress rapidly to a late-stage fibrosis, wherein a combination of the following genotypes (i) and (ii) indicates a strong likelihood (O.R.>4.0, p<0.01) that the subject will develop fibrosis and/or progress rapidly to a late-stage fibrosis:

(i) a CC genotype in rs12979860 and a TT genotype in rs8099917; and (ii) a CC genotype in rs10211152 and an AG genotype or GG genotype in rs4374383.

32. The method according to claim 1, wherein performing one or more genotyping assays on the DNA-containing sample comprises performing the genotyping assays under conditions that discriminate between the following combinations of genotypes in the sample DNA:

(a) between homozygotes (CC), heterozygotes (CT) and alternate homozygotes (TT) at rs12979860; and (b) between homozygotes (GG), heterozygotes (AG) and alternate homozygotes (AA) at rs4374383; and optionally (c) between homozygotes (TT), heterozygotes (TG) and alternate homozygotes (GG) at rs8099917 and/or between homozygotes (CC), heterozygotes (CT) and alternate homozygotes (TT) at rs10211152.

33. The method according to claim 28, wherein a SNP in linkage disequilibrium with rs10211152 is selected from the group consisting of rs17175626 and rs6748256.

34. The method according to claim 27, wherein the computer and the device are configured to be in communication with each other to facilitate transfer of prognostic score data from the device to the computer.

35. The method according to claim 34, wherein the computer and the device are in wireless communication with each other.

* * * * *